(12) United States Patent
Wahl et al.

(10) Patent No.: US 8,288,439 B2
(45) Date of Patent: Oct. 16, 2012

(54) METHODS AND COMPOSITIONS FOR THE INHIBITION OF HIV-1 REPLICATION

(75) Inventors: Sharon M. Wahl, N. Potomac, MD (US); Nancy Vazquez-Maldonado, Chevy Chase, MD (US); Teresa Greenwell-Wild, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1236 days.

(21) Appl. No.: 10/578,536

(22) PCT Filed: Nov. 3, 2004

(86) PCT No.: PCT/US2004/036492
§ 371 (c)(1),
(2), (4) Date: Mar. 21, 2007

(87) PCT Pub. No.: WO2005/046732
PCT Pub. Date: May 26, 2005

(65) Prior Publication Data
US 2008/0242602 A1 Oct. 2, 2008

Related U.S. Application Data

(60) Provisional application No. 60/516,734, filed on Nov. 4, 2003.

(51) Int. Cl.
*A61P 31/18* (2006.01)
*A61K 31/192* (2006.01)
*A61K 38/16* (2006.01)

(52) U.S. Cl. ....... 514/569; 514/1.1; 514/44 A; 514/44 R
(58) Field of Classification Search .......... None
See application file for complete search history.

(56) References Cited

U.S. PATENT DOCUMENTS

| | | | |
|---|---|---|---|
| 5,916,919 A * | 6/1999 | Xu et al. | 514/557 |
| 6,869,925 B1 | 3/2005 | Eisenberg et al. | |
| 2003/0119732 A1 * | 6/2003 | Konopleva et al. | 514/12 |

FOREIGN PATENT DOCUMENTS

| WO | WO-94/06454 | 3/1994 |
|---|---|---|
| WO | WO-94/17097 | 8/1994 |
| WO | WO-01/88191 A | 11/2001 |
| WO | WO 2004016753 A2 * | 2/2004 |

OTHER PUBLICATIONS

Nasti et al. (1997) "Malignant tumors and AIDS" Biomed. Pharmacother. 51:243-251.*
Place et al. (Jul. 2003) "The novel synthetic triterpenoid, CDDO-imidazolide, inhibits inflammatory response and tumor growth in vivo" Clin. Cancer. Res. 9(7): 2798-806.*
Gomez et al., Cytoplasmic p21 WAF1/Cip1 Protects U937 Promonocytic Cells from HIV Mediated Apoptosis, XP002324902 (2002).
Kawata et al., Journal of Virology, 77(13):7291-7299 (2003).
Poluha et al., Molecular and Cellular Biology, 16(4):1335-1341 (1996).
Tian et al., Cancer Research, 60(3):679-684 (2000).
Gartel et al., Molecular Cancer Therapeutics, 1(8):639-649 (2002).

* cited by examiner

*Primary Examiner* — Sean McGarry
(74) *Attorney, Agent, or Firm* — Edwards Wildman Palmer LLP; Peter F. Corless; Christine C. O'Day

(57) ABSTRACT

This invention relates to methods and compositions for the attenuation of HIV-1 replication in human cells, and especially in human macrophages. The invention particularly concerns the use of inhibitors of P21 (CDKNIA) expression to attenuate such replication. The invention particularly concerns the use of antisense P21 oligonucleotides, siRNA and/or 2-cyano-3,12-dioxooleana-1,9-dien28-oic (CDDO) to attenuate such replication.

3 Claims, 14 Drawing Sheets

Figure 5A
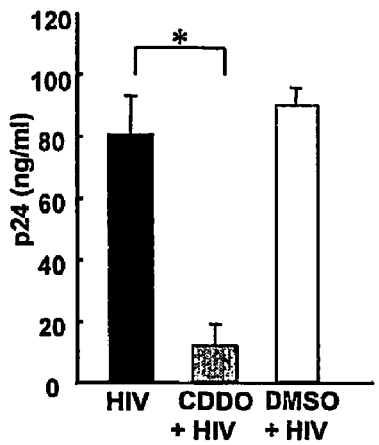
Figure 5B
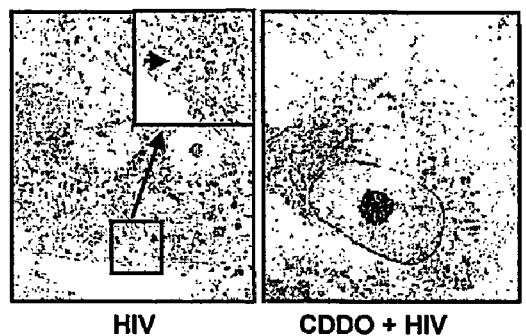
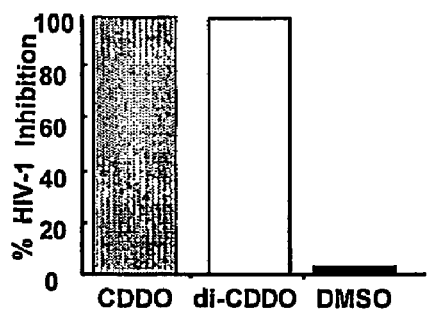
Figure 5C
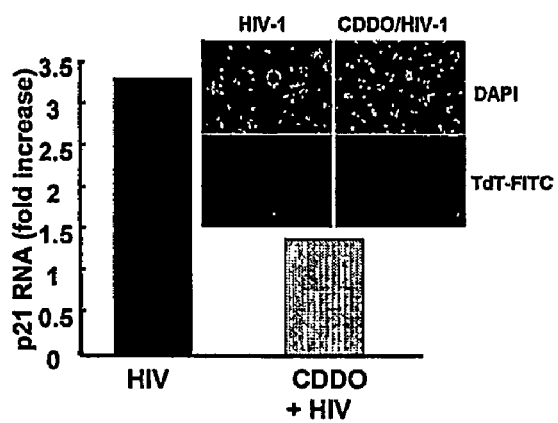
Figure 5D
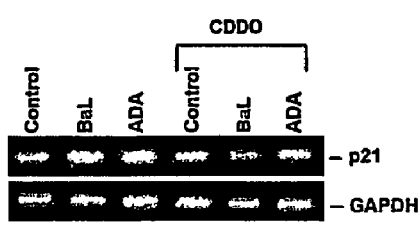
Figure 5E
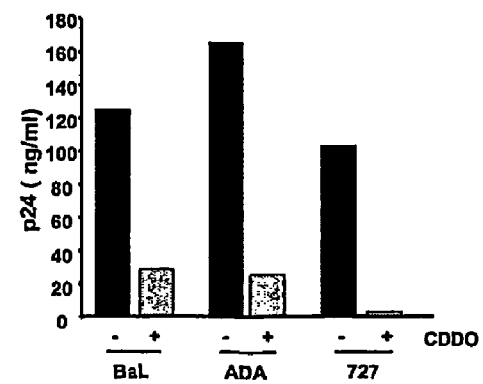
Figure 5F

SEQUENCE LISTING

```
<160> NUMBER OF SEQ ID NOS: 14

<210> SEQ ID NO 1
<211> LENGTH: 15
<212> TYPE: RNA
<213> ORGANISM: Homo sapiens

<400> SEQUENCE: 1
uccgcgccca gcucc                                                       15

<210> SEQ ID NO 2
<211> LENGTH: 15
<212> TYPE: RNA
<213> ORGANISM: Homo sapiens

<400> SEQUENCE: 2
uccgcccgca gcucc                                                       15

<210> SEQ ID NO 3
<211> LENGTH: 2265
<212> TYPE: DNA
<213> ORGANISM: Homo sapiens

<400> SEQUENCE: 3
gctgccgaag tcagttcctt gtggagccgg agctgggcgc ggattcgccg aggcaccgag      60
gcactcagag gaggtgagag agcggcggca gacaacaggg gacccggggc cggcggccca     120
gagccgagcc aagcgtgccc gcgtgtgtcc ctgcgtgtcc gcgaggatgc gtgttcgcgg     180
gtgtgtgctg cgttcacagg tgtttctgcg gcaggcgcca tgtcagaacc ggctggggat     240
gtccgtcaga acccatgcgg cagcaaggcc tgccgccgcc tcttcggccc agtggacagc     300
```

-continued

```
gagcagctga gccgcgactg tgatgcgcta atggcgggct gcatccagga ggcccgtgag      360
cgatggaact tcgactttgt caccgagaca ccactggagg gtgacttcgc ctgggagcgt      420
gtgcggggcc ttggcctgcc caagctctac cttcccacgg ggccccggcg aggccgggat      480
gaattgggag gaggcaggcg gcctggcacc tcacctgctc tgctgcaggg gacagcagag      540
gaagaccatg tggacctgtc actgtcttgt acccttgtgc ctcgctcagg ggagcaggct      600
gaagggtccc caggtggacc tggagactct cagggtcgaa acggcggca gaccagcatg       660 acagatttct accactccaa acgccggctg atcttctcca agaggaagcc ctaatccgcc      720
cacaggaagc ctgcagtcct ggaagcgcga gggcctcaaa ggcccgctct acatcttctg      780
ccttagtctc agtttgtgtg tcttaattat tatttgtgtt ttaatttaaa cacctcctca      840
tgtacatacc ctggccgccc cctgcccccc agcctctggc attagaatta tttaaacaaa      900
aactaggcgg ttgaatgaga ggttcctaag agtgctgggc attttttattt tatgaaatac    960 tatttaaagc ctcctcatcc cgtgttctcc ttttcctctc tcccggaggt tgggtgggcc    1020
ggcttcatgc cagctacttc ctcctcccca cttgtccgct gggtggtacc ctctggaggg    1080
gtgtggctcc ttcccatcgc tgtcacaggc ggttatgaaa ttcacccccct ttcctggaca    1140 ctcagacctg aattcttttt catttgagaa gtaaacagat ggcactttga aggggcctca    1200
ccgagtgggg gcatcatcaa aaactttgga gtccccctcac ctcctctaag gttgggcagg    1260
gtgaccctga agtgagcaca gcctagggct gagctgggga cctggtaccc tcctggctct    1320 tgatacccc ctctgtcttg tgaaggcagg gggaaggtgg ggtcctggag cagaccaccc     1380
cgcctgccct catggcccct ctgacctgca ctggggagcc cgtctcagtg ttgagccttt    1440
tccctctttg gctcccctgt acctttgag gagcccccagc tacccttctt ctccagctgg    1500
gctctgcaat tcccctctgc tgctgtccct ccccccttgtc ctttcccttc agtaccctct    1560
cagctccagg tggctctgag gtgcctgtcc caccccacc cccagctcaa tggactggaa     1620
ggggaaggga cacacaagaa gaagggcacc ctagttctac ctcaggcagc tcaagcagcg    1680
accgccccct cctctagctg tgggggtgag ggtcccatgt ggtggcacag gcccccttga    1740
gtggggttat ctctgtgtta ggggtatatg atggggagt agatctttct aggagggaga     1800
cactggcccc tcaaatcgtc cagcgacctt cctcatccac cccatccctc cccagttcat    1860
tgcactttga ttagcagcgg aacaaggagt cagacatttt aagatggtgg cagtagaggc    1920
tatggacagg gcatgccacg tgggctcata tggggctggg agtagttgtc tttcctggca    1980
ctaacgttga gccctggag gcactgaagt gcttagtgta cttggagtat tggggtctga     2040
ccccaaacac cttccagctc ctgtaacata ctggcctgga ctgtttttctc tcggctcccc    2100 atgtgtcctg gttcccgttt ctccacctag actgtaaacc tctcgagggc agggaccaca    2160
ccctgtactg ttctgtgtct ttcacagctc ctcccacaat gctgaatata cagcaggtgc    2220
tcaataaatg attcttagtg actttaaaaa aaaaaaaaaa aaaaa                    2265
```

<210> SEQ ID NO 4
<211> LENGTH: 2265
<212> TYPE: DNA
<213> ORGANISM: Homo sapiens

<400> SEQUENCE: 4

```
tttttttttt tttttttttt aaagtcacta agaatcattt attgagcacc tgctgtatat       60
tcagcattgt gggaggagct gtgaaagaca cagaacagta cagggtgtgg tccctgccct      120
cgagaggttt acagtctagg tggagaaacg ggaaccagga cacatgggga gccgagagaa      180
```

-continued

| | |
|---|---|
| aacagtccag gccagtatgt tacaggagct ggaaggtgtt tggggtcaga ccccaatact | 240 |
| ccaagtacac taagcacttc agtgcctcca ggggctcaac gttagtgcca ggaaagacaa | 300 |
| ctactcccag ccccatatga gcccacgtgg catgccctgt ccatagcctc tactgccacc | 360 |
| atcttaaaat gtctgactcc ttgttccgct gctaatcaaa gtgcaatgaa ctggggaggg | 420 |
| atggggtgga tgaggaaggt cgctggacga tttgaggggc cagtgtctcc ctcctagaaa | 480 |
| gatctactcc cccatcatat acccctaaca cagagataac cccactcaag ggggcctgtg | 540 |
| ccaccacatg ggaccctcac cccacagct agaggagggg gcggtcgctg cttgagctgc | 600 |
| ctgaggtaga actagggtgc ccttcttctt gtgtgtccct tccccttcca gtccattgag | 660 |
| ctggggtgg gggtgggaca ggcacctcag agccacctgg agctgagagg gtactgaagg | 720 |
| gaaaggacaa gggggaggga cagcagcaga ggggaattgc agagcccagc tggagaagaa | 780 |
| gggtagctgg ggctcctcaa aaggtacagg ggagccaaag agggaaaagg ctcaacactg | 840 |
| agacgggctc cccagtgcag gtcagagggg ccatgagggc aggcggggtg gtctgctcca | 900 |
| ggaccccacc ttcccctgc cttcacaaga cagagggggg tatcaagagc caggagggta | 960 |
| ccaggtcccc agctcagccc taggctgtgc tcacttcagg gtcaccctgc caaccttag | 1020 |
| aggaggtgag gggactccaa agtttttgat gatgccccca ctcggtgagg cccctctcaaa | 1080 |
| gtgccatctg tttacttctc aaatgaaaaa gaattcaggt ctgagtgtcc aggaaagggg | 1140 |
| gtgaatttca taaccgcctg tgacagcgat gggaaggagc cacacccctc cagagggtac | 1200 |
| cacccagcgg acaagtgggg aggaggaagt agctggcatg aagccggccc acccaacctc | 1260 |
| cgggagagag gaaaaggaga acacgggatg aggaggcttt aaatagtatt tcataaaata | 1320 |
| aaaatgccca gcactcttag gaacctctca ttcaaccgcc tagttttgt ttaaataatt | 1380 |
| ctaatgccag aggctggggg gcagggggcg gccagggtat gtacatgagg aggtgtttaa | 1440 |
| attaaaacac aaataataat taagacacac aaactgagac taaggcagaa gatgtagagc | 1500 |
| gggcctttga ggccctcgcg cttccaggac tgcaggcttc ctgtgggcgg attagggctt | 1560 |
| cctcttggag aagatcagcc ggcgtttgga gtggtagaaa tctgtcatgc tggtctgccg | 1620 |
| ccgttttcga ccctgagagt ctccaggtcc acctgggac ccttcagcct gctcccctga | 1680 |
| gcgaggcaca agggtacaag acagtgacag gtccacatgg tcttcctctg ctgtcccctg | 1740 |
| cagcagagca ggtgaggtgc caggccgcct gcctcctccc aactcatccc ggcctcgccg | 1800 |
| ggcccccgtg ggaaggtaga gcttgggcag gccaaggccc cgcacacgct cccaggcgaa | 1860 |
| gtcaccctcc agtggtgtct cggtgacaaa gtcgaagttc atcgctcac gggcctcctg | 1920 |
| gatgcagccc gccattagcg catcacagtc gcggctcagc tgctcgctgt ccactgggcc | 1980 |
| gaagaggcg cggcaggcct tgctgccgca tgggttctga cggacatccc cagccggttc | 2040 |
| tgacatggcg cctgccgcag aaacacctgt gaacgcagca cacccgcg aacacgcatc | 2100 |
| ctcgcggaca cgcagggaca cacgcgggca cgcttggctc ggctctgggc cgccggcccg | 2160 |
| ggtcccctg ttgtctgccg ccgctctctc acctcctctg agtgcctcgg tgcctcggcg | 2220 |
| aatccgcgcc cagctccggc tccacaagga actgacttcg gcagc | 2265 |

<210> SEQ ID NO 5
<211> LENGTH: 1909
<212> TYPE: DNA
<213> ORGANISM: Mus musculus

<400> SEQUENCE: 5

| | |
|---|---|
| gagccgagag gtgtgagccg ccgcggtgtc agagtctagg ggaattggag tcaggcgcag | 60 |

| | |
|---|---|
| atccacagcg atatccagac attcagagcc acaggcacca tgtccaatcc tggtgatgtc | 120 |
| cgacctgttc cgcacaggag caaagtgtgc cgttgtctct tcggtcccgt ggacagtgag | 180 |
| cagttgcgcc gtgattgcga tgcgctcatg gcgggctgtc tccaggaggc ccgagaacgg | 240 |
| tggaactttg acttcgtcac ggagacgccg ctggagggca cttcgtctg ggagcgcgtt | 300 |
| cggagcctag gctgcccaa ggtctacctg agccctgggt cccgcagccg tgacgacctg | 360 |
| ggaggggaca agaggcccag tacttcctct gccctgctgc aggggccagc tccggaggac | 420 |
| cacgtggcct tgtcgctgtc ttgcactctg gtgtctgagc ggcctgaaga ttccccgggt | 480 |
| gggcccggaa catctcaggg ccgaaaacgg aggcagacca gcctgacaga tttctatcac | 540 |
| tccaagcgca gattggtctt ctgcaagaga aaaccctgaa gtgcccacgg gagccccgcc | 600 |
| ctcttctgct gtgggtcagg aggcctcttc cccatcttcg gccttagccc tcactctgtg | 660 |
| tgtcttaatt attatttgtg ttttaattta aacgtctcct gtatatacgc tgcctgccct | 720 |
| ctcccagtct ccaaacttaa agttatttaa aaaagaaca aaacaaaaca aaaaaaaacc | 780 |
| aaaacaaaac aaacctaaat tagtaggacg gtagggccct tagtgtgggg gatttctatt | 840 |
| atgtagatta ttattattta agcccctccc aacccaagct ctgtgtttcc tataccggag | 900 |
| gaacagtcct actgatatca acccatctgc atccgtttca cccaacccc ctcccccat | 960 |
| tccctgcctg gttccttgcc acttcttacc tggggtgat cctcagacct gaatagcact | 1020 |
| ttggaaaaat gagtaggact ttggggtctc cttgtcacct ctaaggccag ctaggatgac | 1080 |
| agtgaagcag tcacagccta gaacagggat ggcagttagg actcaaccgt aatatcccga | 1140 |
| ctcttgacat tgctcagacc tgtgaagaca ggaatggtcc ccactctgga tcccctttgc | 1200 |
| cactcctggg gagcccacct ctcctgtggg tctctgccag ctgcccctct attttggagg | 1260 |
| gttaatctgg tgatctgctg ctcttttccc ccaccccata cttcccccttc tgcaggtcgg | 1320 |
| caggaggcat atctaggcac ttgccccaca gctcagtgga ctggaaggga atgtatatgc | 1380 |
| agggtacact aagtgggatt ccctggtctt accttaggca gctccagtgg caaccccctg | 1440 |
| cattgtgggt ctagggtggg tccttggtgg tgagacaggc ctcccagagc attctatggt | 1500 |
| gtgtggtggt ggggtgggc ttatctggga tggggacccc agttgggtt tcagtgact | 1560 |
| tctcccattt cttagtagca gttgtacaag gagccaggcc aagatggtgt cttgggggct | 1620 |
| aagggagctc acaggacact gagcaatggc tgatcctttc tcagtgttga ataccgtggg | 1680 |
| tgtcaaagca cttagtgggt ctgactccag ccccaaacat ccctgtttct gtaacatcct | 1740 |
| ggtctggact gtctacccctt agcccgcacc ccaagaacat gtattgtggc tccctccctg | 1800 |
| tctccactca gattgtaagc gtctcacgag aagggacagc accctgcatt gtcccgagtc | 1860 |
| ctcacacccg acccccaaagc tggtgctcaa taaatacttc tcgatgatt | 1909 |

<210> SEQ ID NO 6
<211> LENGTH: 1909
<212> TYPE: DNA
<213> ORGANISM: Mus musculus

<400> SEQUENCE: 6

| | |
|---|---|
| aatcatcgag aagtatttat tgagcaccag ctttggggtc gggtgtgagg actcgggaca | 60 |
| atgcagggtg ctgtcccttc tcgtgagacg cttacaatct gagtggagac agggagggag | 120 |
| ccacaataca tgttcttggg gtgcgggcta agggtagaca gtccagacca ggatgttaca | 180 |
| gaaacaggga tgtttggggc tggagtcaga cccactaagt gctttgacac ccacggtatt | 240 |
| caacactgag aaaggatcag ccattgctca gtgtcctgtg agctccctta gccccaaga | 300 |

```
caccatcttg gcctggctcc ttgtacaact gctactaaga aatgggagaa gtcactgaga    360
accccaactg gggtccccat cccagataag cccaccccca ccaccacaca ccatagaatg    420
ctctgggagg cctgtctcac caccaaggac ccaccctaga cccacaatgc aggggggttgc   480 cactggagct gcctaaggta agaccaggga atcccactta gtgtaccctg catatacatt    540
cccttccagt ccactgagct gtggggcaag tgcctagata tgcctcctgc cgacctgcag    600
aaggggaagt atggggtggg ggaaaagagc agcagatcac cagattaacc ctccaaaata    660 gagggcagc tggcagagac ccacaggaga ggtgggctcc ccaggagtgg caaaggggat     720
ccagagtggg gaccattcct gtcttcacag gtctgagcaa tgtcaagagt cgggatatta    780
cggttgagtc ctaactgcca tccctgttct aggctgtgac tgcttcactg tcatcctagc    840
tggccttaga ggtgacaagg agaccccaaa gtcctactca tttttccaaa gtgctattca    900
ggtctgagga tcaccccag gtaagaagtg gcaaggaacc aggcagggaa tggggggagg    960
ggggttgggt gaaacggatg cagatggggtt gatatcagta ggactgttcc tccggtatag   1020
gaaacacaga gcttgggttg ggagggggctt aaataataat aatctacata atagaaatcc   1080
cccacactaa gggccctacc gtcctactaa tttaggtttg ttttgttttg gttttttttt    1140
gttttgtttt gttctttttt taaataactt taagtttgga gactgggaga gggcaggcag    1200
cgtatataca ggagacgttt aaattaaaac acaataata attaagacac acagagtgag     1260
ggctaaggcc gaagatgggg aagaggcctc ctgacccaca gcagaagagg gcgggggctcc   1320 cgtgggcact tcagggtttt ctcttgcaga agaccaatct gcgcttggag tgatagaaat    1380
ctgtcaggct ggtctgcctc cgttttcggc cctgagatgt tccgggccca cccggggaat    1440
cttcaggccg ctcagacacc agagtgcaag acagcgacaa ggccacgtgg tcctccggag    1500
ctggcccctg cagcagggca gaggaagtac tgggcctctt gtcccctccc aggtcgtcac    1560
ggctgcggga cccagggctc aggtagacct tgggcagccc taggctccga acgcgctccc    1620
agacgaagtt gccctccagc ggcgtctccg tgacgaagtc aaagttccac cgttctcggg    1680
cctcctggag acagcccgcc atgagcgcat cgcaatcacg gcgcaactgc tcactgtcca    1740
cgggaccgaa gagacaacgg cacactttgc tcctgtgcgg aacaggtcgg acatcaccac    1800
gattggtcat ggtgcctgtg gctctgaatg tctggatatc gctgtggatc tgcgcctgac    1860
tccaattccc ctagactctg acaccgcggc ggctcacacc tctcggctc                1909

<210> SEQ ID NO 7
<211> LENGTH: 20
<212> TYPE: DNA
<213> ORGANISM: Mus musculus

<400> SEQUENCE: 7
tgtcaggctg gtctgcctcc                                                 20

<210> SEQ ID NO 8
<211> LENGTH: 20
<212> TYPE: DNA
<213> ORGANISM: Homo sapiens

<400> SEQUENCE: 8
tgtcatgctg gtctgccgcc                                                 20

<210> SEQ ID NO 9
<211> LENGTH: 20
<212> TYPE: DNA
<213> ORGANISM: Mus musculus
```

<400> SEQUENCE: 9
acatcaccag gattggacat                                                    20

<210> SEQ ID NO 10
<211> LENGTH: 23
<212> TYPE: DNA
<213> ORGANISM: Homo sapiens

<400> SEQUENCE: 10
acatccccag ccggttctga cat                                                23

<210> SEQ ID NO 11
<211> LENGTH: 202
<212> TYPE: DNA
<213> ORGANISM: Homo sapiens

<400> SEQUENCE: 11
accatcccct tcctcacctg aaaacaggca gcccaaggac aaaatagcca ccagcctctt         60
ctatgccaga gctcaacatg ttgggacatg ttcctgacgg ccagaaagcc aatcagagcc        120
acagcctgct gcccaagcat gttcctggga agcaggcagc atagggatgg agggaggctc        180
agcctggggg aacaagagtg cc                                                 202

<210> SEQ ID NO 12
<211> LENGTH: 202
<212> TYPE: DNA
<213> ORGANISM: Homo sapiens

<400> SEQUENCE: 12
ggcactcttg ttcccccagg ctgagcctcc ctccatccct atgctgcctg cttcccagga         60
acatgcttgg gcagcaggct gtggctctga ttggctttct ggccgtcagg aacatgtccc        120
aacatgttga gctctggcat agaagaggct ggtggctatt ttgtccttgg gctgcctgtt        180
ttcaggtgag aagggggatg gt                                                 202

<210> SEQ ID NO 13
<211> LENGTH: 160
<212> TYPE: PRT
<213> ORGANISM: Homo sapiens

<400> SEQUENCE: 13

Met Ser Glu Pro Ala Gly Asp Val Arg Gln Asn Pro Cys Gly Ser Lys
 1               5                  10                  15

Ala Cys Arg Arg Leu Phe Gly Pro Val Asp Ser Glu Gln Leu Ser Arg
             20                  25                  30

Asp Cys Asp Ala Leu Met Ala Gly Cys Ile Gln Glu Ala Arg Glu Arg
         35                  40                  45

Trp Asn Phe Asp Phe Val Thr Glu Thr Pro Leu Glu Gly Asp Phe Ala
     50                  55                  60

Trp Glu Arg Val Arg Gly Leu Gly Leu Pro Lys Leu Tyr Leu Pro Thr
 65                  70                  75                  80

Gly Pro Arg Arg Gly Arg Asp Glu Leu Gly Gly Gly Arg Arg Pro Gly
                 85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

```
Thr Ser Met Thr Asp Phe Tyr His Ser Lys Arg Arg Leu Ile Phe Ser
145                 150                 155                 160

<210> SEQ ID NO 14
<211> LENGTH: 18
<212> TYPE: DNA
<213> ORGANISM: Mus musculus

<400> SEQUENCE: 14
tggatccgac atgtcaga                                              18
```

METHODS AND COMPOSITIONS FOR THE INHIBITION OF HIV-1 REPLICATION

CROSS-REFERENCE TO RELATED APPLICATIONS

This application claims priority to U.S. Patent application Ser. No. 60/516,734 (filed on Nov. 4, 2004), which application is herein incorporated by reference.

STATEMENT OF GOVERNMENTAL INTEREST

This invention was funded by the National Institutes of Health, Department of Health and Human Services. The United States Government has certain rights to this invention.

FIELD OF THE INVENTION

This invention relates to methods and compositions for the attenuation of HIV-1 replication in human cells, and especially in human macrophages. The invention particularly concerns the use of inhibitors of P21 (CDKN1A) expression to attenuate such replication. The invention particularly concerns the use of antisense P21 oligonucleotides and/or 2-cyano-3,12-dioxooleana-1,9-dien-28-oic (CDDO) to attenuate such replication.

BACKGROUND OF THE INVENTION

Human immunodeficiency virus-1 (HIV-1) is the causative agent of acquired immune deficiency syndrome (AIDS) and related disorders (Gallo, R. C. et al. (1983) "Isolation of human T-cell leukemia virus in acquired immune deficiency syndrome (AIDS)," Science 220(4599):865-7; Barre-Sinoussi, F. et al. "ISOLATION OF A T-LYMPHOTROPIC RETROVIRUS FROM A PATIENT AT RISK FOR ACQUIRED IMMUNE DEFICIENCY SYNDROME (AIDS)," (1983) Science 220:868-870; Gallo, R. et al. (1984) "FREQUENT DETECTION AND ISOLATION OF CYTOPATHIC RETROVIRUSES (HTLV-III) FROM PATIENTS WITH AIDS AND AT RISK FOR AIDS," Science 224:500-503; Teich, N. et al. (1984) "RNA TUMOR VIRUSES," Weiss, R. et al. (eds.) Cold Spring Harbor Press (NY) pp. 949-956).

T lymphocytes and macrophages expressing CD4 and the seven transmembrane chemokine co-receptors CXCR4 and CCR5 are susceptible to HIV-1 infection (Berger, E. A. et al. (1999) "CHEMOKINE RECEPTORS AS HIV-1 CORECEPTORS; ROLES IN VIRAL ENTRY, TROPISM, AND DISEASE," Annu. Rev. Immunol. 17:657-700). In contrast to $CD4^+$ lymphocytes, HIV-1 infected macrophages can resist cell death despite viral infection. Viruses within and shed from infected macrophages may serve as a reservoir for the infection of additional cells (Wahl, S. M. et al. (1996) In: MACROPHAGE FUNCTION IN HIV INFECTION, pages 303-336; Orenstein, J. W. (2001) "THE MACROPHAGE IN HIV INFECTION," Immunobiology 204(5):598-602; Balestra, E. et al. (2001) "MACROPHAGES: A CRUCIAL RESERVOIR FOR HUMAN IMMUNODEFICIENCY VIRUS IN THE BODY," J. Biol. Regul. Homeost. Agents 15:272-276; Igarashi, T. et al. (2001) "MACROPHAGE ARE THE PRINCIPAL RESERVOIR AND SUSTAIN HIGH VIRUS LOADS IN RHESUS MACAQUES AFTER THE DEPLETION OF CD4+ T CELLS BY A HIGHLY PATHOGENIC SIMIAN IMMUNODEFICIENCY VIRUS/ HIV TYPE 1 CHIMERA (SHIV): IMPLICATIONS FOR HIV-1 INFECTIONS OF HUMANS," Proc. Natl. Acad. Sci. U.S.A. 98:658-663; Garbuglia, A. R. et al., (2001) "DYNAMICS OF VIRAL LOAD IN PLASMA AND HIV DNA IN LYMPHOCYTES DURING HIGHLY ACTIVE ANTI-RETROVIRAL THERAPY (HAART): HIGH VIRAL BURDEN IN MACROPHAGES AFTER 1 YEAR OF TREATMENT," J Chemother 13:188-194).

The persistence of HIV during highly active antiviral therapy, and poor susceptibility of macrophages to antiviral therapy (Igarashi, T. et al. (2001) "MACROPHAGE ARE THE PRINCIPAL RESERVOIR AND SUSTAIN HIGH VIRUS LOADS IN RHESUS MACAQUES AFTER THE DEPLETION OF CD4+T CELLS BY A HIGHLY PATHOGENIC SIMIAN IMMUNODEFICIENCY VIRUS/HIV TYPE 1 CHIMERA (SHIV): IMPLICATIONS FOR HIV-1 INFECTIONS OF HUMANS," Proc Natl Acad Sci USA 98:658-63; Garbuglia, A. R. et al. (2001) "DYNAMICS OF VIRAL LOAD IN PLASMA AND HIV DNA IN LYMPHOCYTES DURING HIGHLY ACTIVE ANTIRETROVIRAL THERAPY (HAART): HIGH VIRAL BURDEN IN MACROPHAGES AFTER 1 YEAR OF TREATMENT," J Chemother 13, 188-94) has intensified the interest in characterizing the mechanisms underlying infection and replication in this cell population.

Attempts to treat HIV infection have focused on the development of drugs that disrupt the viral infection and replication cycle (see, Mitsuya, H. et al. (1991) "TARGETED THERAPY OF HUMAN IMMUNODEFICIENCY VIRUS-RELATED DISEASE," FASEB J. 5:2369-2381). Such intervention could potentially inhibit the binding of HIV to cell membranes, the reverse transcription of the HIV RNA genome into DNA, the exit of the virus from the host cell and infection of new cellular targets, or inhibition of viral enzymes (see, U.S. Pat. No. 6,475,491). Thus, for example, soluble CD4 has been developed in an effort to competitively block the binding of HIV to lymphocytes (Smith, D. H. et al. (1987) "BLOCKING OF HIV-1 INFECTIVITY BY A SOLUBLE, SECRETED FORM OF THE CD4 ANTIGEN," Science 238:1704-1707; Schooley, R. et al. (1990) "RECOMBINANT SOLUBLE CD4 THERAPY IN PATIENTS WITH THE ACQUIRED IMMUNODEFICIENCY SYNDROME (AIDS) AND AIDS-RELATED COMPLEX. A PHASE I-II ESCALATING DOSAGE TRIAL," Ann. Int. Med. 112:247-253; Kahn, J. O. et al. (1990) "THE SAFETY AND PHARMACOKINETICS OF RECOMBINANT SOLUBLE CD4 (rCD4) IN SUBJECTS WITH THE ACQUIRED IMMUNODEFICIENCY SYNDROME (AIDS) AND AIDS-RELATED COMPLEX. A PHASE 1 STUDY," Ann. Int. Med. 112:254-261; Yarchoan, R. et al. (1989) Proc. $V^{th}$ Int. Conf. on AIDS, p 564, MCP 137). Similarly, the ability of antisense HIV-1 oligonucleotides to inhibit viral replication has been investigated (Maeda N et al. (1998) "INHIBITION OF HUMAN T-CELL LEUKEMIA VIRUS TYPE 1 REPLICATION BY ANTISENSE ENV OLIGODEOXYNUCLEOTIDE," Biochem Biophys Res Commun 243(1): 109-112).

Unfortunately, although considerable effort has been expended to design effective therapeutics, no curative antiretroviral drugs against AIDS currently exist. All available therapies are marred by substantial adverse side effects, and by the capacity of HIV to rapidly mutate into forms that are refractive to treatment (Miller, V. et al. (2001) "MUTATIONAL PATTERNS IN THE HIV GENOME AND CROSS-RESISTANCE FOLLOWING NUCLEOSIDE AND NUCLEOTIDE ANALOGUE DRUG EXPOSURE," Antivir Ther. 6 Suppl 3:25-44; Lerma, J. G. et al. (2001) "RESISTANCE OF HUMAN IMMUNODEFICIENCY VIRUS TYPE 1 TO REVERSE TRANSCRIPTASE AND PROTEASE INHIBITORS: GENOTYPIC AND PHENOTYPIC TESTING," J Clin Virol. 21(3):197-212; O'Brien, W. A. (2000) "RESISTANCE AGAINST REVERSE TRANSCRIPTASE INHIBITORS," Clin Infect Dis. 30 Suppl 2:S185-92; Wain-Hobson, S. (1996) "RUNNING THE GAMUT OF RETROVIRAL VARIATION," Trends Microbiol. 4(4):135-41; Lange J. (1995) "COMBINATION ANTIRETROVIRAL THERAPY. BACK TO THE FUTURE," Drugs. 49 Suppl 1:32-40). Thus, a continuing need exists for safe and effective anti-HIV therapeutics. The present invention is directed to this and other needs.

SUMMARY OF THE INVENTION

By monitoring virus production by multiple parameters including RNA, p24 antigen expression and ultra-structural detection of viral particles it has been possible to characterize the temporal events associated with the initial virus-macrophage encounter leading to massive viral replication. In parallel, macrophage changes in gene expression subsequent to virus-receptor interaction have been compared to uninfected cells by cDNA expression array. Analysis of 1200 genes at multiple intervals from initial HIV-1 binding through levels of massive replication (10-14 days) reveals a profile of gene modulation, which favored virus life cycle, and could influence recruitment and infection of additional HIV-1 host cells. One gene found to be consistently expressed following virus binding and re-expressed at the peak of HIV-1 replication is CDKN1A, also known as p21, Cip1 (Cdk interacting protein), or Waf1 (wild type p53-activated fragment), a protein associated with cell cycle regulation, anti-apoptotic response and cell differentiation (Dotto, G. P. (2000) "P21(WAF1/CIP1): MORE THAN A BREAK TO THE CELL CYCLE?" Biochim Biophys Acta 1471: M43-56). Importantly, modulation of p21 in vitro results in suppression of viral replication, and implicated this cellular protein as an interventional target.

In contrast to CD4$^+$ lymphocytes, HIV-1 infected macrophages typically resist cell death, support viral replication, and facilitate HIV-1 transmission. To elucidate how the virus commandeers macrophage intracellular machinery for its benefit, HIV-1 infected human monocyte-derived macrophages have been analyzed for viral-induced gene transcription by cDNA expression array. HIV-1 infection induces the transcriptional regulation of genes associated with host defense, signal transduction, apoptosis and cell cycle, including cyclin-dependent kinase inhibitor p21. CDKN1A/p21 expression follows a bimodal pattern with maximum levels occurring during HIV-1 replication. Treatment of macrophages with p21 anti-sense oligonucleotides or siRNA directed against p21 inhibits HIV-1 replication. Furthermore, the synthetic triterpenoid and peroxisome proliferator-activated receptor gamma (PPARg) ligand, 2-cyano-3,12-dioxooleana-1,9-dien-28-oic acid (CDDO), which influences p21 expression, drives a dose dependent suppression of viral replication. These data implicate p21 as a pivotal macrophage facilitator of viral replication. Moreover, regulators of p21, such as CDDO, provide an interventional approach to modulate HIV-1 replication.

This invention thus relates to methods and compositions for the attenuation of immunodeficiency virus replication in cells, and especially in macrophages. The invention particularly concerns the use of inhibitors of P21 (CDKN1A) expression to attenuate such replication. The invention particularly concerns the use of antisense P21 oligonucleotides, siRNA and/or 2-cyano-3,12-dioxooleana-1,9-dien-28-oic (CDDO) to attenuate such replication. The invention finds use in the treatment of AIDS, and in the treatment of lymphoma, especially in HIV-infected individuals.

In detail, the invention concerns a method of attenuating the transmission or infection of an immunodeficiency virus into a cell comprising providing to the cell an inhibitor of p21, wherein the inhibitor is provided in an amount and duration sufficient to cause an attenuation of at least 50% in the transmission or infection of the virus relative to an untreated cell. The invention particularly concerns the embodiments of such method wherein the immunodeficiency virus is a human immunodeficiency virus (HIV), and the cell is a human cell; wherein the immunodeficiency virus is a feline immunodeficiency virus (FIV), and the cell is a feline cell; or wherein the immunodeficiency virus is a simian immunodeficiency virus (SIV), and the cell is a simian cell.

The invention further provides a method of treating AIDS in an individual, comprising providing to HIV-1 infected cells of said individual an amount of a p21 inhibitor sufficient to attenuate the propagation of HIV, wherein said inhibitor is provided in an amount and duration sufficient to cause an attenuation of at least 50% in said propagation of HIV relative to untreated cells.

The invention particularly concerns the embodiments of such methods wherein the inhibitor of p21 is a polynucleotide, and especially wherein the polynucleotide is complementary to a portion of a p21 gene or p21 cDNA molecule.

The invention particularly concerns the embodiments of such methods wherein the p21 gene or p21 cDNA is of a human p21 gene or p21 cDNA molecule, or of a non-human animal or is a variant of a non-human p21 gene or p21 cDNA molecule.

The invention further concerns a method of treating AIDS in an individual, comprising providing to HIV-1 infected cells of the individual, or providing to HIV-1 suceptible cells of the individual prior to the infection of such cells by HIV-1, an amount of a p21 inhibitor sufficient to attenuate the propagation of HIV, wherein the inhibitor is provided in an amount and duration sufficient to cause an attenuation of at least 50% in the propagation of HIV relative to untreated cells.

The invention particularly concerns the embodiments of such methods wherein the polynucleotide comprises at least 10 contiguous nucleotides of SEQ ID NO.:4 (and in particular wherein the polynucleotide comprises at least 10 contiguous nucleotides of SEQ ID NO.:8 or SEQ ID NO.:10) or at least 10 contiguous nucleotides of SEQ ID NO.:6 (and in particular wherein the polynucleotide comprises at least 10 contiguous nucleotides of SEQ ID NO.:7 or SEQ ID NO.:9).

The invention further concerns the embodiments of the above methods wherein the inhibitor of p21 is a protein or organic molecule other than a polynucleotide, and in particular concerns the embodiment of such method wherein the inhibitor is 2-cyano-3,12-dioxooleana-1,9-dien-28-oic acid (CDDO), or a salt or derivative thereof.

The invention further concerns a pharmaceutical composition comprising an inhibitor of p21 and an excipient or carrier, wherein the inhibitor is present in an amount sufficient to attenuate the propagation of HIV, wherein the inhibitor is present in the composition in an amount sufficient to cause an attenuation of at least 50% in the propagation of HIV relative to untreated cells.

The invention particularly concerns the embodiments of such composition wherein the inhibitor of p21 is a polynucleotide, and especially wherein the polynucleotide is complementary to a portion of a p21 gene or p21 cDNA molecule. The invention particularly concerns the embodiments of such compositions wherein the p21 gene or p21 cDNA is of a human p21 gene or p21 cDNA molecule, or of a non-human animal or is a variant of a non-human p21 gene or p21 cDNA molecule. The invention further particularly concerns an inhibitor of an upstream or downstream modulator of p21 production or action (i.e., a p21 inhibitor molecule.

The invention further particularly concerns the embodiments of such compositions wherein the polynucleotide comprises at least 10 contiguous nucleotides of SEQ ID NO.:4 (and in particular wherein the polynucleotide comprises at least 10 contiguous nucleotides of SEQ ID NO.:8 or SEQ ID NO.:10) or at least 10 contiguous nucleotides of SEQ ID NO.:6 (and in particular wherein the polynucleotide comprises at least 10 contiguous nucleotides of SEQ ID NO.:7 or SEQ ID NO.:9).

The invention further concerns the embodiments of the above compositions wherein the inhibitor of p21 is a protein or organic molecule other than a polynucleotide, and in particular concerns the embodiment of such method wherein the inhibitor is 2-cyano-3,12-dioxooleana-1,9-dien-28-oic acid (CDDO), or a salt or derivative thereof.

BRIEF DESCRIPTION OF THE FIGURES

FIG. 1A: Macrophages are exposed to an R5 strain of HIV-1 for 90 min., washed, and total RNA extracted at the indicated time periods and examined by Northern blot analysis with a $^{32}$P-labeled cDNA probe for HIV-1 (Wahl, S. M. et al. (1991) "MACROPHAGE-AND ASTROCYTE-DERIVED TRANSFORMING GROWTH FACTOR BETA AS A MEDIATOR OF CENTRAL NERVOUS SYSTEM DYSFUNCTION IN ACQUIRED IMMUNE DEFICIENCY SYNDROME," J Exp Med 173: 981-991). Bands of 9.1 and 4.3 kb correspond to viral gag/pol and env mRNA respectively. FIG. 1B: Supernatants are collected from infected cultures (days 1-15) and examined by ELISA for p24. FIG. 1C: Macrophages are incubated for the indicated intervals (3-10 days) after infection, fixed in gluteraldehyde and process for transmission electron microscopy (TEM). Original magnification 10,000×. Ultrastructural analysis of infected cells reveals virions (FIG. 1C and FIG. 1D) in macrophages by 5-7 days post infection, with increasing viral numbers per cell (FIG. 1C) and numbers of infected macrophages (FIG. 1D) most evident>day 10 as quantified by counting >200 cells/time point. Data correspond to a representative experiment (n≧4).

FIG. 2A: Distribution of transcription changes in macrophages 3-6 hr after exposure to HIV. Numbers represent % of total upregulated genes (134/1200) associated with the indicated categories in ≧4 donors. FIG. 2B Transcription related genes upregulated ≧2 fold after 3-6 hours in HIV-1 infected macrophages. FIG. 2C: Signal transduction-related genes upregulated ≧2 fold above parallel cultures in descending order. FIGS. 2D-2E depict the fold change in gene expression in HIV-1-treated macrophages compared to gene expression levels from mock-infected macrophages from the same donor at intervals from 0.25 to 14 days (mean values, n=3;*p≦0.05 RM-ANOVA). The legend for FIGS. 2D-2E is shown in FIG. 2E.

FIG. 3A: Kinetic profile of p21 expression determined by cDNA expression array following HIV infection from day 0.25-14 days (n=3). FIG. 3B: RPA analysis of total mRNA from uninfected and HIV-1 infected macrophages at the indicated time points confirms enhanced gene expression for p21, with minimal effect on p53 (representative donor, n=2). FIG. 3C: Graphic representation of densitometry analysis of RPA for p21 and p53 genes (shown in FIG. 3B) normalized to GAPDH. FIG. 3D: Macrophages are infected with HIV-1$_{BAL}$, the laboratory viral isolate ADA or primary clinical isolate 727, washed and total RNA collected after 12 days and analyzed for p21 transcription by PCR.

FIG. 4A: Overlay confocal images from differential interference contrast (DIC) (1, 4) and immunofluorescence (Texas Red) for p21 labeling in uninfected (1, 2, and 3) and virus infected cells (4, 5 & 6) (original image 400×). At higher magnification (original 1000×, 3 & 6), infected-macrophages express increased nuclear and cytoplasmic p21 protein when compared with control cells. FIG. 4B: Densitometric fluorescence intensity (FI) analysis using confocal microscopy and Metamorph (Universal Imaging) analysis confirm enhanced nuclear and cytoplasmic p21 protein as represented by the signal intensity across equal line segments sampling nuclear or cytoplasmic regions (representative experiment, n=3). FIG. 4C: Western blot analysis shows increased p21 protein expression in HIV-1-infected macrophages. HIV-1 infected cells (12 days) show at least a two fold increase in p21 protein expression as indicated by immunoprecipitation as quantified by densitometry analysis relative to uninfected cells (n=3).

FIGS. 5A-5F illustrate inhibition of HIV-1 replication in macrophages by CDDO and di-CDDO. FIG. 5A: Macrophages were pre-treated with CDDO or DMSO as a control for 45 min and then infected with HIV-1$_{BaL}$. CDDO-treated macrophages show reduced viral replication as quantitated by p24 levels compared with DMSO control and untreated cells (day 10) (n=3,*P=0.01). Supernatants were collected on day 12 for p24 Ag analysis by ELISA and cells processed by TEM (FIG. 5B; FIG. 5C). Ultrastructural analysis demonstrates dramatically reduced numbers of infected cells and in the few remaining HIV positive cells, very few virions were identified in cultures treated with CDDO. Analysis of ≧200 cells/treatment condition revealed the absence or near absence of detectable virions. (FIG. 5D) CDDO treated cells infected with HIV-1 demonstrate reduced p21 transcription as determined by ribonuclease protection assay (day 12 post-infection shown) (mean, n=2). Inset: TdT-FITC and DAPI staining of cultures that were infected with HIV-1 and were treated or not with CDDO (FIG. 5D). FIG. 5E: Macrophages were infected with HIV-1$_{BaL}$ or ADA and treated or not with CDDO (0.1 μM) and analyzed by PCR for p21 and GAPDH. FIG. 5F: Supernatants (12 days) collected from HIV-1$_{BaL}$, ADA or 727 infected cells that were treated or not with CDDO were analyzed for viral replication by p24 ELISA.

FIG. 6A: p21 specific oligonucleotides (50 nM), but not control oligonucleotide inhibit HIV-1 growth in replicate cultures as determined by p24 levels (day 12 shown) (% of positive HIV control, no oligo treatment). FIG. 6B: Macrophages were treated with p21 siRNA duplexes (50 μg) five days prior to HIV infection (% of positive HIV control, no siRNA treatment) (representative experiment, n=3). Percent of HIV-1 infection was determined comparing the p24 levels in untreated vs siRNA treated macrophages. FIG. 6C: Cells treated with p21 and negative control siRNA (5 days) were analyzed by flow cytometry for CD4 and CCR5 cell surface expression. FIG. 6D: Nested PCR to detect pro-viral DNA on days 1 and 2 after HIV-1$_{BaL}$ infection in macrophages treated with p21 or negative control si RNA. Control represents uninfected cells.

FIG. 7A: Cells treated with Vpr (6 μg/ml) for 3 hr show increased gene transcription (FIG. 7A) and protein expression for p21 (FIG. 7B). FIG. 7C: Macrophages were infected with the wild type (wt) virus type clone pNLAD8, or pNLAD8 Vpr minus (#1) or pNLAD8-delta R (#2) R5 macrophage tropic viruses and 12 day supernatants analyzed by p24 ELISA. FIG. 7D: Total RNA was isolated from cells infected with the viruses as indicated in FIG. 7C and analyzed for p21 and GAPDH by PCR. Representative experiment, n=2.

DESCRIPTION OF THE PREFERRED EMBODIMENTS

Figure 1A:
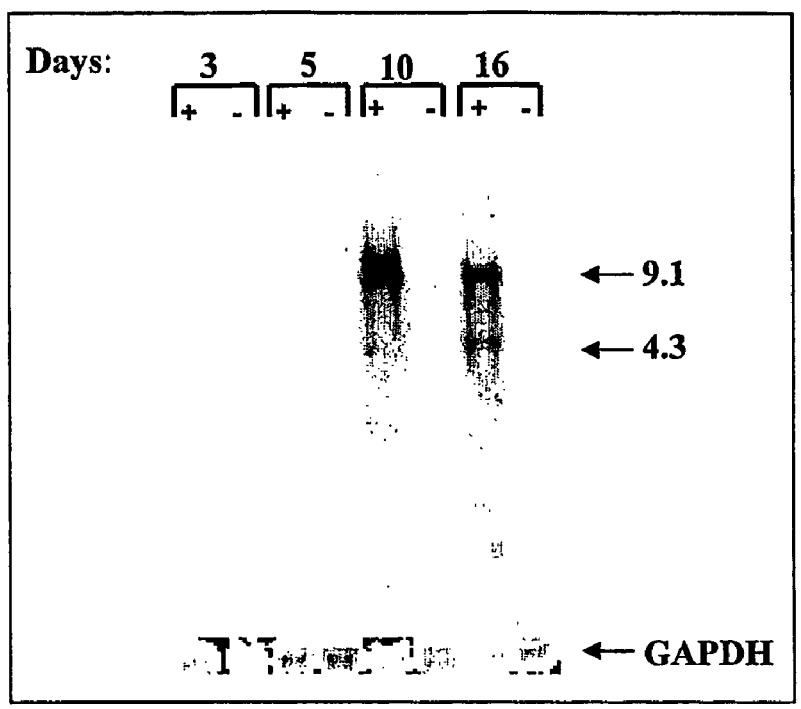
FIGS. 1A-1D illustrate the kinetics of HIV-1 infection in monocyte-derived adherent macrophages.

The present invention relates to methods and compositions for the attenuation of HIV-1 replication in human cells, and especially in human macrophages. As used herein, such "attenuation" is preferably of a magnitude sufficient to mediate a reduction of at least 50%, more preferably 60%, most preferably 80%, or greater in the replication, propagation or transmission of HIV.

The present invention derives in part from the recognition that the replication of human cells has been found to be tightly coordinated by the expression and interaction of an array of cell cycle regulatory proteins. Any of the genes described herein that are induced by HIV-1 are potentially able to serve as targets for achieving the inhibition of HIV-1. CDKN1A, also known as p21Cip1 (Cdk interacting protein), or Waf1 (wild type p53-activated fragment), is one of these proteins (Dotto, G. P. (2000) "P21(WAF1/Cip1): MORE THAN A BREAK TO THE CELL CYCLE?," Biochim. Biophys. Acta 1471:M43-M56). The loss of CDKN1A expression has been observed in many tumor cells, suggesting a role for the protein in preventing malignant progression. Thus, in a preferred embodiment, the present invention contemplates that agents that inhibit p21 expression or function serve to inhibit HIV-1. Such agents include antibodies (including single chain immunoglobulins, chimeric antibodies, etc.) that are immunologically reactive with p21 (i.e., able to bind to p21 epitopes), molecules that interfere with p21 function (e.g., CDDO and its analogues), polynucleotides capable of inhibiting p21 transcription or translation (e.g., siRNA, antisense molecules, etc.), and p21 inhibitor molecules. All such molecules are inhibitors of p21, as that term is employed herein.

HIV-1 and p21 are discussed in U.S. Pat. Nos. 6,359,124; 5,965,722; 5,889,156; 6,548,657; 6,511,847; 6,489,163; 6,410,010; 6,379,965; 6,204,248; 6,133,444; 6,069,134; 5,866,698; 5,861,290; 5,834,440; 5,795,870; 5,766,882; 5,747,469; and 5,693,769.

Although macrophages express the requisite CD4 and chemokine co-receptors making them susceptible targets, and R5 viral variants are preferentially transmitted, it has remained a challenge to identify HIV-1 positive macrophages early after viral exposure in mucosal tissues (Schacker, T. et al. (2001) "PRODUCTIVE INFECTION OF T CELLS IN LYMPHOID TISSUES DURING PRIMARY AND EARLY HUMAN IMMUNODEFICIENCY VIRUS INFECTION," J Infect Dis 183:555-562) or in the absence of co-pathogens (Orenstein, J. M. et al. (1997) "MACROPHAGES AS A SOURCE OF HIV DURING OPPORTUNISTIC INFECTIONS," Science 276:1857-1861). When exposed to HIV-1, monocyte-derived macrophages (MDM) bind and/or internalize the virus, but the consequences of that interaction are ill defined. Whether the macrophages are triggered by this encounter to modify their phenotypic and functional repertoire or whether HIV-1 enters stealthily, and transiently remains unrecognized by the immune system, it is important to define the early stages when HIV-1 is gaining a foothold on the immune system and identify key signals which not only promote permissiveness for macrophage HIV-1 infection, but also promote replication.

One aspect of the present invention relates to the recognition that HIV-1 infection stimulates the expression of p21 (CDKN1A) protein in human macrophages (Vazquez, N. et al. (October 2002) "HIV-1 Enhancement of CDKN1A (p21) in Human Macrophages Is Associated with Viral Replication," 5$^{th}$ Intl. Workshop on HIV, Cells of Macrophage/Dendritic Lineage and Other Reservoirs, Rome, Italy).

The Vpr gene product of HIV-1 has been found to prevent cell proliferation by activating p21 expression, suggesting that the upregulation of p21 by HIV-1 Vpr may have important consequences in HIV-1 pathogenesis (Chowdhury I. H. et al. (2003) "HIV-1 VPR ACTIVATES CELL CYCLE INHIBITOR P21/WAF1/CIP1: A POTENTIAL MECHANISM OF G2/M CELL CYCLE ARREST," Virol. 305:371-377). A similar relationship has been disclosed between p21 and HIV-1 Nef (Fackler, O. T. et al. (2000) "P21-ACTIVATED KINASE 1 PLAYS A CRITICAL ROLE IN CELLULAR ACTIVATION BY NEF," Mol Cell Biol. 20:2619-2627; Hiipakka M et al. (2001) "INHIBITION OF CELLULAR FUNCTIONS OF HIV-1 NEF BY ARTIFICIAL SH3 DOMAINS," Virol. 286:152-159; Nunn M F et al. (1996) "HUMAN IMMUNODEFICIENCY VIRUS TYPE 1 NEF ASSOCIATES WITH A MEMBER OF THE P21-ACTIVATED KINASE FAMILY," J. Virol. 70:6157-6161; Renkema G H et al. (1999) "IDENTIFICATION OF THE NEF-ASSOCIATED KINASE AS P21-ACTIVATED KINASE 2," Curr Biol. 9:1407-1410).

Additionally, Clark, E. et al. disclosed that the treatments (such as gamma irradiation) that cause a loss of cell cycle control at the $G_1$/S checkpoint cause HIV-1 infected cells to lose p21 function, and undergo apoptosis (Clark E et al. (2000) "LOSS OF G(1)/S CHECKPOINT IN HUMAN IMMUNODEFICIENCY VIRUS TYPE 1-INFECTED CELLS IS ASSOCIATED WITH A LACK OF CYCLIN-DEPENDENT KINASE INHIBITOR P21/WAF1," J. Virol. 74:5040-5052). Gomez, T. et al. www.retroconference.org/2002/Posters/13446.pdf; "CYTOPLASMIC P21$^{WAF1/CIP1}$ PROTECTS U937 PROMONOCYTIC CELLS FROM HIV MEDIATED APOPTOSIS") disclose that the administration of p21-antisense oligonucleotides to promonocytic cells suppressed p21 levels in the cells, and accelerated the death of the HIV-infected cells. The results are stated to indicate that p21 confers resistance to HIV-induced apoptosis in promonocytic cells, and to suggest a possible mechanism for the persistence of its infection in cells such as macrophages.

Antisense oligonucleotides of p21 have been used to affect cell-cycle transit in astrocytoma cells. (Jinbo Liu, et al. (2000) "ANTI-SENSE OLIGONUCLEOTIDE OF P21 (WAF1/CIP1) PREVENTS INTERLEUKIN 4-MEDIATED ELEVATION OF P27(KIP1) IN LOW GRADE ASTROCYTOMA CELLS," Oncogene 19:661-669). The oligonucleotides had the sequences:

```
SEQ ID NO: 1:    5'-ucc gcg ccc agc ucc-3'
and

SEQ ID NO: 2:    5'-ucc gcc cgc agc ucc-3'.
```

The present invention thus particularly concerns the use of one or more p21 inhibitors to prevent or attenuate the infection of additional host cells, and as such to provide a therapy for AIDS and its simian and feline counterparts.

As used herein, the term "p21 inhibitor" is intended to denote any of a variety of molecules that function to suppress or prevent p21 activity. Such inhibitors can be, for example, transcriptional inhibitors, such as promoter blockers, RNAi molecules, antisense polynucleotides of the p21 gene or cDNA, or allelic or non-human species variants thereof. Alternatively, such molecules can comprise translational inhibitors of p21, molecules that inhibit or otherwise interfere with p21 function, etc.

As used herein, an allelic variant of a p21 polynucleotide is a polynucleotide having the sequence of a naturally occurring allele of the p21 gene or cDNA thereof, or of a non-naturally occurring polynucleotide that is 80% homologous, and more preferably 90% homologous, and most preferably comprises a sequence that has at least 10, and more preferably, at least 20 contiguous nucleotides that are identical in sequence to a portion of a naturally occurring p21 gene or cDNA. Examples of such sequences include NCBI accession Nos. BC000312 and BC013967. As used herein, a non-human species variant of a p21 polynucleotide is a polynucleotide having the sequence of the p21 gene or cDNA of a non-human animal, for example a mouse or rat. Examples of such sequences include NM 007669 and U24174.

Antisense molecules suitable for use in the present invention can be identified as polynucleotide molecules having a length of 10-250, or more preferably 10-150, and most preferably, 10-100 nucleotides that are complementary to a portion of SEQ ID NO.:3 (the human p21 gene, see Xiong, Y. et al. (1993) "P21 IS A UNIVERSAL INHIBITOR OF CYCLIN KINASES," Nature 366:701-704 (1993); el-Deiry, W. S. et al. (1993) "WAF1, A POTENTIAL MEDIATOR OF P53 TUMOR SUPPRESSION," Cell 75:817-825 (1993); Harper, J. W. et al. (1993) "THE P21 CDK-INTERACTING PROTEIN CIP1 IS A POTENT INHIBITOR OF G1 CYCLIN-DEPENDENT KINASES," Cell 75:805-816) or allelic or non-human species variants thereof, especially the murine p21 gene (NM 007669).

```
SEQ ID NO.: 3:
   1  gctgccgaag tcagttcctt gtggagccgg agctgggcgc ggattcgccg
  51  aggcaccgag gcactcagag gaggtgagag agcggcggca gacaacaggg
 101  gaccccgggc cggcggccca gagccgagcc aagcgtgccc gcgtgtgtcc
 151  ctgcgtgtcc gcgaggatgc gtgttcgcgg gtgtgtgctg cgttcacagg
 201  tgtttctgcg gcaggcgcca tgtcagaacc ggctggggat gtccgtcaga
 251  acccatgcgg cagcaaggcc tgccgccgcc tcttcggccc agtggacagc
 301  gagcagctga gccgcgactg tgatgcgcta atggcgggct gcatccagga
 351  ggcccgtgag cgatggaact tcgactttgt caccgagaca ccactggagg
 401  gtgacttcgc ctgggagcgt gtgcggggcc ttggcctgcc caagctctac
 451  cttcccacgg ggccccggcg aggccgggat gagttgggag gaggcaggcg
 501  gcctggcacc tcacctgctc tgctgcaggg gacagcagag gaagaccatg
 551  tggacctgtc actgtcttgt acccttgtgc ctcgctcagg ggagcaggct
 601  gaagggtccc caggtggacc tggagactct cagggtcgaa aacggcggca
 651  gaccagcatg acagatttct accactccaa acgccggctg atcttctcca
 701  agaggaagcc ctaatccgcc cacaggaagc ctgcagtcct ggaagcgcga
 751  gggcctcaaa ggcccgctct acatcttctg ccttagtctc agtttgtgtg
 801  tcttaattat tatttgtgtt ttaatttaaa cacctcctca tgtacatacc
 851  ctggccgccc cctgccccccc agcctctggc attagaatta tttaaacaaa
 901  aactaggcgg ttgaatgaga ggttcctaag agtgctgggc atttttattt
 951  tatgaaatac tatttaaagc ctcctcatcc cgtgttctcc ttttcctctc
1001  tcccggaggt tgggtgggcc ggcttcatgc cagctacttc ctcctcccca
1051  cttgtccgct gggtggtacc ctctggaggg gtgtggctcc ttcccatcgc
1101  tgtcacaggc ggttatgaaa ttcaccccct ttcctggaca ctcagacctg
1151  aattcttttt catttgagaa gtaaacagat ggcactttga aggggcctca
1201  ccgagtgggg gcatcatcaa aaactttgga gtcccctcac ctcctctaag
1251  gttgggcagg gtgaccctga agtgagcaca gcctagggct gagctgggga
1301  cctggtaccc tcctggctct tgataccccc ctctgtcttg tgaaggcagg
1351  gggaaggtgg ggtcctggag cagaccaccc cgcctgccct catggcccct
1401  ctgacctgca ctggggagcc cgtctcagtg ttgagccttt tccctctttg
1451  gctcccctgt accttttgag gagccccagc taccttctt ctccagctgg
1501  gctctgcaat tcccctctgc tgctgtccct ccccccttgtc ctttccctc
1551  agtaccctct cagctccagg tggctctgag gtgcctgtcc cacccccacc
1601  cccagctcaa tggactggaa ggggaaggga cacacaagaa gaagggcacc
1651  ctagttctac ctcaggcagc tcaagcagcg accgccccct cctctagctg
1701  tgggggtgag ggtcccatgt ggtggcacag gcccccttga gtggggttat
1751  ctctgtgtta ggggtatatg atgggggagt agatcttttct aggagggaga
```

```
1801  cactggcccc tcaaatcgtc cagcgacctt cctcatccac cccatccctc
1851  cccagttcat tgcactttga ttagcagcgg aacaaggagt cagacatttt
1901  aagatggtgg cagtagaggc tatggacagg gcatgccacg tgggctcata
1951  tggggctggg agtagttgtc tttcctggca ctaacgttga gccctggag
2001  gcactgaagt gcttagtgta cttggagtat tggggtctga ccccaaacac
2051  cttccagctc ctgtaacata ctggcctgga ctgttttctc tcggctcccc
2101  atgtgtcctg gttcccgttt ctccacctag actgtaaacc tctcgagggc
2151  agggaccaca ccctgtactg ttctgtgtct ttcacagctc ctcccacaat
2201  gctgaatata cagcaggtgc tcaataaatg attcttagtg actttaaaaa
2251  aaaaaaaaaa aaaaa
```

Preferred p21 inhibitors of the present invention thus include polynucleotide fragments of SEQ ID NO: 4 (the antisense complement of SEQ ID NO.:3), or allelic or non-human species variants thereof:

```
SEQ ID NO.: 4:
   1  tttttttttt tttttttttt aaagtcacta agaatcattt attgagcacc
  51  tgctgtatat tcagcattgt gggaggagct gtgaaagaca cagaacagta
 101  cagggtgtgg tccctgccct cgagaggttt acagtctagg tggagaaacg
 151  ggaaccagga cacatgggga gccgagagaa aacagtccag gccagtatgt
 201  tacaggagct ggaaggtgtt tggggtcaga ccccaatact ccaagtacac
 251  taagcacttc agtgcctcca ggggctcaac gttagtgcca ggaaagacaa
 301  ctactcccag ccccatatga gcccacgtgg catgccctgt ccatagcctc
 351  tactgccacc atcttaaaat gtctgactcc ttgttccgct gctaatcaaa
 401  gtgcaatgaa ctggggaggg atggggtgga tgaggaaggt cgctggacga
 451  tttgaggggc cagtgtctcc ctcctagaaa gatctactcc cccatcatat
 501  acccctaaca cagagataac cccactcaag ggggcctgtg ccaccacatg
 551  ggaccctcac ccccacagct agaggagggg gcggtcgctg cttgagctgc
 601  ctgaggtaga actagggtgc ccttcttctt gtgtgtccct tccccttcca
 651  gtccattgag ctggggtgg gggtgggaca ggcacctcag agccacctgg
 701  agctgagagg gtactgaagg gaaaggacaa gggggaggga cagcagcaga
 751  ggggaattgc agagcccagc tggagaagaa gggtagctgg ggctcctcaa
 801  aaggtacagg ggagccaaag agggaaaagg ctcaacactg agacgggctc
 851  cccagtgcag gtcagagggg ccatgagggc aggcggggtg gtctgctcca
 901  ggaccccacc ttcccctgc cttcacaaga cagagggggg tatcaagagc
 951  caggagggta ccaggtcccc agctcagccc taggctgtgc tcacttcagg
1001  gtcaccctgc ccaaccttag aggaggtgag gggactccaa agtttttgat
1051  gatgccccca ctcggtgagg ccccttcaaa gtgccatctg tttacttctc
1101  aaatgaaaaa gaattcaggt ctgagtgtcc aggaaagggg gtgaatttca
1151  taaccgcctg tgacagcgat gggaaggagc cacacccctc cagagggtac
1201  cacccagcgg acaagtgggg aggaggaagt agctggcatg aagccggccc
1251  acccaacctc cgggagagag gaaaaggaga acacgggatg aggaggcttt
1301  aaatagtatt tcataaaata aaaatgccca gcactcttag gaacctctca
```

-continued

```
1351  ttcaaccgcc tagttttgt ttaaataatt ctaatgccag aggctggggg
1401  gcaggggcg gccagggtat gtacatgagg aggtgtttaa attaaaacac
1451  aaataataat taagacacac aaactgagac taaggcagaa gatgtagagc
1501  gggcctttga ggccctcgcg cttccaggac tgcaggcttc ctgtgggcgg
1551  attagggctt cctcttggag aagatcagcc ggcgtttgga gtggtagaaa
1601  tctgtcatgc tggtctgccg ccgttttcga ccctgagagt ctccaggtcc
1651  acctggggac ccttcagcct gctccctga gcgaggcaca agggtacaag
1701  acagtgacag gtccacatgg tcttcctctg ctgtcccctg cagcagagca
1751  ggtgaggtgc caggccgcct gcctcctccc aactcatccc ggcctcgccg
1801  gggccccgtg ggaaggtaga gcttgggcag gccaaggccc cgcacacgct
1851  cccaggcgaa gtcaccctcc agtggtgtct cggtgacaaa gtcgaagttc
1901  catcgctcac gggcctcctg gatgcagccc gccattagcg catcacagtc
1951  gcggctcagc tgctcgctgt ccactgggcc gaagaggcgg cggcaggcct
2001  tgctgccgca tgggttctga cggacatccc cagccggttc tgacatggcg
2051  cctgccgcag aaacacctgt gaacgcagca cacccgcg aacacgcatc
2101  ctcgcggaca cgcagggaca cacgcgggca cgcttggctc ggctctgggc
2151  cgccggcccg gggtcccctg ttgtctgccg ccgctctctc acctcctctg
2201  agtgcctcgg tgcctcggcg aatccgcgcc cagctccggc tccacaagga
2251  actgacttcg gcagc
```

The murine p21 sequence is provided below:

```
SEQ ID NO. 5:
  1   gagccgagag gtgtgagccg ccgcggtgtc agagtctagg ggaattggag
 51   tcaggcgcag atccacagcg atatccagac attcagagcc acaggcacca
101   tgtccaatcc tggtgatgtc cgacctgttc cgcacaggag caaagtgtgc
151   cgttgtctct tcggtcccgt ggacagtgag cagttgcgcc gtgattgcga
201   tgcgctcatg gcgggctgtc tccaggaggc ccgagaacg tggaactttg
251   acttcgtcac ggagacgccc ctgagggca acttcgtctg ggagcgcgtt
301   cggagcctag ggctgcccaa ggtctacctg agccctgggt ccgcagccg
351   tgacgacctg ggaggggaca agaggcccag tacttcctct gccctgctgc
401   aggggccagc tccggaggac cacgtggcct tgtcgctgtc ttgcactctg
451   gtgtctgagc ggcctgaaga ttccccgggt gggcccggaa catctcaggg
501   ccgaaaacgg aggcagacca gcctgacaga tttctatcac tccaagcgca
551   gattggtctt ctgcaagaga aaaccctgaa gtgcccacgg gagccccgcc
601   ctcttctgct gtgggtcagg aggcctcttc cccatcttcg gccttagccc
651   tcactctgtg tgtcttaatt attatttgtg ttttaattta aacgtctcct
701   gtatatacgc tgcctgccct ctcccagtct ccaaacttaa agttatttaa
751   aaaagaaca aaacaaaaca aaaaaaaacc aaaacaaaac aaacctaaat
801   tagtaggacg gtagggccct tagtgtgggg gatttctatt atgtagatta
851   ttattattta agccctccc aacccaagct ctgtgtttcc tataccggag
901   gaacagtcct actgatatca acccatctgc atccgtttca cccaaccccc
```

-continued

```
 951  ctcccccat tccctgcctg gttccttgcc acttcttacc tggggtgat
1001  cctcagacct gaatagcact ttggaaaaat gagtaggact ttggggtctc
1051  cttgtcacct ctaaggccag ctaggatgac agtgaagcag tcacagccta
1101  gaacagggat ggcagttagg actcaaccgt aatatcccga ctcttgacat
1151  tgctcagacc tgtgaagaca ggaatggtcc ccactctgga tccccttttgc
1201  cactcctggg gagcccacct ctcctgtggg tctctgccag ctgcccctct
1251  attttggagg gttaatctgg tgatctgctg ctcttttccc ccaccccata
1301  cttccccttc tgcaggtcgg caggaggcat atctaggcac ttgccccaca
1351  gctcagtgga ctggaaggga atgtatatgc agggtacact aagtgggatt
1401  ccctggtctt accttaggca gctccagtgg caaccccctg cattgtgggt
1451  ctagggtggg tccttggtgg tgagacaggc ctcccagagc attctatggt
1501  gtgtggtggt gggggtgggc ttatctggga tggggacccc agttgggttt
1551  ctcagtgact tctcccattt cttagtagca gttgtacaag gagccaggcc
1601  aagatggtgt cttgggggct aagggagctc acaggacact gagcaatggc
1651  tgatccttc tcagtgttga ataccgtggg tgtcaaagca cttagtgggt
1701  ctgactccag ccccaaacat ccctgtttct gtaacatcct ggtctggact
1751  gtctaccctt agcccgcacc caagaacat gtattgtggc tccctccctg
1801  tctccactca gattgtaagc gtctcacgag aagggacagc accctgcatt
1851  gtcccgagtc ctcacacccg accccaaagc tggtgctcaa taaatacttc
1901  tcgatgatt
```

The antisense murine p21 sequence is provided below:

```
SEQ ID NO. 6:
   1  aatcatcgag aagtatttat tgagcaccag ctttgggggtc gggtgtgagg
  51  actcgggaca atgcagggtg ctgtcccttc tcgtgagacg cttacaatct
 101  gagtggagac agggagggag ccacaataca tgttcttggg gtgcgggcta
 151  agggtagaca gtccagacca ggatgttaca gaaacaggga tgtttgggc
 201  tggagtcaga cccactaagt gctttgacac ccacggtatt caacactgag
 251  aaaggatcag ccattgctca gtgtcctgtg agctccctta gccccaaga
 301  caccatcttg gcctggctcc ttgtacaact gctactaaga aatgggagaa
 351  gtcactgaga accccaactg gggtccccat cccagataag cccaccccca
 401  ccaccacaca ccatagaatg tctgggagg cctgtctcac caccaaggac
 451  ccaccctaga cccacaatgc aggggggttgc cactggagct gcctaaggta
 501  agaccaggga atcccactta gtgtaccctg catatacatt cccttccagt
 551  ccactgagct gtggggcaag tgcctagata tgcctcctgc cgacctgcag
 601  aaggggaagt atggggtggg ggaaaagagc agcagatcac cagattaacc
 651  ctccaaaata gaggggcagc tggcagagac ccacaggaga ggtgggctcc
 701  ccaggagtgg caaaggggat ccagagtggg gaccattcct gtcttcacag
 751  gtctgagcaa tgtcaagagt cgggatatta cggttgagtc ctaactgcca
 801  tccctgttct aggctgtgac tgcttcactg tcatcctagc tggccttaga
 851  ggtgacaagg agaccccaaa gtcctactca ttttttccaaa gtgctattca
```

```
 901   ggtctgagga  tcacccccag  gtaagaagtg  gcaaggaacc  aggcagggaa 951   tggggggagg  ggggttgggt  gaaacggatg  cagatgggtt  gatatcagta 1001   ggactgttcc  tccggtatag  gaaacacaga  gcttgggttg  ggaggggctt 1051   aaataataat  aatctacata  atagaaatcc  cccacactaa  gggccctacc 1101   gtcctactaa  tttaggtttg  ttttgttttg  gttttttttt  gttttgtttt 1151   gttcttttt   taaataactt  taagtttgga  gactgggaga  gggcaggcag 1201   cgtatataca  ggagacgttt  aaattaaaac  acaaataata  attaagacac 1251   acagagtgag  ggctaaggcc  gaagatgggg  aagaggcctc  ctgacccaca 1301   gcagaagagg  gcggggctcc  cgtgggcact  tcagggtttt  ctcttgcaga 1351   agaccaatct  gcgcttggag  tgatagaaat  ctgtcaggct  ggtctgcctc

1401   cgttttcggc  cctgagatgt  tccgggccca  cccggggaat  cttcaggccg 1451   ctcagacacc  agagtgcaag  acagcgacaa  ggccacgtgg  tcctccggag 1501   ctggcccctg  cagcagggca  gaggaagtac  tgggcctctt  gtccctccc 1551   aggtcgtcac  ggctgcggga  cccagggctc  aggtagacct  tgggcagccc 1601   taggctccga  acgcgctccc  agacgaagtt  gccctccagc  ggcgtctccg 1651   tgacgaagtc  aaagttccac  cgttctcggg  cctcctggag  acagcccgcc 1701   atgagcgcat  cgcaatcacg  gcgcaactgc  tcactgtcca  cgggaccgaa 1751   gagacaacgg  cacactttgc  tcctgtgcgg  aacaggtcgg  acatcaccag

1801   gattggacat  ggtgcctgtg  gctctgaatg  tctggatatc  gctgtggatc 1851   tgcgcctgac  tccaattccc  ctagactctg  acaccgcggc  ggctcacacc 1901   tctcggctc
```

Of particular interest are antisense oligonucleotides that have a nucleotide sequence of 10, and more preferably 20, nucleotides within the sequence 1751-1850 or 1351-1450 of SEQ ID NO.:6, or of variants or fragments thereof that possess the ability to inhibit p21 expression and/or HIV replication or transmission. Such variants include oligonucleotides that are complementary to a corresponding region of the human p21 gene, or to non-human homologs as well as oligonucleotides that are composed of at least 10 of the nucleotide residues of 1751-1850 or 1351-1450 of SEQ ID NO.: 6. As an example, SEQ ID NO.:7: 5'-TGTCAGGCTGGTCT-GCCTCC-3', is an antisense oligonucleotide of SEQ ID NO.: 6 (shown underlined in SEQ ID NO.: 6) that possesses the ability to inhibit p21 expression and/or HIV replication or transmission. An example of a variant of this sequence is the corresponding sequence of the human p21 antisense sequence: SEQ ID NO. 8: TGTCATGC TGGTCTGCCG CC, shown underlined in SEQ ID NO.:4).

As a further example, the antisense oligonucleotide, SEQ ID NO:9: 5'-ACATCACCAGGATTGGACAT-3', is fragment of SEQ ID NO.: 6 (shown double underlined in SEQ ID NO.: 6) that possesses the ability to inhibit human p21 expression and/or HIV replication or transmission. An example of a variant of this sequence is the corresponding sequence of the human p21 antisense sequence: SEQ ID NO. 10: ACATC-CCCAGCCGGTTCTGACAT, shown double underlined in SEQ ID NO.:4).

Additional examples of preferred p21 inhibitors of the present invention include polynucleotide fragments of SEQ ID NO.: 11 (the antisense complement of the promoter region of the p21 gene (SEQ ID NO.:12)) or allelic or non-human species variants thereof, as well as promoter blockers, and other transcriptional or translational repressors of the p21 gene.

```
                                                        SEQ ID NO.: 11
  1   accatcccct  tcctcacctg  aaaacaggca  gcccaaggac  aaaatagcca 51   ccagcctctt  ctatgccaga  gctcaacatg  ttgggacatg  ttcctgacgg 101   ccagaaagcc  aatcagagcc  acagcctgct  gcccaagcat  gttcctggga 151   agcaggcagc  ataggggatgg  agggaggctc  agcctggggg  aacaagagtg 201   cc
```

```
                                                         SEQ ID NO.: 12
  1  ggcactcttg  ttccccagg  ctgagcctcc  ctccatccct  atgctgcctg 51  cttcccagga  acatgcttgg  gcagcaggct  gtggctctga  ttggctttct 101  ggccgtcagg  aacatgtccc  aacatgttga  gctctggcat  agaagaggct 151  ggtggctatt  ttgtccttgg  gctgcctgtt  ttcaggtgag  gaaggggatg 201  gt
```

Additional examples of preferred p21 inhibitors of the present invention include protein and other non-polynucleotide inhibitors of transcription, translation of the p21 gene, inhibitory p21 mimetics, or inhibitors of the transport or processing of the expressed p21 gene product (SEQ ID NO.: 13).

```
SEQ ID NO.: 13:
  1  MSEPAGDVRQ  NPCGSKACRR  LFGPVDSEQL  SRDCDALMAG  CIQEARERWN

51  FDFVTETPLE  GDFAWERVRG  LGLPKLYLPT  GPRRGRDELG  GGRRPGTSPA

101  LLQGTAEEDH  VDLSLSCTLV  PRSGEQAEGS  PGGPGDSQGR  KRRQTSMTDF

151  YHSKRRLIFS
```

Preferred inhibitors thus include triterpenoids, especially oleanane triterpenoids, and particularly the oleanane triterpenoid 2-cyano-3,12-dioxoolean-1,9-dien-28-oic acid (CDDO), and analogs thereof (see, for example, Stadheim, T. A. et al. (2002) "THE NOVEL TRITERPENOID 2-CYANO-3,12-DIOXOOLEANA-1,9-DIEN-28-OIC ACID (CDDO) POTENTLY ENHANCES APOPTOSIS INDUCED BY TUMOR NECROSIS FACTOR IN HUMAN LEUKEMIA CELLS," J Biol. Chem. 277:16448-16455; Suh, N. et al. (1999) "A NOVEL SYNTHETIC OLEANANE TRITERPENOID, 2-CYANO-3,12-DIOXOOLEAN-1,9-DIEN-28-OIC ACID, WITH POTENT DIFFERENTIATING, ANTIPROLIFERATIVE, AND ANTI-INFLAMMATORY ACTIVITY," Cancer Res. 59:336-341). Also suitable are derivatives and salts of such compounds, for example, 1[2-cyano-3,12-dioxoolean-1,9(11)-dien-28-oyl]imidazole (CDDO-Im) (Place, W. A. et al. (2003) "The Novel Synthetic Triterpenoid, CDDO-Imidazolide, Inhibits Inflammatory Response and Tumor Growth in Vivo," Clinical Cancer Research 9:2798-2806).

Molecules that inhibit or otherwise interfere with p21 function include binding ligands of p21 protein, including antibodies, or fragments thereof that bind to p21 protein. Suitable antibodies may be derived from human antisera, from non-human mammalian origin, or may be monoclonal, recombinant, single-chain, or humanized. Antigen-binding fragments of such antibodies (e.g., Fab and F(ab)$_2$ fragments) may alternatively be employed. If desired, such administration can be provided in concert with other p21 inhibitors.

Compositions of the Present Invention

In one embodiment of the present invention, non-polynucleotide p21 inhibitors may be employed. Alternatively, or conjunctively, one or more of the above-described p21 inhibitor molecules will comprise a polynucleotide or polynucleotide construct that may be administered to a recipient prior to the commencement of HIV infection, or subsequent to the onset of such infection. In accordance with the methods of the present invention, a single polynucleotide, polynucleotide construct, or composition comprising a polynucleotide or polynucleotide construct containing more than one polynucleotide sequence encoding one or more molecules may be administered. Alternatively, more than one polynucleotide, polynucleotide construct, or composition comprising a polynucleotide or polynucleotide construct, each containing polynucleotide sequences encoding one or more molecules may be co-administered or sequentially administered.

The p21 inhibitor compound(s) of the present invention may be provided to recipients using the principles of genetic therapy or as pharmaceutical compositions.

In accordance with the principles of genetic therapy, the compositions of the present invention will comprise one or more nucleic acid molecules (preferably DNA molecule(s)) that encode p21-inhibitor compound(s). Preferably, such nucleic acid molecules will be incorporated into a recombinant expression vector such as a chimeric virus, a plasmid DNA, etc., and will optionally be operatively linked to one or more regulatory elements (promoters, translation initiation sites, etc.) so as to permit the transcription of the nucleic acid molecule in a recipient cell. The promoter may be a cell-specific promoter that directs substantial transcription of the DNA only in predetermined cells. Highly efficient transcription can be achieved with the early and late promoters from SV40, the long terminal repeats (LTRS) from retroviruses, e.g., RSV, HTLVI, HIVI, MPSV and the immediate early promoter of the cytomegalovirus (CMV IEP). Alternatively, the administered nucleic acid molecules will not contain such regulatory elements, and will require cellular processes (such as recombination, integration into nuclear or mitochondrial DNA, etc.) in order to produce RNA transcripts.

Suitable DNA virus genomes include herpesvirus genomes, adenovirus genomes, adeno-associated virus genomes, and poxvirus genomes. However, cellular elements can also be used (e.g., the human actin promoter, metallothionein promoter). In humans, CMV IEP is preferred. Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109), VR1051, VR1055, and pcDNA3 (Invitrogen, San Diego, Calif.). In a preferred embodiment, such cytomegalovirus (CMV)-derived vectors, such as VRC8100, VRC 8103, VRC8106, VRC 8107, or VRC8108 are employed. All forms of DNA, whether replicating or non-replicating, preferably which do not become integrated into the genome, and which are expressible, are within the methods and compositions contemplated by the invention.

In one embodiment, a polynucleotide or polynucleotide construct of the present invention is RNA. Preferably in this embodiment, the RNA is in the form of messenger RNA (mRNA). Methods for introducing RNA sequences into vertebrate cells is described in U.S. Pat. No. 5,580,859. Alternatively, the RNA may be in the form of an RNA virus genome. Preferably an RNA virus genome of the present invention is noninfectious, (i.e., does not result in the production of infectious virus particles in vertebrate cells). Suitable RNA virus genomes include, but are not limited to, alphavirus genomes, picornavirus genomes, and retrovirus genomes. Methods for the in vivo introduction of non-infectious viral genomes to vertebrate tissues are well known to those of ordinary skill in the art and are described, e.g., in Altman-Hamamdzic, S., et al. (1997) "EXPRESSION OF BETA-GALACTOSIDASE IN MOUSE BRAIN: UTILIZATION OF A NOVEL NONREPLICATIVE SINDBIS VIRUS VECTOR AS A NEURONAL GENE DELIVERY SYSTEM," Gene Therapy 4:815-822, in U.S. Pat. No. 4,980,289, and in Miller, A. D., et al. 1993) "USE OF RETROVIRAL VECTORS FOR GENE TRANSFER AND EXPRESSION," Meth. Enzymol. 217:581-599. Viral replicons, i.e., non-infectious RNA virus genomes packaged in a viral coat, e.g., a picornavirus coat or an alphavirus coat, are also useful for efficient administration of RNA. See, e.g., U.S. Pat. Nos. 5,766,602; 5,614,413, and PCT Publication No. WO 95/07994.

The nucleic acid molecules of such compositions may be single stranded or double-stranded, and may be circular or linear. The term "nucleic acid" is intended to encompass a singular nucleic acid molecule as well as plural nucleic acid molecules, and to refer to an isolated molecule or construct, e.g., virus genomes (preferably non-infectious), messenger RNA (mRNA), plasmid DNA (pDNA), or derivatives of pDNA (e.g., minicircles as described in (Darquet, A-M et al. (1997) "A NEW DNA VEHICLE FOR NONVIRAL GENE DELIVERY: SUPERCOILED MINICIRCLE," Gene Therapy 4:1341-1349) comprising a polynucleotide or polynucleotide construct. A nucleic acid may be provided in linear (e.g., mRNA), circular (e.g., plasmid), or branched form as well as double-stranded or single-stranded forms. A nucleic acid may comprise a conventional phosphodiester bond or a non-conventional bond (e.g., an amide bond, such as found in peptide nucleic acids (PNA)). Preferably, a polynucleotide or polynucleotide construct of the present invention is part of a circular or linearized plasmid which is preferably non-infectious (i.e., does not result in the production of infectious virus particles in vertebrate cells), and nonintegrating (i.e., does not integrate into the genome of vertebrate cells). A linearized plasmid is a plasmid that was previously circular but has been linearized, for example, by digestion with a restriction endonuclease.

Methods of gene therapy are reviewed by Relph, K. et al. (2004) "RECENT DEVELOPMENTS AND CURRENT STATUS OF GENE THERAPY USING VIRAL VECTORS IN THE UNITED KINGDOM," BMJ. 329(7470):839-842; Takimoto, R. et al. (2004) "TUMOR SUPPRESSOR GENE p53 AND MOLECULAR TARGETING THERAPY," Gan To Kagaku Ryoho 31(9):1309-1313; Hannon, G. J. et al. (2004) "UNLOCKING THE POTENTIAL OF THE HUMAN GENOME WITH RNA INTERFERENCE," Nature 431(7006):371-378; Seufert, J. (2004) "CELL THERAPY AND GENE THERAPY IN DIABETES MELLITUS," MMW Fortschr Med. 146(20):39-40; Kawakami, Y. et al. (2004) "Cancer gene therapy and immunotherapy," Cancer Chemother Biol Response Modif. 21:327-337; Segota, E. et al. (2004) "THE PROMISE OF TARGETED THERAPY: CANCER DRUGS BECOME MORE SPECIFIC," Cleve Clin J. Med. 71(7):551-560; Morral, N. (2004) "GENE THERAPY FOR TYPE 1 DIABETES. NEW APPROACHES," Minerva Med. 95(2):93-104; Shen, W. G. (2004) "RNA INTERFERENCE AND ITS CURRENT APPLICATION IN MAMMALS," Chin Med J (Engl). 117(7): 1084-1091; Nicklin, S. A. et al. (2003) "DEVELOPMENT OF TARGETED VIRAL VECTORS FOR CARDIOVASCULAR GENE THERAPY," Genet Eng (N Y). 25:15-49; Davidoff, A. M. et al. (2004) "ANTIANGIOGENIC GENE THERAPY FOR CANCER TREATMENT," Curr Hematol Rep. 2004 3(4):267-273; Yonemitsu, Y. et al. (2004) "GENE THERAPY: ITS HISTORY, CURRENT STATUS, AND FUTURE PERSPECTIVES," Fukuoka Igaku Zasshi. 95(4):81-88; Donahue, J. K. et al. (2004) "GENE TRANSFER TECHNIQUES FOR CARDIAC ARRHYTHMIAS," Ann Med. 36 Suppl 1:98-105; Guo, Z. S. et al. (2004) "VACCINIA AS A VECTOR FOR GENE DELIVERY," Expert Opin Biol Ther. 4(6):901-917; Truckenmiller, M. E. et al. (2004) "VIRAL VECTORS FOR INDUCING CD8+ T CELL RESPONSES," Expert Opin Biol Ther. 4(6):861-868; Wang, S. et al. (2004) "THE p53 PATHWAY: TARGETS FOR THE DEVELOPMENT OF NOVEL CANCER THERAPEUTICS," Cancer Treat Res. 119:175-187; Downward, J. (2004) "RNA INTERFERENCE," BMJ. 328(7450):1245-1248; Scanlon, K. J. (2004) "CANCER GENE THERAPY: CHALLENGES AND OPPORTUNITIES," Anticancer Res. 24(2A):501-504; Ozawa, K. (2004) "AAV VECTOR-MEDIATED GENE TRANSFER AND ITS APPLICATION TO THE NERVOUS SYSTEM," Rinsho Shinkeigaku. 43(11):835-838; and Kanerva, A. et al. (2004) "MODIFIED ADENOVIRUSES FOR CANCER GENE THERAPY," Int J Cancer. 2004 Jul. 1; 110(4):475-480. Additional descriptions of gene therapy approaches that can be modified to accomplish the goals of the present invention are described in U.S. Pat. Nos. 6,806,080; 6,800,479; 6,797,703; 6,797,505; 6,784,162; 6,783,980; 6,780,639; 6,746,441; 6,743,620; 6,743,444; 6,740,331; 6,697,669; 6,692,966; 6,692,737; 6,689,758; 6,689,600; 6,677,313; 6,669,935; 6,667,294; 6,645,942; 6,632,670; 6,627,615; 6,592,864; 6,579,855; and 6,576,463.

If the p21 inhibitor compound(s) of the present invention is/are administered as a pharmaceutical composition, such pharmaceutical composition can be formulated according to known methods for preparing pharmaceutical compositions, whereby the substance to be delivered is combined with a pharmaceutically acceptable carrier vehicle. Suitable vehicles and their preparation are described, for example, in Remington's Pharmaceutical Sciences, 16$^{th}$ Edition, A. Osol, Ed., Mack Publishing Co., Easton, Pa. (1980), and Remington's Pharmaceutical Sciences, 19th Edition, A. R. Gennaro, Ed., Mack Publishing Co., Easton, Pa. (1995).

The amount of a polynucleotide or polynucleotide construct or other p21 inhibitor included in such a composition depends on factors including the age and weight of the subject, the delivery method and route, the type of treatment desired, and the type of polynucleotide or polynucleotide construct or other p21 inhibitor being administered. In general, a composition of the present invention that includes polynucleotide or polynucleotide constructs will contain from about 1 ng to about 30 mg of such polynucleotide or polynucleotide construct, more preferably, from about 100 ng to about 10 mg of such polynucleotide or polynucleotide construct. Certain preferred compositions of the present invention may include about 1 ng of such polynucleotide or polynucleotide construct, about 5 ng of such polynucleotide or polynucleotide construct, about 10 ng of such polynucleotide or polynucleotide construct, about 50 ng of such polynucleotide or polynucleotide construct, about 100 ng of such polynucleotide or polynucleotide construct, about 500 ng of such polynucleotide or polynucleotide construct, about 1 µg of such polynucleotide or polynucleotide construct, about 5 µg of such polynucleotide or polynucleotide construct, about 10 µg of such polynucleotide or polynucleotide construct, about 50 µg of such polynucleotide or polynucleotide construct, about 100 µg of such polynucleotide or polynucleotide construct, about 150 µg of such polynucleotide or polynucleotide construct, about 200 µg of such polynucleotide or polynucleotide construct, about 250 µg of such polynucleotide or polynucleotide construct, about 300 µg of such polynucleotide or polynucleotide construct, about 350 µg of such polynucleotide or polynucleotide construct, about 400 µg of such polynucleotide or polynucleotide construct, about 450 µg of such polynucleotide or polynucleotide construct, about 500 µg of a polynucleotide, about 550 µg of such polynucleotide or polynucleotide construct, about 600 µg of such polynucleotide or polynucleotide construct, about 650 µg of such polynucleotide or polynucleotide construct, about 700 µg of such polynucleotide or polynucleotide construct, about 750 µg of such polynucleotide or polynucleotide construct, about 800 µg of such polynucleotide or polynucleotide construct, about 850 µg of a polynucleotide, about 900 µg of such polynucleotide or polynucleotide construct, about 950 µg of such polynucleotide or polynucleotide construct, about 1 mg of such polynucleotide or polynucleotide construct, about 5 mg of such polynucleotide or polynucleotide construct, about 10 mg of such polynucleotide or polynucleotide construct, about 15 mg of such polynucleotide or polynucleotide construct, about 20 mg of such polynucleotide or polynucleotide construct, about 25 mg of such polynucleotide or polynucleotide construct, or about 30 mg of such polynucleotide or polynucleotide construct.

Nucleic acids and/or polynucleotides and/or polynucleotide constructs of the present invention, e.g., plasmid DNA, derivatives of plasmid DNA, mRNA, linear DNA, viral genomes, or polynucleotide fragments contained therein may be formulated into any of the various compositions and may be used in any of the methods disclosed herein. As used herein, the term "polynucleotide fragment" refers to a polynucleotide that is either a portion of a gene, cDNA or RNA molecule, or a complement of such molecules, and which possesses a length of at least 10 nucleotide residues, at least 15 nucleotide residues, at least 20 nucleotide residues, at least 25 nucleotide residues, at least 35 nucleotide residues, at least 50 nucleotide residues, at least 75 nucleotide residues, at least at least 100 nucleotide residues, at least 150 nucleotide residues, or at least 200 nucleotide residues.

For aqueous compositions used in vivo, use of sterile pyrogen-free water is preferred. Such formulations will contain an effective amount of such polynucleotide or polynucleotide construct together with a suitable salt and/or auxiliary agent as disclosed herein, in order to prepare pharmaceutically acceptable compositions suitable for optimal administration to a vertebrate. Insoluble polynucleotides or polynucleotide constructs may be solubilized in a weak acid or weak base, and then diluted to the desired volume, for example, with an aqueous solution of the present invention. The pH of the solution may be adjusted as appropriate. In addition, a pharmaceutically acceptable additive can be used to provide an appropriate osmolarity.

As used herein a "salt" is a substance produced from the reaction between acids and bases which comprises a metal (cation) and a nonmetal (anion). Salt crystals may be "hydrated" i.e., contain one or more water molecules. Such hydrated salts, when dissolved in an aqueous solution at a certain molar concentration, are equivalent to the corresponding anhydrous salt dissolved in an aqueous solution at the same molar concentration. For the present invention, salts which are readily soluble in an aqueous solution are preferred.

The terms "saline" or "normal saline" as used herein refer to an aqueous solution of about 145 mM to about 155 mM sodium chloride, preferably about 154 mM sodium chloride. The terms "phosphate buffered saline" or PBS" refer to an aqueous solution of about 145 mM to about 15:5 mM sodium chloride, preferably about 154 mM sodium chloride, and about 10 mM sodium phosphate, at a pH ranging from about 6.0 to 8.0, preferably at a pH ranging from about 6.5 to about 7.5, most preferably at pH 7.2.

Such compositions of the present invention may include one or more transfection facilitating materials that facilitate delivery of polynucleotides or polynucleotide constructs to the interior of a cell, and/or to a desired location within a cell. Examples of the transfection facilitating materials include, but are not limited to lipids, preferably cationic lipids; inorganic materials such as calcium phosphate, and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e. helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogenous" poly-amino acids (e.g., mixtures of lysine & glycine), co-polymers, polyvinylpyrrolidinone (PVP), and polyethylene glycol (PEG). Furthermore, those auxiliary agents of the present invention which facilitate and enhance the entry of a polynucleotide or polynucleotide construct into vertebrate cells in vivo, may also be considered "transfection facilitating materials."

Certain embodiments of the present invention may include lipids as a transfection facilitating material, including cationic lipids (e.g., DMRIE, DOSPA, DC-Chol, GAP-DLRIE), basic lipids (e.g., steryl amine), neutral lipids (e.g., cholesterol), anionic lipids (e.g., phosphatidyl serine), and zwitterionic lipids (e.g., DOPE, DOPC).

Examples of cationic lipids are 5-carboxyspermylglycine dioctadecylamide (DOGS) and dipalmitoyl-phophatidylethanolamine-5-carboxy-spermylamide (DPPES). Cationic cholesterol derivatives are also useful, including {3β-[N-N', N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (ADEMO), N-(3-aminopropyl)-N,N-(bis-(2-dodecyloxyethyl))-N-methyl-1-ammonium bromide (PADELO), N,N,N-tris-(2-dodecyloxy)ethyl-N-(3-amino)pro-pyl-ammonium bromide (PATELO), and $N_1$-(3-aminopropyl)((2-dodecyloxy)e-thyl)-$N_2$-(2-dodecyloxy)ethyl-1-piperazinaminium bromide (GALOE-BP) can also be employed in the present invention.

Non-diether cationic lipids, such as DL-1,2-dioleoyl-3-dimethylamin-opropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. Preferred cationic lipids comprise groups attached via a heteroatom attached to the quaternary ammonium moiety in the head group. A glycyl spacer can connect the linker to the hydroxyl group.

Cationic lipids for use in certain embodiments of the present invention include DMRIE ((±)-N-(2-hydroxyethyl)-N,N-dimethyl-2-,3-bis(tetradecyloxy)-1-propanaminium bromide), and GAP-DMORIE ((+)-N-(3-aminopropyl)-N,N-dimethyl-2,3-bis(syn-9-tetradeceneyloxy)-1-pro-panaminium bromide), as well as (±)-N,N-dimethyl-N-[2-(sperminecarboxamido)et-hyl]-2,3-bis(dioleyloxy)-1-propaniminium pentahydrochloride (DOSPA), (±)-N-(2-aminoethyl)-N,N-dimethyl-2,3-bis(tetradecyloxy)-1-propanimini-um bromide (β-aminoethyl-DMRIE or βAE-DMRIE) (Wheeler, et al., Biochim. Biophys. Acta 1280:1-11 (1996)), and (±)-N-(3-aminopropyl)-N,-N-dimethyl-2,3-bis (dodecyloxy)-1-propaniminium bromide (GAP-DLRIE) (Wheeler, et al., Proc. Natl. Acad. Sci. USA 93:11454-11459

(1996)), which have been developed from DMRIE. Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,-N-dimethyl-2,3-(bis-tetradecyloxy)-1-propanaminium bromide (GAP-DMRIE), (O)-N-((N"-methyl)-N'-ureyl)propyl-N,N-dimethyl-2,3-bis(tetradecyloxy)-1-propanaminium bromide (GMU-DMRIE), (O)-N-(2-hydroxyethyl)-N,N-dimeth-yl-2,3-bis(dodecyloxy)-1-propanaminium bromide (DLRIE), and (±)-N-(2-hydroxyethyl)-N,N-dimethyl-2,3-bis-([Z]-9-octadecenyloxy)prop-yl-1-propaniminium bromide (HP-DORIE).

A cationic lipid that may be used in concert with the p21 inhibitor polynucleotide compositions of the present invention is a "cytofectin." As used herein, a "cytofectin" refers to a subset of cationic lipids which incorporate certain structural features including, but not limited to, a quaternary ammonium group and/or a hydrophobic region (usually with two or more alkyl chains), but which do not require amine protonation to develop a positive charge. Examples of cytofectins may be found, for example, in U.S. Pat. No. 5,861,397. Cytofectins that may be used in the present invention, include DMRIE ((±)-N-(2-hydroxyethyl)-N,N-dimethyl-2,3-bis(tetradecyloxy)-1-pr-opanaminium bromide), GAP-DMORIE ((±)-N-(3-aminopropyl)-N,N-dimethyl-2,-3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanami-um bromide).

The cationic lipid may be mixed with one or more co-lipids. The term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. A preferred class of co-lipids are the zwitterionic phospholipids, which include the phosphatidylethanolamines and the phosphatidylcholines. Most preferably, the co-lipids are phosphatidylethanolamines, such as, for example, DOPE, DMPE and DPyPE. DOPE and DPyPE are particularly preferred. The most preferred co-lipid is DPyPE, which comprises two phytanoyl substituents incorporated into the diacylphosphatidylethanolamine skeleton. The cationic lipid:co-lipid molar ratio may range from about 9:1 to about 1:9, or from about 4:1 to about 1:4, or from about 2:1 to about 1:2, or about 1:1. In order to maximize homogeneity, such cationic lipid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, plasmid DNA according to methods known to those skilled in the art. For example, the sonication of a lipid solution is described in Felgner, P. L., et al. (1987) "LIPOFECTION: A HIGHLY EFFICIENT, LIPID-MEDIATED DNA-TRANSFECTION PROCEDURE," Proc. Natl. Acad. Sci. USA 84:7413-7417 and in U.S. Pat. No. 5,264,618.

In some embodiments, such polynucleotide or polynucleotide construct(s) are combined with lipids by mixing, for example, a plasmid DNA solution and a solution of cationic lipid:co-lipid liposomes. Preferably, the concentration of each of the constituent solutions is adjusted prior to mixing such that the desired final plasmid DNA/cationic lipid:co-lipid ratio and the desired plasmid DNA final concentration will be obtained upon mixing the two solutions. For example, if the desired final solution is to be 2.5 mM sodium phosphate, the various components of the composition, e.g., plasmid DNA, cationic lipid:co-lipid liposomes, and any other desired auxiliary agents, transfection facilitating materials, or additives are each prepared in 2.5 mM sodium phosphate and then simply mixed to afford the desired complex. Alternatively, if the desired final solution is to be, e.g., 2.5 mM sodium phosphate, certain components of the composition, e.g., the auxiliary agent and/or cationic lipid:co-lipid liposomes, is prepared in a volume of water which is less than that of the final volume of the composition, and certain other components of the composition, e.g., the plasmid DNA, is prepared in a solution of sodium phosphate at a higher concentration than 2.5 mM, in a volume such that when the components in water are added to the components in the sodium phosphate solution, the final composition is in an aqueous solution of 2.5 mM sodium phosphate. For example, the plasmid DNA could be prepared in 5.0 mM sodium phosphate at one half the final volume, the auxiliary agent and/or cationic lipid:co-lipid liposome is prepared in water at one half the final volume, and then these two elements are mixed together to produce the final composition. The cationic lipid:co-lipid liposomes are preferably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

A transfection facilitating material can be used alone or in combination with one or more other transfection facilitating materials. Two or more transfection facilitating materials can be combined by chemical bonding (e.g, covalent and ionic such as in lipidated polylysine, PEGylated polylysine) (Toncheva, V., et al. (1998) "NOVEL VECTORS FOR GENE DELIVERY FORMED BY SELF-ASSEMBLY OF DNA WITH POLY(L-LYSINE) GRAFTED WITH HYDROPHILIC POLYMERS," Biochim. Biophys. Acta 1380(3):354-368), mechanical mixing (e.g., free moving materials in liquid or solid phase such as "polylysine+cationic lipids") (Gao, X. et al. (1996) "POTENTIATION OF CATIONIC LIPOSOME-MEDIATED GENE DELIVERY BY POLYCATIONS," Biochemistry 35:1027-1036); Trubetskoy, V. S., et al. (1992) "CATIONIC LIPOSOMES ENHANCE TARGETED DELIVERY AND EXPRESSION OF EXOGENOUS DNA MEDIATED BY N-TERMINAL MODIFIED POLY(L-LYSINE)-ANTIBODY CONJUGATE IN MOUSE LUNG ENDOTHELIAL CELLS," Biochem. Biophys. Acta 1131:311-313), and aggregation (e.g., co-precipitation, gel forming such as in cationic lipids+poly-lactide co-galactide, and polylysine+gelatin).

Other hydrophobic and amphiphilic additives, such as, for example, sterols, fatty acids, gangliosides, glycolipids, lipopeptides, liposaccharides, neobees, niosomes, prostaglandins and sphingolipids, may also be included in the compositions of the present invention. In such compositions, these additives may be included in an amount between about 0.1 mol % and about 99.9 mol % (relative to total lipid). Preferably, these additives comprise about 1-50 mol % and, most preferably, about 2-25 mol %. Preferred additives include lipopeptides, liposaccharides and steroids.

In embodiments of the present invention in which non-polynucleotide p21 inhibitors are provided, such compounds can be formulated according to known methods for preparing such pharmaceutical compositions, whereby the substance to be delivered is combined with a pharmaceutically acceptable carrier vehicle. Suitable vehicles and their preparation are described, for example, in Remington's Pharmaceutical Sciences, 16$^{th}$ Edition, A. Osol, Ed., Mack Publishing Co., Easton, Pa. (1980), and Remington's Pharmaceutical Sciences, 19$^{th}$ Edition, A. R. Gennaro, Ed., Mack Publishing Co., Easton, Pa. (1995). The amount of such compounds included in such a composition depends on factors including the age and weight of the subject, the delivery method and route, the type of treatment desired, and the type of polynucleotide or polynucleotide construct or other p21 inhibitor being administered. In general, a composition of the present invention that includes such inhibitors will contain from about 1 ng to about 30 mg, and more preferably, from about 100 ng to about 10 mg of such inhibitor. Certain preferred compositions of the present invention may include about 1 ng of such inhibitor, about 5 ng of such inhibitor, about 10 ng of such inhibitor, about 50 ng of such inhibitor, about 100 ng of such inhibitor, about 500 ng of such inhibitor, about 1 µg of such inhibitor, about 5 µg of such inhibitor, about 10 µg of such inhibitor, about 50 µg of such inhibitor, about 100 µg of such inhibitor, about 150 µg of such inhibitor, about 200 µg of such inhibitor, about 250 µg of such inhibitor, about 300 µg of such inhibitor, about 350 µg of such inhibitor, about 400 µg of such inhibitor, about 450 µg of such inhibitor, about 500 µg of a polynucleotide, about 550 µg of such inhibitor, about 600 µg of such inhibitor, about 650 µg of such inhibitor, about 700 µg of such inhibitor, about 750 µg of such inhibitor, about 800 µg of such inhibitor, about 850 µg of a polynucle-otide, about 900 µg of such inhibitor, about 950 µg of such inhibitor, about 1 mg of such inhibitor, about 5 mg of such inhibitor, about 10 mg of such inhibitor, about 15 mg of such inhibitor, about 20 mg of such inhibitor, about 25 mg of such inhibitor, or about 30 mg of such inhibitor.

Such compositions may be formulated into any of the various compositions and may be used in any of the methods disclosed herein. For aqueous compositions used in vivo, use of sterile pyrogen-free water is preferred. Such formulations will contain an effective amount of such inhibitor together with a suitable salt and/or auxiliary agent as disclosed herein, in order to prepare pharmaceutically acceptable compositions suitable for optimal administration to a vertebrate. Insoluble inhibitors may be solubilized in a weak acid or weak base, and then diluted to the desired volume, for example, with an aqueous solution of the present invention. The pH of the solution may be adjusted as appropriate. In addition, a pharmaceutically acceptable additive can be used to provide an appropriate osmolarity. Alternatively, lipids and lipid vehicles (as discussed above) may be used to facilitate the inhibitor administration. Other hydrophobic and amphiphilic additives, such as, for example, sterols, fatty acids, gangliosides, glycolipids, lipopeptides, liposaccharides, neobees, niosomes, prostaglandins and sphingolipids, may also be included in such compositions of the present invention. In such compositions, these additives may be included in an amount between about 0.1 mol % and about 99.9 mol % (relative to total lipid). Preferably, these additives comprise about 1-50 mol % and, most preferably, about 2-25 mol %. Preferred additives include lipopeptides, liposaccharides and steroids.

Pharmaceutical Compositions

The pharmaceutical composition of the present invention may be in the form of an emulsion, gel, solution, suspension, etc. In addition, the pharmaceutical composition can also contain pharmaceutically acceptable additives including, for example, diluents, binders, stabilizers, and preservatives. Administration of pharmaceutically acceptable salts of the polynucleotides described herein is preferred. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. Preferred salts include but are not limited to sodium phosphate, sodium acetate, sodium bicarbonate, sodium sulfate, sodium pyruvate, potassium phosphate, potassium acetate, potassium bicarbonate, potassium sulfate, potassium pyruvate, disodium DL-α-glycerol-phosphate, and disodium glucose-6-phosphate. "Phosphate" salts of sodium or potassium can be either the monobasic form, e.g., NaHPO$_4$, or the dibasic form, e.g., Na$_2$HPO$_4$, but a mixture of the two, resulting in a desired pH, is most preferred. The most preferred salts are sodium phosphate or potassium phosphate. As used herein, the terms "sodium phosphate" or "potassium phosphate," refer to a mixture of the dibasic and monobasic forms of each salt to present at a given pH.

Additional embodiments of the present invention are drawn to pharmaceutical compositions comprising one or more p21 inhibitor molecules and an auxiliary agent. The present invention is further drawn to methods to use such compositions, methods of making such compositions, and pharmaceutical kits. As used herein, an "auxiliary agent" is a substance included in a composition for its ability to enhance, relative to a composition which is identical except for the inclusion of the auxiliary agent, the effectiveness of a p21 inhibitor molecule. Auxiliary agents of the present invention include nonionic, anionic, cationic, or zwitterionic surfactant or detergents, with nonionic, anionic, cationic, or zwitterionic surfactant or detergents, with nonionic surfactant or detergents being preferred, chelators, DNAse inhibitors, agents that aggregate or condense nucleic acids, emulsifying or solubilizing agents, wetting agents, gel-forming agents, and buffers.

Suitable auxiliary agents include non-ionic detergents and surfactant such as poloxaners. Poloxamers are a series of non-ionic surfactant that are block copolymers of ethylene oxide and propylene oxide. The poly(oxyethylene) segment is hydrophillic and the poly(oxypropylene) segment is hydrophobic. The physical forms are liquids, pastes or solids. The molecular weight ranges from 1000 to greater than 16000. The basic structure of a poloxaner is HO—[CH$_2$CH$_2$O]$_x$—[CH$_2$CHO(CH$_3$)]$_y$—[CH$_2$CH$_2$O]$_x$—H, where x and y represent repeating units of ethylene oxide and propylene oxide respectively. Thus, the propylene oxide (PO) segment is sandwiched between two ethylene oxide (EO) segments, (EO-PO-EO). The number of x's and y's distinguishes individual poloxamers. If the ethylene oxide segment is sandwiched between two propylene oxide segments, (PO-EO-PO), then the resulting structure is a reverse poloxaner. The basic structure of a reverse poloxamer is HO—[CH(CH$_3$)CH$_2$O)]$_x$—[CH$_2$CH$_2$O]$_y$—[CH$_2$C—HO(CH$_3$)]$_x$—H.

Poloxamers that may be used in concert with the methods and compositions of the present invention include, but are not limited to commercially available poloxamers such as Pluronic® L121 (avg. MW:4400), Pluronic® L101 (avg. MW:3800), Pluronic® L81 (avg. MW:2750), Pluronic® L61 (avg. MW:2000), Pluronic® L31 (avg. MW: 1100), Pluronic® L122 (avg. MW:5000), Pluronic® L92 (avg.

MW:3650), Pluronic® L72 (avg. MW:2750), Pluronic® L62 (avg. MW:2500), Pluronic® L42 (avg. MW:1630), Pluronic® L63 (avg. MW:2650), Pluronic® L43 (avg. MW: 1850), Pluronic® L64 (avg. MW:2900), Pluronic® L44 (avg. MW:2200), Pluronic® L35 (avg. MW:1900), Pluronic® P123 (avg. MW:5750), Pluronic® P103 (avg. MW:4950), Pluronic® P104 (avg. MW:5900), Pluronic® P84 (avg. MW:4200), Pluronic® P105 (avg. MW:6500), Pluronic® P85 (avg. MW:4600), Pluronic® P75 (avg. MW:4150), Pluronic® P65 (avg. MW:3400), Pluronic® F127 (avg. MW: 12600), Pluronic® F98 (avg. MW: 13000), Pluronic® F87 (avg. MW:7700), Pluronic® F77 (avg. MW:6600), Pluronic® F 108 (avg. MW: 14600), Pluronic® F98 (avg. MW: 13000), Pluronic® F88 (avg. MW: 11400), Pluronic® F68 (avg. MW:8400), and Pluronic® F38 (avg. MW:4700).

Reverse poloxamers of the present invention include, but are not limited to Pluronic® R31R1 (avg. MW:3250), Pluronic® R 25R1 (avg. MW:2700), Pluronic® R17R1 (avg. MW:1900), Pluronic® R31R2 (avg. MW:3300), Pluronic® R25R2 (avg. MW:3100), Pluronic® R17R2 (avg. MW:2150), Pluronic® R12R3 (avg. MW: 1800), Pluronic® R31R4 (avg. MW:4150), Pluronic® R25R4 (avg. MW:3600), Pluronic® R22R4 (avg. MW:3350), Pluronic® R17R4 (avg. MW:3650), Pluronic® R25R5 (avg. MW:4320), Pluronic® R10R5 (avg. MW:1950), Pluronic® R25R8 (avg. MW:8850), Pluronic® R17R8 (avg. MW:7000), Pluronic® R10R8 (avg. MW:4550).

Other commercially available poloxamers include compounds that are block copolymer of polyethylene and polypropylene glycol such as Synperonic® L121, Synperonic® L122, Synperonic® P104, Synperonic® P105, Synperonic® P123, Synperonic® P85, and Synperonic® P94; and compounds that are nonylphenyl polyethylene glycol such as Synperonic® NP10, Synperonic® NP30, and Synperonic® NP5.

Suitable auxiliary agents include non-ionic detergents and surfactants such as Pluronic® F68, Pluronic® F77, Pluronic® F108, Pluronic® F127, Pluronic® P65, Pluronic® P85, Pluronic® P103, Pluronic® P104, Pluronic® P105, Pluronic® P123, Pluronic® L31, Pluronic® L43, Pluronic® L44, Pluronic® L61, Pluronic® L62, Pluronic® L64, Pluronic® L81, Pluronic® L92, Pluronic® L101, Pluronic® L121, Pluronic® R17R4, Pluronic® R25R4, Pluronic® R25R2, IGEPAL CA 630®, NONIDET NP-40, Nonidet® P40, Tween-20®, Tween-80®, Triton X-100®, Triton X-114™, Thesit®; the anionic detergent sodium dodecyl sulfate (SDS); the sugar stachyose; the condensing agent DMSO; and the chelator/DNAse inhibitor EDTA. Even more preferred are the auxiliary agents Nonidet® P40, Triton X-100®, Pluronic® F68, Pluronic® F77, Pluronic® F108, Pluronic® P65, Pluronic® P103, Pluronic® L31, Pluronic® L44, Pluronic® L61, Pluronic® L64, Pluronic® L92, Pluronic® R17R4, Pluronic® R25R4 and Pluronic® R25R2. Most preferred auxiliary agent is Pluronic® R25R2.

Optimal concentrations of auxiliary agents of the present invention are disclosed in U.S. Patent Application Publication No. 20020019358 and PCT Publication WO0180897A3. For example, in certain embodiments, pharmaceutical compositions of the present invention comprise about 5 ng to about 30 mg of a suitable polynucleotide or a polynucleotide construct, and/or a non-polynucleotide p21 inhibitor, and about 0.001% (w/v) to about 2.0% (w/v) of Pluronic® R 25R4, preferably about 0.002% (w/v) to about 1.0% (w/v) of Pluronic® R 25R4, more preferably about 0.01% (w/v) to about 0.01% (w/v) of Pluronic® R 25R4, with about 0.01% (w/v) of Pluronic® R 25R4 being the most preferred; about 0.001% (w/v) to about 2.0% (w/v) of Pluronic® R 25R2, preferably about 0.001% (w/v) to about 1.0% (w/v) of Pluronic®D R 25R2, more preferably about 0.001% (w/v) to about 0.1% (w/v) of Pluronic® R 25R2, with about 0.01% (w/v) of Pluronic® R 25R2 being the most preferred.

Administration of the Pharmaceutical Compositions of the Present Invention

The pharmaceutical compositions of the present invention may be administered by any suitable means, for example, inhalation, or intradermally, intracavity (e.g., oral, vaginal, rectal, nasal, peritoneal, ventricular, or intestinal), intradermally, intramuscularly, intranasally, intraocularly, intraperitoneally, intrarectally, intratracheally, intravenously, orally, subcutaneously, transdermally, or transmucosally (i.e., across a mucous membrane) in a dose effective for the production of neutralizing antibody and resulting in protection from infection or disease. The present pharmaceutical compositions can generally be administered in the form of a spray for intranasal administration, or by nose drops, inhalants, swabs on tonsils, or a capsule, liquid, suspension or elixirs for oral administration. The pharmaceutical compositions may be in the form of single dose preparations or in multi-dose flasks. Reference is made to Remington's Pharmaceutical Sciences, Mack Publishing Co., Easton, Pa., Osol (ed.) (1980).

Administration can be into one or more tissues including but not limited to muscle, skin, brain, lung, liver, spleen, bone marrow, thymus, heart, e.g., myocardium, endocardium, and pericardium; lymph nodes, blood, bone, cartilage, pancreas, kidney, gall bladder, stomach, intestine, testis, ovary, uterus, rectum, nervous system, eye, gland, or connective tissue. Furthermore, in the methods of the present invention, the pharmaceutical compositions may be administered to any internal cavity of a mammal, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, and the ocular cavities. Any mode of administration can be used so long as the mode results in prophylactic or therapeutic efficacy. Methods to detect such a response include serological methods, e.g., western blotting, molecular (transcriptional) staining tissue sections by immunohistochemical methods, and measuring the activity of the polypeptide. Pharmaceutical DNA compositions and methods of their manufacture and delivery that may be used in accordance with the present invention are disclosed in U.S. Pat. Nos. 5,589,466; 5,620,896; 5,641,665; 5,703,055; 5,707, 812; 5,846,946; 5,861,397; 5,891,718; 6,022,874; 6,147,055; 6,214,804; 6,228,844; 6,399,588; 6,413,942; 6,451,769, European Patent Documents EP1165140A2; EP1006796A1 and EP0929536A1; and PCT Patent Publications WO00/ 57917; WO00/3263; WO01/09303; WO03/028632; WO94/ 29469; WO95/29703; and WO98/14439.

Administration may be by needle injection, catheter infusion, biolistic injectors, particle accelerators (e.g., "gene guns" or pneumatic "needleless" injectors) Med-E-Jet (Vahlsing, H., et al. (1994) "IMMUNIZATION WITH PLASMID DNA USING A PNEUMATIC GUN," J. Immunol. Methods 171:11-22), Pigjet (Schrijver, R. S. et al. (1997) "IMMUNIZATION OF CATTLE WITH A BHV1 VECTOR VACCINE OR A DNA VACCINE BOTH CODING FOR THE G PROTEIN OF BRSV," Vaccine 15:1908-1916), Biojector (Davis, H. L. et al. (1994) "DIRECT GENE TRANSFER IN SKELETAL MUSCLE: PLASMID DNA-BASED IMMUNIZATION AGAINST THE HEPATITIS B VIRUS SURFACE ANTIGEN," Vaccine 12:1503-1509; Gramzinski, R., et al. (1998) "IMMUNE RESPONSE TO A HEPATITIS B DNA VACCINE IN AOTUS MONKEYS: A COMPARISON OF VACCINE FORMULATION, ROUTE, AND METHOD OF ADMINISTRATION," Mol Med 4:109-118), AdvantaJet (Lindmayer, I., et al. (1986)

"DEVELOPMENT OF NEW JET INJECTOR FOR INSULIN THERAPY," Diabetes Care 9:294-297), Medi-jector (Martins, J. K. et al. (1979) "MEDIJECTOR—A NEW METHOD OF CORTICOSTEROID-ANESTHETIC DELIVERY," J. Occup. Med. 21:821-824), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, J. Y. et al. (1999) "GENE SUTURE—A NOVEL METHOD FOR INTRAMUSCULAR GENE TRANSFER AND ITS APPLICATION IN HYPERTENSION THERAPY," Life Sciences 65:2193-2203) or topical applications during surgery.

Thus, in one embodiment, administration is into muscle tissue, i.e., skeletal muscle, smooth muscle, or myocardium. Most preferably, the muscle is skeletal muscle. For polynucleotide constructs in which the polynucleotide or polynucleotide construct is DNA, the DNA can be operably linked to a cell-specific promoter that directs substantial transcription of the DNA only in predetermined cells. In certain embodiments, a polynucleotide construct, or composition comprising an polynucleotide or polynucleotide construct, is delivered to any tissue including, but not limited to those disclosed herein, such that the polynucleotide or polynucleotide construct is free from association with liposomal formulations and charged lipids. Alternatively, the polynucleotide, polynucleotide construct, or composition is delivered to a tissue other than brain or nervous system tissue, for example, to muscle, skin, or blood, in any composition as described herein.

Preferably, the pharmaceutical composition is delivered to the interstitial space of a tissue. "Interstitial space" comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels.

Nucleic acid pharmaceutical compositions, preferably in the form of plasmid DNA, may be administered (especially by injection) into tissue and voltage pulses applied between electrodes disposed in the tissue, thus applying electric fields to cells of the tissue. The electrically-mediated enhancement covers administration using either iontophoresis or electroporation in vivo. Suitable techniques of electroporation and iontophoresis are provided by Singh, J. et al. (1989) "TRANSDERMAL DELIVERY OF DRUGS BY IONTOPHORESIS: A REVIEW," Drug Des. Deliv. 4:1-12; Theiss, U. et al. (1991) "IONTOPHORESIS—IS THERE A FUTURE FOR CLINICAL APPLICATION?," Methods Find. Exp. Clin. Pharmacol. 13:353-359; Singh and Maibach (1993) "TOPICAL IONTOPHORETIC DRUG DELIVERY IN VIVO: HISTORICAL DEVELOPMENT, DEVICES AND FUTURE PERSPECTIVES," Dermatology. 187:235-238; Singh, P. et al. (1994) "IONTOPHORESIS IN DRUG DELIVERY: BASIC PRINCIPLES AND APPLICATIONS," Crit. Rev. Ther. Drug Carrier Syst. 11:161-213; Su, Y. et al. (1994) "SPHINGOSINE 1-PHOSPHATE, A NOVEL SIGNALING MOLECULE, STIMULATES DNA BINDING ACTIVITY OF AP-1 IN QUIESCENT SWISS 3T3 FIBROBLASTS," J. Pharm. Sci. 83:12-17; Costello, C. T. et al. (1995) "IONTOPHORESIS: APPLICATIONS IN TRANSDERMAL MEDICATION DELIVERY," Phys. Ther. 75:554-563; Howard, J. p. et al. (1995) "EFFECTS OF ALTERNATING CURRENT IONTOPHORESIS ON DRUG DELIVERY," Arch. Phys. Med. Rehabil. 76:463-466; Kassan, D. G. et al. (1996) "PHYSICAL ENHANCEMENT OF DERMATOLOGIC DRUG DELIVERY: IONTOPHORESIS AND PHONOPHORESIS," J. Amer. Acad. Dermatol. 34:657-666; Riviere et al. (1997) "ELECTRICALLY-ASSISTED TRANSDERMAL DRUG DELIVERY," Pharm. Res. 14:687-697; Zempsky, W. T. et al. (1998) "IONTOPHORESIS: NONINVASIVE DRUG DELIVERY," Amer. J. Anesthesiol. 25:158-162; Muramatsu, T. et al. (1998) "IN VIVO ELECTROPORATION: A POWERFUL AND CONVENIENT MEANS OF NONVIRAL GENE TRANSFER TO TISSUES OF LIVING ANIMALS," Int. J. Mol. Med. 1:55-62; Garrison J. (1998) "IONTOPHORESIS: AN ALTERNATIVE DRUG-DELIVERY SYSTEM," Med. Device Technol. 9:32-36; Banga A. K. et al. (1998) "ASSESSING THE POTENTIAL OF SKIN ELECTROPORATION FOR THE DELIVERY OF PROTEIN- AND GENE-BASED DRUGS," Trends Biotechnol. 16:408-412; Banga A. K. et al. (1999) "IONTOPHORESIS AND ELECTROPORATION: COMPARISONS AND CONTRASTS," Int. J. Pharm. 179:1-19; Neumann E. et al. (1999) "FUNDAMENTALS OF ELECTROPORATIVE DELIVERY OF DRUGS AND GENES," Bioelectrochem. Bioenerg. 48:3-16; and Heiser, W. C. (2000) "OPTIMIZING ELECTROPORATION CONDITIONS FOR THE TRANSFORMATION OF MAMMALIAN CELLS," Methods Mol. Biol. 130:117-134.

The nature of the electric field generated in accordance with such methods is determined by the nature of the tissue, the size of the selected tissue and its location. The use of insufficient or excessive field strength is to be avoided. As used herein, a field strength is excessive if it results in the lysing of cells. A field strength is insufficient if it results in a reduction of efficacy of 90% relative to the maximum efficacy obtainable. The electrodes may be mounted and manipulated in many ways known in the art. The waveform of the electrical signal provided by the pulse generator can be an exponentially decaying pulse, a square pulse, a unipolar oscillating pulse train or a bipolar oscillating pulse train. The waveform, electric field strength and pulse duration are dependent upon the type of cells and the DNA that are to enter the cells via electrical-mediated delivery and thus are determined by those skilled in the art in consideration of these criteria. Any number of known devices may be used for delivering polynucleotides and generating the desired electric field. Examples of suitable devices include, but are not limited to, a single needle probe, a bipolar probe and a combination needle and plate probe. Alternatively, methods such as continuous-flow electroporation may be employed (See, U.S. Pat. Nos. 6,485,961; 6,090,617; 6,074,605; 5,720,921; 5,612,207; and 5,098,843).

The compositions of the present invention can be lyophilized to produce pharmaceutical compositions in a dried form for ease in transportation and storage. The pharmaceutical compositions of the present invention may be stored in a sealed vial, ampule or the like. In the case where the pharmaceutical composition is in a dried form, the composition is dissolved or suspended (e.g., in sterilized distilled water) before administration. An inert carrier such as saline or phosphate buffered saline or any such carrier in which the pharmaceutical compositions has suitable solubility, may be used.

Further, the pharmaceutical compositions may be prepared in the form of a mixed composition that contains one or more additional constituents so long as such additional constituents do not interfere with the effectiveness of the p21 inhibitor and the side effects and adverse reactions are not increased additively or synergistically. The pharmaceutical compositions of the present invention can be associated with chemical moieties which may improve the composition's solubility, absorption, biological half life, etc. The moieties may alternatively decrease the toxicity of the pharmaceutical compositions, eliminate or attenuate any undesirable side effect of the pharmaceutical compositions, etc. Moieties capable of mediating such effects are disclosed in Remington's Pharmaceutical Sciences (1980). Procedures for coupling such moieties to a molecule are well known in the art.

Determining an effective amount of a composition depends upon a number of factors including, for example, the chemical structure and biological activity of the substance, the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

In one embodiment, the pharmaceutical compositions of the present invention are administered free from association with liposomal formulations, charged lipids, or transfection-facilitating viral particles. In another embodiment, the compositions of the present invention are administered free from association with any delivery vehicle now known in the art that can facilitate entry into cells.

As used herein, "ex vivo" cells are cells into which the pharmaceutical compositions are introduced, for example, by transfection, lipofection, electroporation, bombardment, or microinjection. The cells containing the pharmaceutical compositions are then administered in vivo into mammalian tissue (see, for example, see Belldegrun, A., et al. (1993) "HUMAN RENAL CARCINOMA LINE TRANSFECTED WITH INTERLEUKIN-2 AND/ OR INTERFERON ALPHA GENE(S): IMPLICATIONS FOR LIVE CANCER VACCINES," J. Natl. Cancer Inst. 85: 207-216; Ferrantini, M. et al. (1993) "ALPHA 1-INTERFERON GENE TRANSFER INTO METASTATIC FRIEND LEUKEMIA CELLS ABROGATED TUMORIGENICITY IN IMMUNO-COMPETENT MICE: ANTITUMOR THERAPY BY MEANS OF INTER-FERON—PRODUCING CELLS," Cancer Research 53:1107-1112; Ferrantini, M. et al. (1994) "IFN-ALPHA 1 GENE EXPRESSION INTO A METASTATIC MURINE ADENOCARCINOMA (TS/A) RESULTS IN $CD8^+$ T CELL-MEDIATED TUMOR REJECTION AND DEVELOPMENT OF ANTITUMOR IMMUNITY. COMPARATIVE STUDIES WITH IFN-GAMMA-PRODUCING TS/A CELLS," J. Immunology 153:460-44615; Kaido, T. et al. (1995) "IFN-ALPHA 1 GENE TRANSFECTION COM-PLETELY ABOLISHES THE TUMORIGENICITY OF MURINE B 16 MELA-NOMA CELLS IN ALLOGENEIC DBA/2 MICE AND DECREASES THEIR TUMORIGENICITY IN SYNGENEIC C57BL/6 MICE," Int. J. Cancer 60: 221-229; Ogura, H. et al. (1990) "IMPLANTATION OF GENETI-CALLY MANIPULATED FIBROBLASTS INTO MICE AS ANTITUMOR ALPHA-INTERFERON THERAPY," Cancer Research 50:5102-5106; Sant-odonato, L. et al. (1996) "CURE OF MICE WITH ESTABLISHED METASTATIC FRIEND LEUKEMIA CELL TUMORS BY A COMBINED THERAPY WITH TUMOR CELLS EXPRESSING BOTH INTERFERON-ALPHA 1 AND HERPES SIMPLEX THYMIDINE KINASE FOLLOWED BY GANCI-CLOVIR," Human Gene Therapy 7:1-10; Santodonato, L., et al. (1997) "LOCAL AND SYSTEMIC ANTITUMOR RESPONSE AFTER COM-BINED THERAPY OF MOUSE METASTATIC TUMORS WITH TUMOR CELLS EXPRESSING IFN-ALPHA AND HSVTK: PERSPECTIVES FOR THE GENERATION OF CANCER VACCINES," Gene Therapy 4:1246-1255; and Zhang, J. F. et al. (1996) "GENE THERAPY WITH AN ADENO-ASSOCIATED VIRUS CARRYING AN INTERFERON GENE RESULTS IN TUMOR GROWTH SUPPRESSION AND REGRESSION," Cancer Gene Therapy 3:31-38.

In the "local delivery" embodiment of the present invention, a pharmaceutical composition is administered in vivo, such that the p21 inhibitor is incorporated into the local cells at the site of administration. The pharmaceutical compositions can be administered either within ex vivo cells or free of ex vivo cells or ex vivo cellular material. Preferably, the polynucleotide construct is administered free of ex vivo cells or ex vivo cellular material.

The pharmaceutical compositions can be solubilized in a buffer prior to administration. Suitable buffers include, for example, phosphate buffered saline (PBS), normal saline, Tris buffer, and sodium phosphate vehicle (100-150 mM preferred). Insoluble polynucleotides can be solubilized in a weak acid or base, and then diluted to the desired volume with a neutral buffer such as PBS. The pH of the buffer is suitably adjusted, and moreover, a pharmaceutically acceptable additive can be used in the buffer to provide an appropriate osmolarity within the lipid vesicle. Preferred salt solutions and auxiliary agents are disclosed herein.

A systemic delivery embodiment is particularly preferred for treating non-localized disease conditions. A local delivery embodiment can be particularly useful for treating disease conditions that might be responsive to high local concentration. When advantageous, systemic and local delivery can be combined. U.S. Pat. Nos. 5,589,466, 5,693,622, 5,580,859, 5,703,055, and PCT publication WO94/29469 provide methods for delivering compositions comprising naked DNA, or DNA cationic lipid complexes to mammals.

Compositions used in the present invention can be formulated according to known methods. Suitable preparation methods are described, for example, in Remington's Pharmaceutical Sciences, $16^{th}$ Edition, A. Osol, ed., Mack Publishing Co., Easton, Pa. (1980), and Remington's Pharmaceutical Sciences, $19^{th}$ Edition, A. R. Gennaro, ed., Mack Publishing Co., Easton, Pa. (1995), both of which are incorporated herein by reference in their entireties. Although the composition is preferably administered as an aqueous solution, it can be formulated as an emulsion, gel, solution, suspension, lyophilized form, or any other form known in the art. According to the present invention, if the composition is formulated other than as an aqueous solution, it will require resuspension in an aqueous solution prior to administration. In addition, the composition may contain pharmaceutically acceptable additives including, for example, diluents, binders, stabilizers, and preservatives.

The present invention also provides kits for use in treating HIV infection comprising an administration means and a container means containing a pharmaceutical composition of the present invention. Preferably, the container in which the composition is packaged prior to use will comprise a hermetically sealed container enclosing an amount of the lyophilized formulation or a solution containing the formulation suitable for a pharmaceutically effective dose thereof, or multiples of an effective dose. The composition is packaged in a sterile container, and the hermetically sealed container is designed to preserve sterility of the pharmaceutical formulation until use. Optionally, the container can be associated with administration means and/or instruction for use.

Having now generally described the invention, the same will be more readily understood through reference to the following examples, which are provided by way of illustration, and are not intended to be limiting of the present invention, unless specified.

Example 1

Materials and Methods for the Analysis of Temporal Events Associated with the Initial Virus-Macrophage Encounter A. Purification of Human Monocytes by Counterflow Centrifugal Elutriation Human peripheral blood cells are obtained by leukapheresis from normal volunteers in the Department of Transfusion Medicine at the National Institutes of Health (Bethesda, Md.) and diluted in endotoxin-free PBS without $Ca^{2+}$ and $Mg^{2+}$ (BioWhittaker, Walkersville, Md.) for density sedimentation. The monocytes in the mononuclear cell layer are purified by counterflow centrifugal elutriation within 4 hr after leukapheresis (Wahl, S. M. et al. (1984) "ISOLATION OF HUMAN MONONUCLEAR CELL SUBSETS BY COUNTERFLOW CENTRIFUGAL ELU- TRIATION (CCE). II. FUNCTIONAL PROPERTIES OF B-LYMPHOCYTE-, T-LYMPHOCYTE-, AND MONOCYTE-ENRICHED FRACTIONS. Cell Immunol 85:384-395).

B. HIV-1 Infection of Human Monocyte-Derived Macrophages

Monocytes are plated in 6 well plates (Corning Costar Corporation, Cambridge, Mass.), at $6 \times 10^6$ cells/well or in Lab-Tek chamber slides (Naperville, Ill.) at $1.5 \times 10^6$/chamber in Dulbecco's modified Eagle's medium (DMEM) with 2 mM L-glutamine and 10 μg/ml gentamicin (BioWhittaker) or in other suitable vessels. After adherence (4-6 hr at 37° C. and 5% $CO_2$), 10% human AB-serum (Sigma, St. Louis, Mo.) is added to the culture medium. Cells are cultured 5-10 days to allow differentiation into macrophages before being infected with HIV-$1_{BaL}$ $TCID_{50}$=1000-5000 (Advanced Biotechnologies Inc., Columbia, Md.) or other M tropic (R5) virus for 90 minutes at 37° C. The levels of endotoxin are below the limit of detection in virus preparations. Unbound virus is removed by washing the cells with media and refeeding with complete DMEM containing 10% human serum. Control populations of adherent macrophages are mock-infected and cultured in parallel. Every 3 to 4 days, half the medium is removed for virus assay and replaced with fresh complete medium for two weeks. Supernatant p24 antigen is assayed using the p24 core profile enzyme-linked immunosorbent assay (ELISA) kit (Perkin-Elmer Life Sciences, Wilmington, Del.). As described below, in certain experiments, macrophages are pre-treated with 2-cyano-3,12-dioxooleana-1,9-dien-28-oic acid (CDDO) or a CDDO analog (di-CDDO) for 45 minutes prior to exposure to HIV-1. Additionally, macrophages are treated with p21 anti-sense phosphorothioate oligonucleotides:

```
SEQ ID NO. 7:   5'-TGTCAGGCTGGTCTGCCTCC-3' (oligo 1),
and

SEQ ID NO. 9:   5'-ACATCACCAGGATTGGACAT-3' (oligo 2)
``` or negative control oligonucleotide:

```
SEQ ID NO. 14:  5'-TGGATCCGACATGTCAGA-3' (oligo 3)
```

(sequence obtained from Dr. Argyrios N. Theofilopoulos, The Scripps Research Institute, La Jolla, Calif.) after HIV-1 infection and at the time of refeeding the cultures and tested for viral replication at day 12. SEQ ID NOS. 7 and 9 are derived from the murine p21 antisense sequence, yet are effective in inhibiting human p21 expression and the replication and transmission of HIV.

C. Northern Blot Analysis and RNase Protection Assay (RPA)

Total cellular RNA is extracted from adherent control or infected monocytes with the RNeasy minikit (Qiagen, Valencia, Calif.) and analyzed by northern blot (Wahl, S. M. et al. (1998) "MYCOBACTERIUM AVIUM COMPLEX AUGMENTS MACROPHAGE HIV-1 PRODUCTION AND INCREASES CCR5 EXPRESSION. Proc Natl Acad Sci USA 95:12574-12579) using an HIV-full length probe (NIH AIDS Research and Reference Reagent Program) and GAPDH (glyceraldehyde-3-phosphate dehydrogenase) (Gibco BRL, Gaithersburg, Md.). For the RPA 3 μg of RNA is evaluated using the hStress tRiboquant Multi-Probe RPA system (BD Pharmingen, San Diego, Calif.) and densities are normalized to the GAPDH gene using ImageQuant (Molecular Dynamics, Sunnyvale, Calif.)

D. cDNA Expression Array

The Altlas human cDNA Expression Array 1.2 I (Clontech, Palo Alto, Calif.) (catalog #7850-1) is performed using 5 μg of DNase digested total RNA as described by Greenwell-Wild, T. et al. (2002) "MYCOBACTERIUM AVIUM INFECTION AND MODULATION OF HUMAN MACROPHAGE GENE EXPRESSION." J Immunol 169:6286-6297. Gene expression in infected cells is compared with the corresponding control population from the same donor expressed as a ratio (fold change) after normalization to housekeeping genes. A total of seven different donors are analyzed.

E. Transmission Electron Microscopy (TEM)

Gluteraldehyde-fixed uninfected and infected cells are postfixed in $OsO_4$, dehydrated through graded ethanol and propylene oxide, embedded in Spurr's epoxy, and thick- and thin-sectioned. Thin sections are placed on copper grids, stained with uranyl acetate and lead citrate, and viewed in a Zeiss EM10 microscope (LEO Electron Microscope; Oberkochen, Germany).

F. Immunofluorescence Microscopy

Uninfected and HIV-1 infected macrophages that have been cultured for twelve days are washed twice with PBS, fixed with 2% paraformaldehyde in PBS, washed and incubated in 100 mM glycine in PBS for 20 min, followed by 0.5% Triton-X-100 for 10 min and rinsed with PBS. Cells are then labeled with rabbit anti-p21 antibody at 5 μg/ml (Santa Cruz Biotechnology, Santa Cruz, Calif.) in PBS containing 5% donkey serum (Jackson ImmunoResearch Laboratories, Inc., West Grove, Pa.) for 1 hr, washed extensively, then incubated with Texas-Red conjugated secondary antibody at 3 μg/ml at room temperature (Molecular Probes, Eugene, Oreg.). Non-specific background is determined using an irrelevant rabbit isotype control antibody and secondary antibody alone at the same concentrations above. Images are captured using a Leica TCS-4D confocal microscope system with a Kr—Ar laser on a DMR upright microscope using a 40×, 1.0 numerical aperture objective. Fluorescence intensity analysis is performed using confocal microscopy and Metamorph analysis (Universal Imaging, Downington, Pa.).

G. Immunoprecipitation and Western Blot Analysis

Whole cell lysates are generated using a lysis buffer that consisted of 1% Nonidet P-40, 150 mM NaCl, 20 mM Tris-HCl (pH, 7.5), 10 mM NaF, 10 mM NaPPi, 2.5 nM EDTA, 1 mM $Na_3VO_4$, 0.2 mM 3, 4 dichloroisocoumarin, 1 mM phenylmethylsulfonyl fluoride, 100 ug/ml chymostatin and 1× complete protease inhibitor (Boehringer Mannheim, Indianapolis, Ind.). CDKN1A is immunoprecipitated from cell lysates using an anti-CDKN1A antibody conjugated to agarose (Santa Cruz Biotechnology) and incubated with constant rotation at 4° C. for 2 hours. Immunoprecipitates are electrophoresed onto Tricine gels (Invitrogen, Carlsbad, Calif.), transferred to nitrocellulose membrane and immunoblotted with anti-CDKN1A (BD Pharmingen). Immunoblots are developed using enhanced chemiluminescence and the Super-Signal substrate according to manufacturer's instructions (Pierce Chemical Co, Rockford, Ill.).

Example 2

Figure 1B:
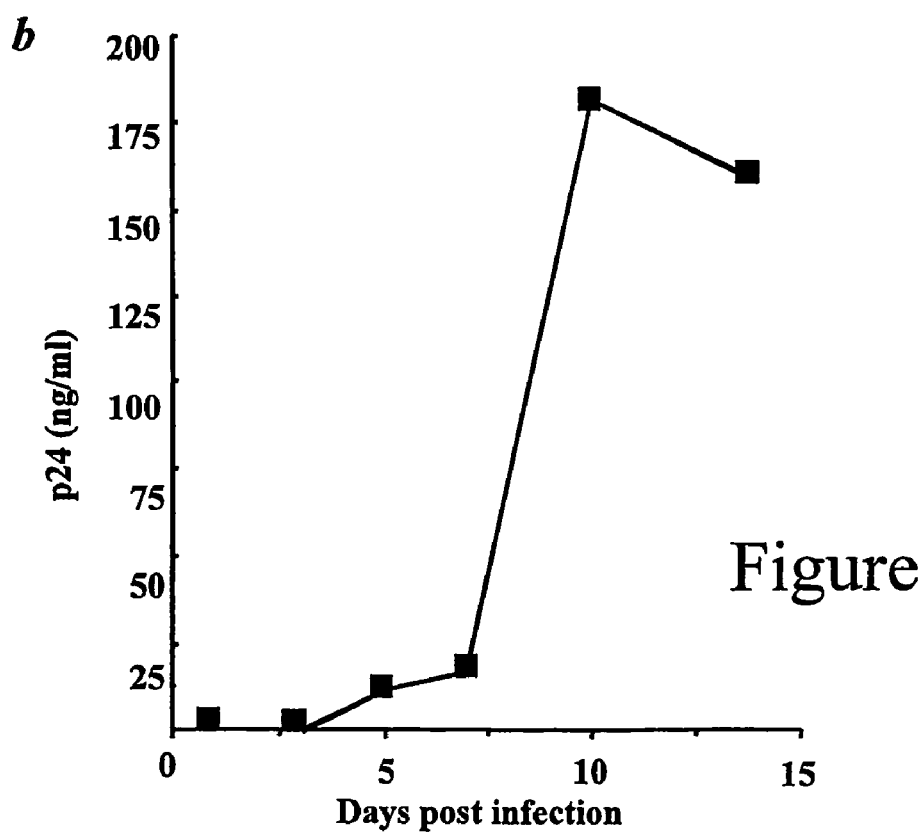
Figure 1C:
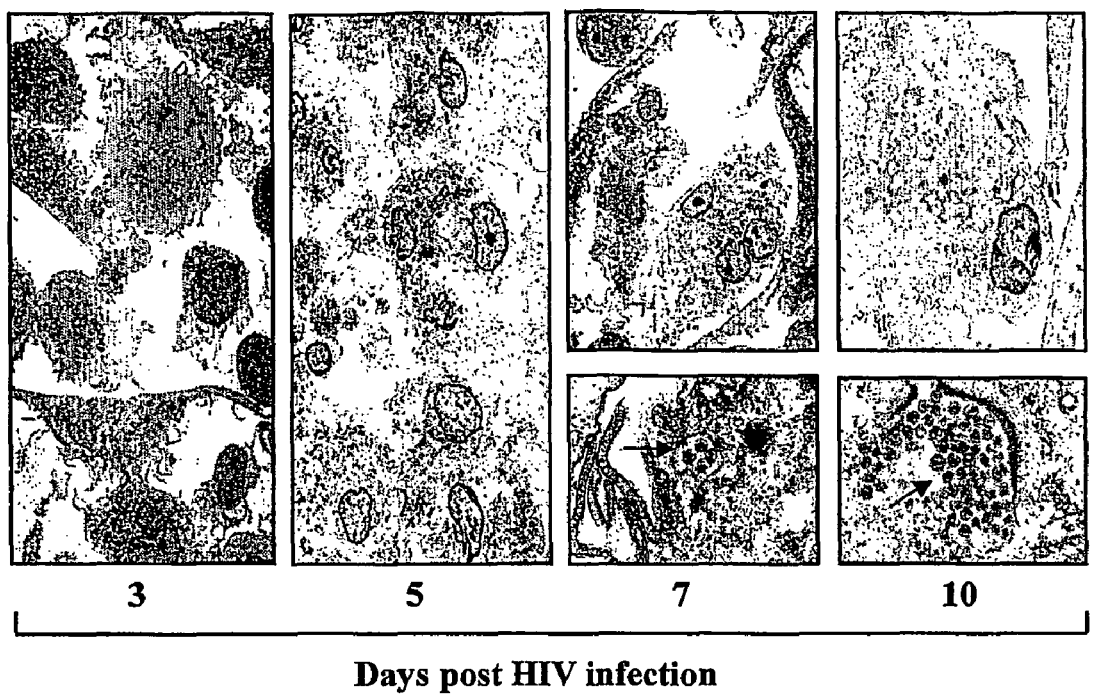
Figure 1D:
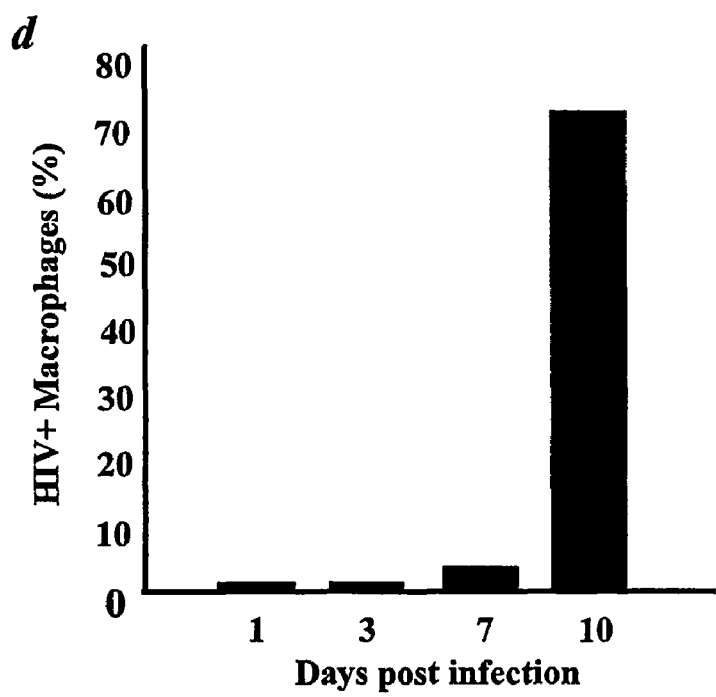
Figure 2A:
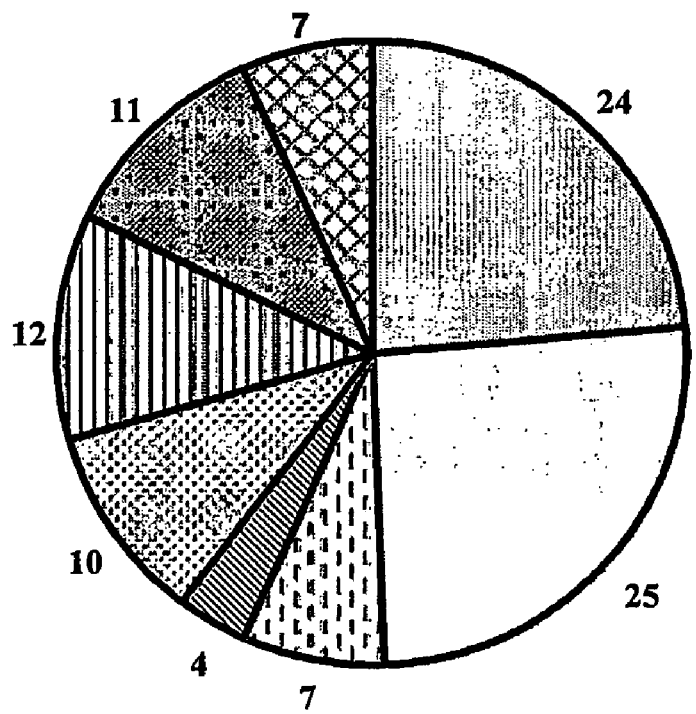
FIGS. 2A-2E illustrate HIV-induced alterations in macrophage transcriptome.
Figure 2B:
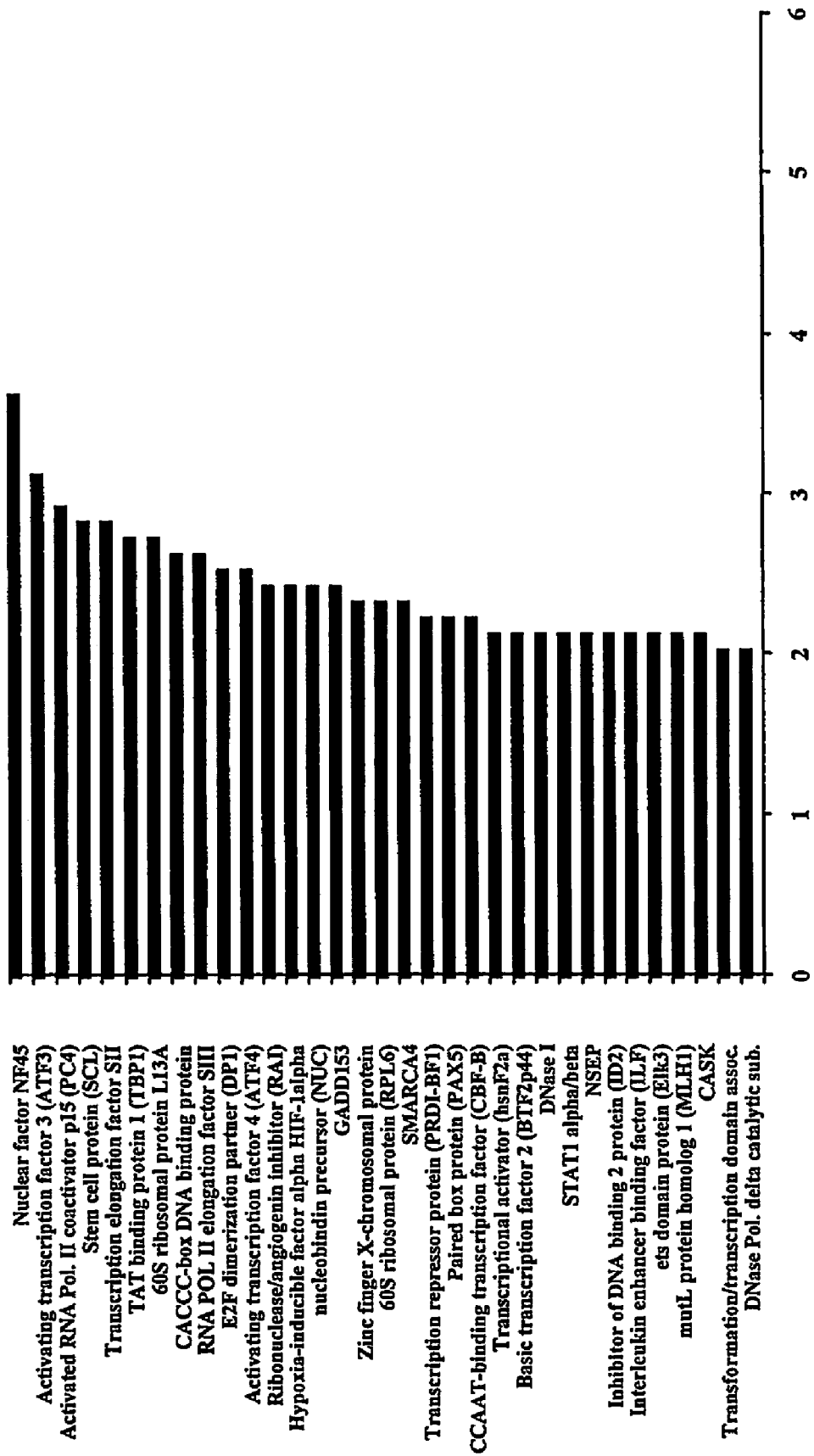
Figure 2C:
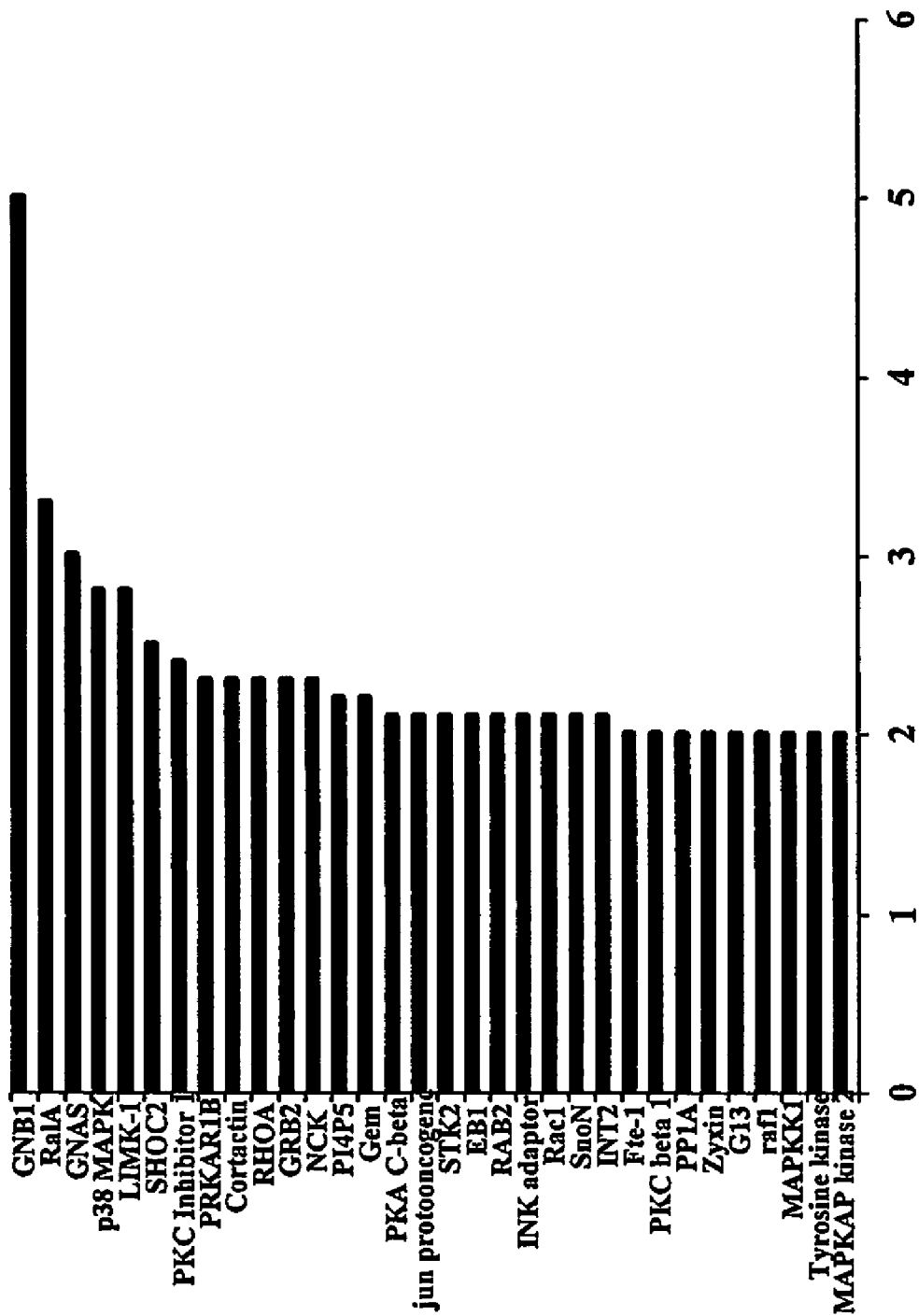
Figure 2D:
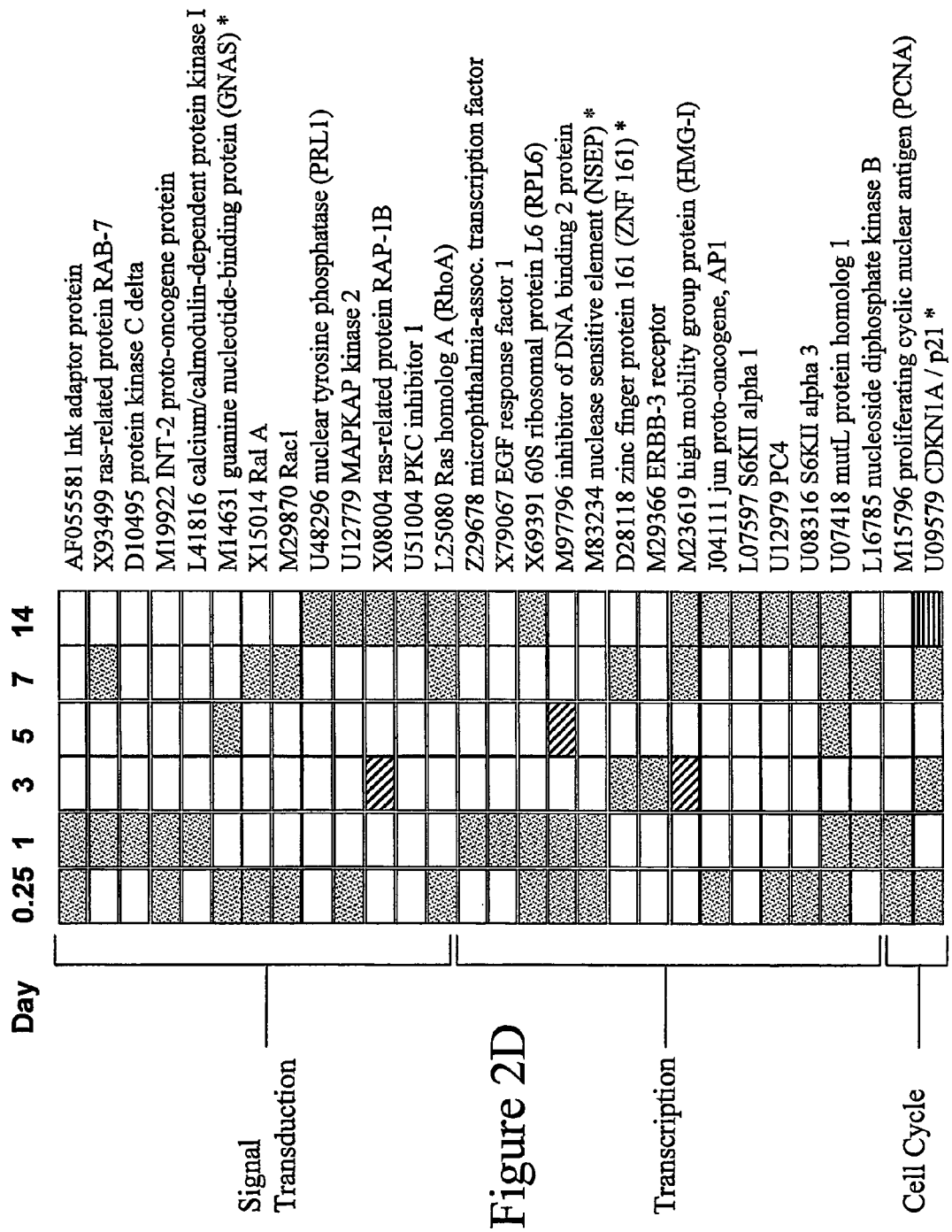
Figure 2E:
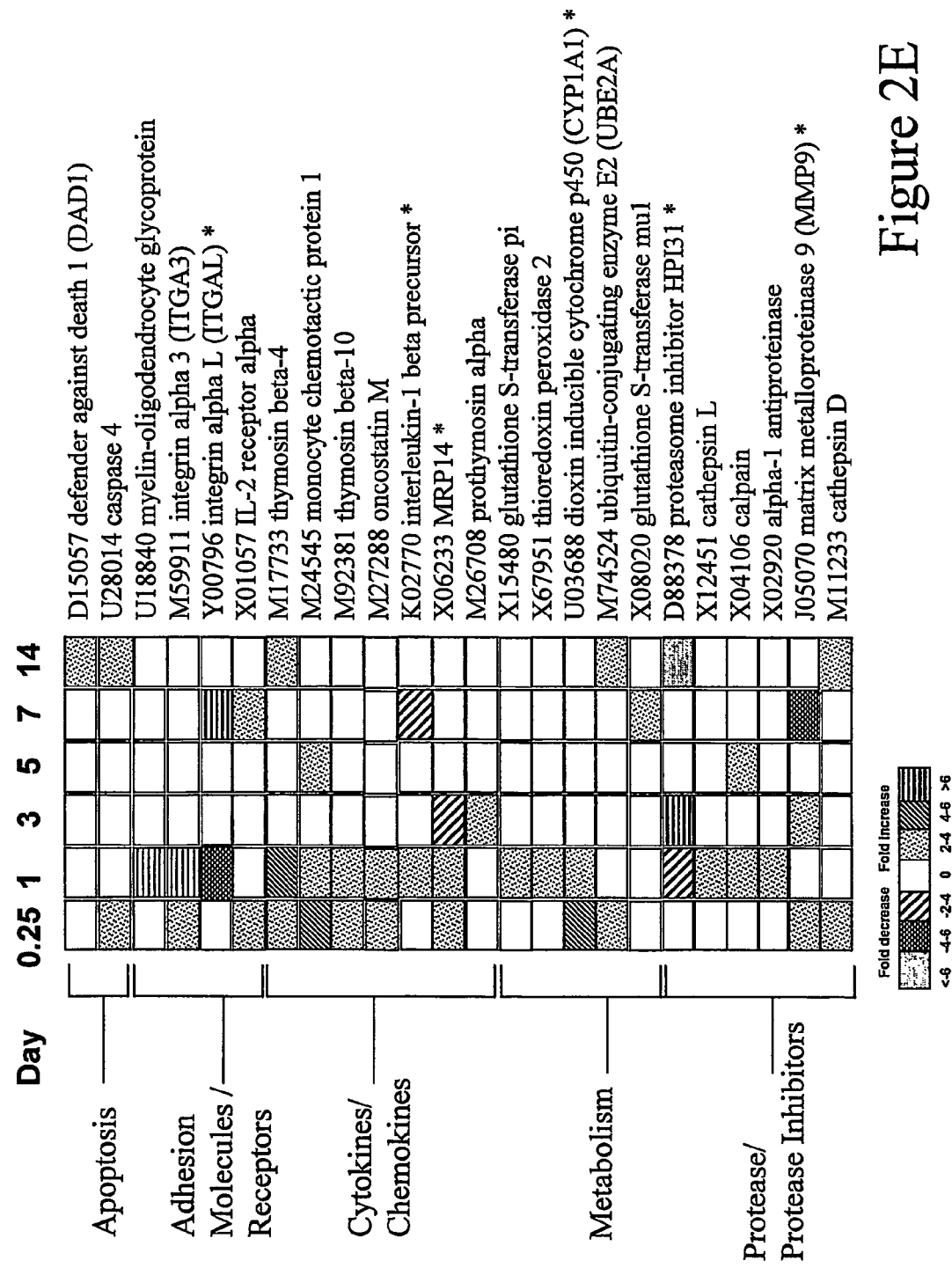

Results of the Analysis of Temporal Events Associated with the Initial Virus-Macrophage Encounter A. Kinetics of HIV-1 Replication in Adherent Macrophages Elutriated monocytes are adhered for 7 days, exposed to an R5HIV$_{BaL}$ for 90 minutes, washed and the kinetics of cellular and viral changes are monitored. HIV-1 RNA is typically detected on day 5, becoming increasingly apparent by 10-16 days after initial exposure to the virus (FIG. 1A). In parallel, detectable p24 antigen becomes evident within 5 days, then increases dramatically (FIG. 1B). Ultrastructurally, viral particles are not be seen in the adherent macrophages at day 1-5, although an increase in binucleated cells and then an increasing frequency of multinucleated cells can be observed (FIG. 1C). Consistent with viral RNA and p24 antigen, virus is visibly detected by electron microscopy around day 7 (FIG. 1C; FIG. 1D) with ≧70% of the cells typically harboring large numbers of virions by day 10 (FIG. 1C; FIG. 1D). HIV-1 is being produced on the complex surfaces between cells, on the free surfaces and in cytoplasmic vacuoles of the Golgi apparatus. Nonetheless, once the majority of cells are infected and large numbers of virions are present within and on the surface of the macrophages, p24 levels plateau, likely dependent on host factors.

B. Initial Gene Expression In HIV-1-Infected Macrophage Populations

To examine the host factors underlying viral propagation, transcriptional pathways that are activated downstream of the CD4-HIV-1 co-receptor binding/signaling event are examined by cDNA expression arrays. Compared with the control mock-infected macrophage population, an early and transient gene expression profile occurs, followed by a delayed pattern that emerges in association with viral replication. Within 3-6 hours upregulated genes defined as exhibiting a ≧2 fold increase above baseline in ≧4 donors (134 of 1200 interrogated) are associated predominantly with signal transduction pathways (24%) and transcription (25%) (FIGS. 2A-2E), many consistent with downstream effects of engaging the G protein signaling pathway. Genes corresponding to the mitogen activated protein kinase (MAPK) family are increased, including p38 MAPK and MAPKA-K2.

In addition to genes involved in transcription and signal transduction, multiple genes associated with cell cycle, apoptosis, and cellular recruitment (Table 1), including chemokines (IL-8, MCP-1, and MRP14) involve viral replication (Lane, B. R. et al. (2001) "INTERLEUKIN-8 STIMULATES HUMAN IMMUNODEFICIENCY VIRUS TYPE 1 REPLICATION AND IS A POTENTIAL NEW TARGET FOR ANTIRETROVIRAL THERAPY," J Virol 75:8195-8202; Cinque, P. et al. (1998) "ELEVATED CEREBROSPINAL FLUID LEVELS OF MONOCYTE CHEMOTACTIC PROTEIN-1 CORRELATE WITH HIV-1 ENCEPHALITIS AND LOCAL VIRAL REPLICATION," Aids 12:1327-1332; Strasser, F. et al. (1997) "ELEVATED SERUM MACROPHAGE INHIBITORY FACTOR-RELATED PROTEIN (MRP) 8/14 LEVELS IN ADVANCED HIV INFECTION AND DURING DISEASE EXACERBATION," J Acquir Immune Defic Syndr Hum Retrovirol 16:230-238) are upregulated. Enhanced surface adhesion molecules VNRA, CD11c, ICAM1, FNRA, CD44, ITGAE can influence HIV infection, virion interaction with the target cell and syncytium formation (Shattock, R. J. et al. (1996) "ENHANCED HIV REPLICATION IN MONOCYTIC CELLS FOLLOWING ENGAGEMENT OF ADHESION MOLECULES AND CONTACT WITH STIMULATED T CELLS," Res Virol 147:171-179) and also an incorporation into HIV virions (Guo, M. M. et al. (1995) "HIV ACQUIRES FUNCTIONAL ADHESION RECEPTORS FROM HOST CELLS," AIDS Res Hum Retroviruses 11: 1007-1013).

TABLE 1

Early HIV-1 Upregulated Macrophage Gene Expression

| GenBank Accession Number | Gene Description | Average Fold Increase |
|---|---|---|
| Signal Transduction | | |
| M36430 | GNBI | 5.0 |
| X15014 | Ral A | 3.3 |
| D26309 | LIMK -1 | 3.1 |

TABLE 1-continued

Early HIV-1 Upregulated Macrophage Gene Expression

| GenBank Accession Number | Gene Description | Average Fold Increase |
|---|---|---|
| M14631 | GNAS | 3.0 |
| L35253 | MAP kinase p38 | 3.0 |
| L29511 | GRB2 | 2.7 |
| AF068920 | SHOC 2 | 2.5 |
| L25080 | Ras homolog A (RhoA) | 2.5 |
| AF055581 | LNK adaptor | 2.4 |
| X17576 | NCK melanoma cytoplasmic src/homolog | 2.3 |
| M98343 | Cortactin (ems-I) | 2.3 |
| M65066 | PRKAR1B | 2.3 |
| U10550 | Gem (ras family) | 2.2 |
| U78576 | PI4P5 kinase alpha | 2.2 |
| U12779 | MAPKAP kinase 2 | 2.2 |
| M19922 | INT2 | 2.1 |
| X15219 | SnoN | 2.1 |
| M29870 | Rac1 | 2.1 |
| M28213 | Rab2 | 2.1 |
| U24166 | EB1 | 2.1 |
| L20321 | Serine/threonine kinase NRK2 | 2.1 |
| M34181 | PKC beta | 2.1 |
| X60957 | Tyrosine kinase receptor Tie-l | 2.0 |
| L05624 | MAPKK1 | 2.0 |
| X03484 | Raf1 protooncogene | 2.0 |
| L22075 | G13 | 2.0 |
| X94991 | Zyxin 2 | 2.0 |
| M63960 | PPIalpha | 2.0 |
| X06318 | PKC beta 1 | 2.0 |
| M77234 | Fte-1 | 2.0 |
| X08004 | Rap1b | 2.0 |
| Transcription | | |
| U10323 | NF45 | 3.6 |
| L19871 | Activating factor 3 (ATF3) | 3.1 |
| U12979 | Activated RNA polymerase n transcriptional coactivator p15 (PC4) | 2.9 |
| M81601 | Transcription elongation factor SII | 2.8 |
| M29038 | Stem cell protein | 2.8 |
| D90209 | Activating factor 4 (ATF4) | 2.8 |
| M34079 | TAT binding protein (TBP-1) | 2.7 |
| L34587 | RNA polymerase II Elongation factor SIII p15 subunit | 2.6 |
| L04282 | CACCC-box DNA binding protein | 2.6 |
| U22431 | Hypoxia-inducible factor 1 alpha | 2.5 |
| L23959 | E2F dimerization partner 1 (DP1) | 2.5 |
| M83234 | NSEP | 2.5 |
| S40706 | GADD153 | 2.4 |
| M96824 | nucleobindin precursor (NUC) | 2.4 |
| M36717 | Ribonuclease/angiogenin inhibitor (RAI) | 2.4 |
| D26156 | SW1/SNF-related actin-dependent regulator of chromatin | 2.3 |
| X69391 | 60s ribosomal protein (RPL6) | 2.3 |
| X59738 | Zinc finger x-chromosomal protein | 2.3 |
| M59079 | CBF-B | 2.2 |
| M96944 | PAX5 | 2.2 |
| AF084199 | PRDI-BFl (transcription repressor protein) | 2.2 |
| M97796 | Inhibitor of DNA binding 2 (ID2) | 2.2 |
| U07418 | MutL protein homolog 1 (MLH1) | 2.2 |
| AF060222 | DNase II | 2.2 |
| U58198 | Interleukin enhancer binding factor (ILF) | 2.1 |
| Z36715 | Elk-3 | 2.1 |
| AF032119 | CASK | 2.1 |
| M97935 | STAT1 alpha/beta | 2.1 |
| Z30094 | Basic transcription factor 2 (BTF2p44) | 2.1 |
| J04111 | jun protooncogene, AP-1 | 2.1 |
| D26155 | Transcriptional activator (hsnF2a) | 2.0 |
| M80397 | DNA polymerase delta catalytic subunit | 2.0 |
| AF076974 | Transformation/transcription domain associated protein | 2.0 |

TABLE 1-continued

Early HIV-1 Upregulated Macrophage Gene Expression

| GenBank Accession Number | Gene Description | Average Fold Increase |
|---|---|---|
| Cell Cycle/Apoptosis | | |
| U13737 | Caspase 3 | 2.2 |
| L29222 | CDC-like kinase (CLK1) | 2.1 |
| AF071596 | IEX-IL anti-death protein | 2.1 |
| M15796 | Proliferating cyclic nuclear antigen (PCNA) | 2.1 |
| X96586 | FAN protein | 2.1 |
| U28014 | Caspase-4 | 2.1 |
| Z23115 | bcl-x | 2.0 |
| U09579 | cyclin-dependent kinase inhibitor IA (CDKNIA) | 2.0 |
| Adhesion Molecules/Receptors | | |
| M14648 | Vitronectin receptor alpha (VNRA) | 3.3 |
| J03132 | Intercellular adhesion molecule 1 (ICAM1) | 3.1 |
| M81695 | CDI1c antigen | 2.5 |
| X06256 | Fibronectin receptor alpha (FNRA) | 2.5 |
| D84657 | Photolyase/blue-light receptor homolog | 2.4 |
| X07979 | Fibronectin receptor beta (FNRB) | 2.7 |
| D13866 | Alpha 1 catenin | 2.4 |
| X72304 | Corticotropin releasing factor receptor 1 | 2.4 |
| M59911 | Integrin alpha 3 (ITGA3) | 2.3 |
| M37722 | Fibroblast growth factor receptor 1 | 2.2 |
| L25851 | Integrin alpha E (ITGAE) | 2.1 |
| M27492 | IL-1 receptor type I | 2.0 |
| J04536 | Leukosialin | 2.0 |
| X01057 | IL2R alpha | 2.0 |
| M59040 | CD44 antigen | 2.0 |
| Chemokines/Cytokines | | |
| Y00787 | Interleukin-8 | 9.7 |
| M65291 | Interleukin-12 alpha | 5.0 |
| M24545 | Monocyte chemotactic protein 1 (MCP-1) | 4.5 |
| X06233 | Migration inhibitory factor-related protein 14 (MRP14) | 3.8 |
| M92381 | Thymosin beta 10 | 3.7 |
| MI7733 | Thymosin beta 4 | 3.6 |
| X01394 | Tumor necrosis factor alpha (TNF alpha) | 3.4 |
| X53655 | Neurotrophin-3 precursor | 2.6 |
| M21121 | Small inducible protein A5 (SCYA5) | 2.5 |
| M86492 | Glia maturation factor beta | 2.2 |
| M31145 | Insulin-like growth factor binding protein 1 | 2.2 |
| M27288 | Oncostatin M (OSM) | 2.1 |
| U13699 | IL-1 beta converting enzyme (ICE) | 2.1 |
| U16296 | T-lymphoma-invasion & metastasis inducing (TIAM1) | 2.0 |
| M25667 | Neuromodulin | 2.0 |
| X02530 | Interferon gamma-induced protein (IP-IO) | 2.0 |
| Proteases/Protease Inhibitors | | |
| M11233 | Cathepsin D | 3.2 |
| J05070 | Matrix metalloproteinase 9 (MMP9) | 3.1 |
| X56692 | C reactive protein | 2.9 |
| AF059244 | Cystatin related protein | 2.8 |
| X05562 | Procollagen alpha 2 | 2.5 |
| L23808 | Matrix metalloproteinase 12 | 2.2 |
| D00762 | Proteasome C8 | 2.1 |
| Z81326 | Protease inhibitor 12 | 2.0 |
| L40377 | Cytoplasmic antiprotease 2 (CAP2) | 2.0 |
| M23254 | Calpain 2 | 2.0 |
| X04106 | Calpain | 2.0 |
| Metabolism | | |
| U03688 | dioxin inducible cytochrome p450 (CYP1A1) | 4.5 |
| X06985 | Heme oxygenase 1 (HO-1) | 4.2 |
| U34683 | Glutathione synthetase | 3.0 |
| X07270 | 90-kDa heat-shock protein A | 2.7 |
| U29091 | Selenium binding protein | 2.7 |
| L14595 | Neural amino acid transporter A (SATT) | 2.6 |
| DO0099 | Na+/K+ transporting ATPase alpha 1 | 2.4 |
| M74524 | Ubiquitin conjugating enzyme (UBE2A) | 2.3 |
| X91247 | Thioredoxin reductase | 2.3 |
| X54079 | 27-kDa heat-shock protein | 2.2 |
| Ml1717 | 70-kDa heat shock protein 1 | 2.1 |
| L20046 | Xeroderma pigmentosum group G complementing protein | 2.0 |
| Y00264 | Alzheimer's disease amyloid A4 protein | 2.0 |

Although gene expression for caspases 3, 4 and 8 is increased, genes encoding factors that contribute to cellular resistance to apoptosis including IEX-1L and bcl-x (Wu, M. X. et al. (1998) "IEX-1L, AN APOPTOSIS INHIBITOR INVOLVED IN NF-KAPPAB-MEDIATED CELL SURVIVAL, Science 281:998-1001; Antonsson, B. et al. (2000) "THE BCL-2 PROTEIN FAMILY," Exp Cell Res 256:50-57) are concurrently elevated (Table 1). As reported, IL-2 receptor mRNA is also enhanced in HIV-infected macrophages (Allen, J. B. et al. (1990) "EXPRESSION OF INTERLEUKIN 2 RECEPTORS BY MONOCYTES FROM PATIENTS WITH ACQUIRED IMMUNODEFICIENCY SYNDROME AND INDUCTION OF MONOCYTE INTERLEUKIN 2 RECEPTORS BY HUMAN IMMUNODEFICIENCY VIRUS IN VITRO," J Clin Invest 85:192-199). Another gene upregulated in infected cells within hours and at day 1 is CYP1A1, previously associated with enhanced HIV-1 gene expression in vitro and with acceleration in the progression of AIDS mediated by an oxidative stress pathway Yao, Y. et al. (1995) "DIOXIN ACTIVATES HIV-1 GENE EXPRESSION BY AN OXIDATIVE STRESS PATHWAY REQUIRING A FUNCTIONAL CYTOCHROME P450 CYP1A1 ENZYME," Environ Health Perspect 103:366-71). However, the augmented transcriptional activity for heme oxygenase-1 (HO-1), a multifunctional protein that plays a role in the regulation of cellular heme, could protect these viral host cells against oxidative stress and is increased in PBMC of AIDS patients (Levere, R. D. et al. (1993) "ELEVATED LEVELS OF HEME OXYGENASE-1 ACTIVITY AND mRNA IN PERIPHERAL BLOOD ADHERENT CELLS OF ACQUIRED IMMUNODEFICIENCY SYNDROME PATIENTS," Am J Hematol 43, 19-23).

HO-1, together with increased glutathione synthetase (Table 1) may help provide a balance and protect the macrophage from oxidative stress generated by the virus (Mialocq, P. et al. (2001) "OXIDATIVE METABOLISM OF HIV-INFECTED MACROPHAGES: THE ROLE OF GLUTATHIONE AND A PHARMACOLOGIC APPROACH," Pathol Biol (Paris) 49:567-571; Toborek, M. et al. (2003) "HIV-TAT PROTEIN INDUCES OXIDATIVE AND INFLAMMATORY PATHWAYS IN BRAIN ENDOTHELIUM," J Neurochem 84:169-179). Furthermore, transcription for the host cell Tat binding protein (TBP-1) that interacts with viral Tat is rapidly elevated in HIV infected macrophages) Nelbock, P. et al. (1990) "A CDNA FOR A PROTEIN THAT INTERACTS WITH THE HUMAN IMMUNODEFICIENCY VIRUS TAT TRANSACTIVATOR," Science 248:1650-1653 (1990). In the early virus-induced transcriptional events, HIV-1 clearly enhances more genes than it suppresses since only tripeptidyl peptidase I, a lysosomal serine protease with a minor endoprotease activity responsible for cleaving tripeptides from the N terminus of oligopeptides (Tomkinson, B. (1999) "TRIPEPTIDYL PEPTIDASES: ENZYMES THAT COUNT," Trends Biochem Sci 24:355-359) is reproducibly suppressed. Since this protein is involved in protein turnover, control of its expression in the host cell could benefit the virus to ensure that infection is established.

C. Kinetics of HIV-1 Induced Gene Expression

The initial pattern of expression observed following binding of HIV-1 to macrophages in 4-7 donors, consistent with receptor engagement, is transient and by 24 hr, a restricted number of genes remain or are newly elevated (Table 2).

TABLE 2

Genes Upregulated in Macrophages from Day 1-14 after HIV-1 Infection

| GenBank Accession Number | Gene Description | Fold Increase |
|---|---|---|
| Day 1 | | |
| M17733 | thymosin beta 4 | 4.6 |
| X15480 | glutathione S-transferase pi | 3.4 |
| X12451 | cathepsin L | 3.0 |
| M24545 | monocyte chemotactic protein 1 (MCP-1) | 2.7 |
| L16785 | nucleoside diphosphate kinase B | 2.7 |
| X93499 | ras-related protein RAB-7 | 2.5 |
| U07418 | mutL protein homolog1 (MLH1) | 2.4 |
| M15796 | proliferating cyclic nuclear antigen (PCNA) | 2.4 |
| M83234 | nuclease sensitive element (NSEP) | 2.3 |
| D10495 | protein kinase C delta | 2.3 |
| Z29678 | microphthalmia-assoc. transc. factor(MITF) | 2.3 |
| X04106 | Calpain | 2.3 |
| X02920 | alpha-1-antiproteinase | 2.2 |
| M19922 | INT-2 proto-oncogene protein | 2.2 |
| L41816 | calcium/calmodulin-dependent protein kinase I(camki) | 2.2 |
| X79067 | EGF response factor 1 | 2.1 |
| U18840 | myelin-oligodendrocyte glycoprotein | 2.1 |
| U03688 | CYP1B1 | 2.1 |
| X69391 | 60S ribosomal protein L6 (RPL6) | 2.1 |
| M92381 | thymosin beta-10 | 2.1 |
| K02770 | interleukin-1 beta | 2.1 |
| X06233 | calgranulin B | 2.0 |
| M97796 | inhibitor of DNA binding 2 protein | 2.0 |
| M59911 | integrin alpha 3 (ITGA3) | 2.0 |
| AF055581 | lnk adaptor protein | 2.0 |
| X67951 | thioredoxin peroxidase 2 (TDPX2) | 2.0 |
| Day 3 | | |
| D88378 | proteasome inhibitor HPI31 | 8.3 |
| D28118 | ZNF 161 | 2.6 |
| M26708 | prothymosin alpha | 2.1 |
| J05070 | matrix metalloproteinase 9 (MMP9) | 2.0 |
| M29366 | ERBB-3 receptor | 2.0 |
| U09579 | CDKN1A | 2.0 |
| Day 5 | | |
| M24545 | monocyte chemotactic protein 1 (MCP-1) | 2.3 |
| M14631 | guanine nucleotide-binding protein(GNAS) | 2.2 |
| X04106 | Calpain | 2.1 |
| U07418 | mutL protein homolog1 (MLH1) | 2.1 |
| Day 7 | | |
| Y00796 | integrin alpha L (ITGAL) | 8.7 |
| X15014 | Ral A; GTP-binding protein | 3.5 |
| U09579 | CDKN1A | 3.5 |
| L16785 | nucleoside diphosphate kinase B | 3.1 |
| X01057 | IL-2 receptor alpha | 2.9 |
| M29870 | Rac1 | 2.5 |
| M23619 | high mobility group protein (HMG-I) | 2.3 |
| X93499 | ras related protein RAB-7 | 2.3 |
| U07418 | mutL protein homolog1 (MLH1) | 2.2 |

TABLE 2-continued

Genes Upregulated in Macrophages from Day 1-14 after HIV-1 Infection

| GenBank Accession Number | Gene Description | Fold Increase |
|---|---|---|
| D28118 | zinc finger protein 161 (ZNF161) | 2.2 |
| L25080 | Ras homolog A (RhoA) | 2.1 |
| X08020 | glutathione S-transferase mul | 2.0 |
| Day 14 | | |
| U09579 | CDKN1A | 7.9 |
| U07418 | mutL protein homolog1 (MLH1) | 3.8 |
| U48296 | nuclear tyrosine phosphatase (PRL1) | 3.7 |
| U12779 | MAPKAP Kinase 2 | 3.3 |
| D15057 | defender against cell death 1(DAD1) | 3.2 |
| J04111 | jun proto-oncogene | 3.1 |
| L07597 | S6KII alpha 1 | 3.1 |
| M23619 | high mobility group protein (HMG-I) | 2.8 |
| X69391 | 60s ribosomal protein L6 | 2.5 |
| L25080 | Ras homolog A (RhoA) | 2.5 |
| U12979 | PC4 | 2.5 |
| X08804 | ras-related protein RAP-1B | 2.4 |
| M74524 | ubiquitin-conjugating enzyme E2 | 2.2 |
| M17733 | thymosin beta 4 | 2.2 |
| U28014 | caspase 4 | 2.2 |
| U51004 | PKC inhibitor 1 | 2.2 |
| U08316 | S6KII alpha 3 | 2.0 |

Of considerable interest are the limited detectable alterations in gene expression in the cells between 3-5 days after infection, preceding evidence of viral replication. Concomitant with evidence of the HIV replicative cycle (FIG. 1), a resurgence of gene expression begins to manifest (Table 2, days 7-14). Albeit the majority of cells are maximally producing HIV by day 10-16 (FIG. 1), only a limited repertoire of genes is upregulated compared to control macrophages (Table 2). Among these are several G-protein related molecules, which could reflect cell-cell transmission and HIV-1 induced signaling. MutL protein homolog 1 (MLH1), a component of the DNA mismatch repair gene (Modrich, P. (1997) "STRAND-SPECIFIC MISMATCH REPAIR IN MAMMALIAN CELLS," J Biol Chem 272:24727-30) is also increased consistently, not only within a few hours of encountering the virus (Table 1), but during the progression of infection (days 1, 5, 7 and 14) (Table 2). This protein could be playing a role in aiding to repair DNA damage after viral integration into the host and thus preserving genome stability to continue the viral life cycle. Furthermore, transcription of the anti-apoptotic gene DAD1 (Hong, N. A. et al. (2000) "MICE LACKING DAD1, THE DEFENDER AGAINST APOPTOTIC DEATH-1, EXPRESS ABNORMAL N-LINKED GLYCOPROTEINS AND UNDERGO INCREASED EMBRYONIC APOPTOSIS. Dev Biol 220:76-84) is enhanced at the peak of viral replication. Although the proteasome inhibitor HPI31 subunit (Table 2) is elevated at 3 days after infection, it is dramatically decreased during replication, consistent with evidence that proteasome activity is essential for viral maturation (Schubert, U. et al. (2000) "PROTEASOME INHIBITION INTERFERES WITH GAG POLYPROTEIN PROCESSING, RELEASE, AND MATURATION OF HIV-1 AND HIV-2," Proc Natl Acad Sci USA 97:13057-13062). This may reflect a tight control of the macrophage metabolism to regulate protein turnover at this late stage of infection to preserve integrity of viral protein or host cell factors necessary for efficient virion maturation and release (Schubert, U. et al. (2000) "PROTEASOME INHIBITION INTERFERES WITH GAG POLYPROTEIN PROCESSING, RELEASE, AND MATURATION OF HIV-1 AND HIV-2," Proc Natl Acad Sci USA 97:13057-13062).

D. Increased CDKN1a Gene and Protein Expression in Virus Infected Macrophages

Figure 3A:
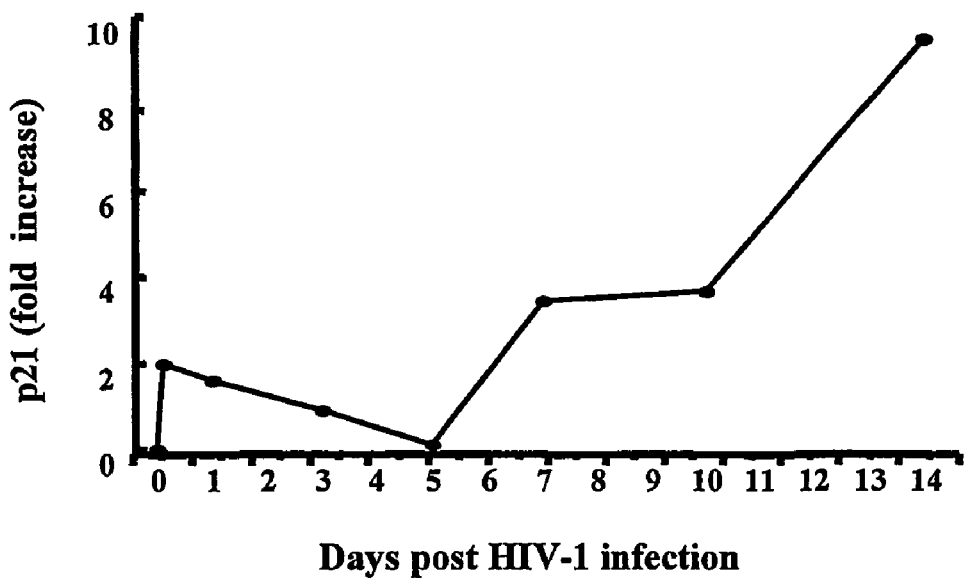
FIGS. 3A-3D demonstrate increased p21 (CDKN1A) gene expression in HIV-1 infected macrophages.
Figure 3B:
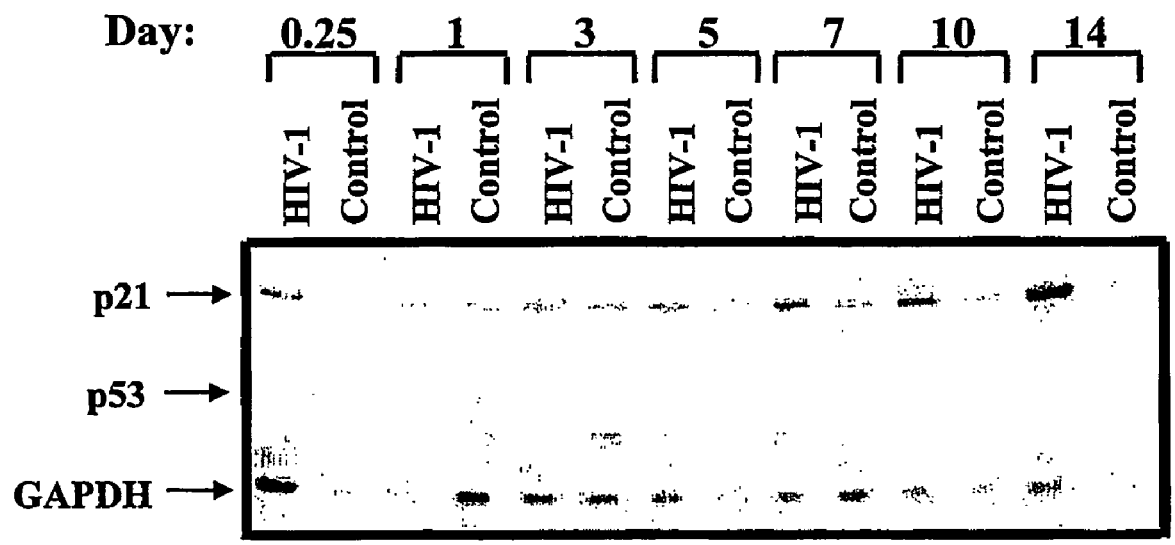
Figure 3C:
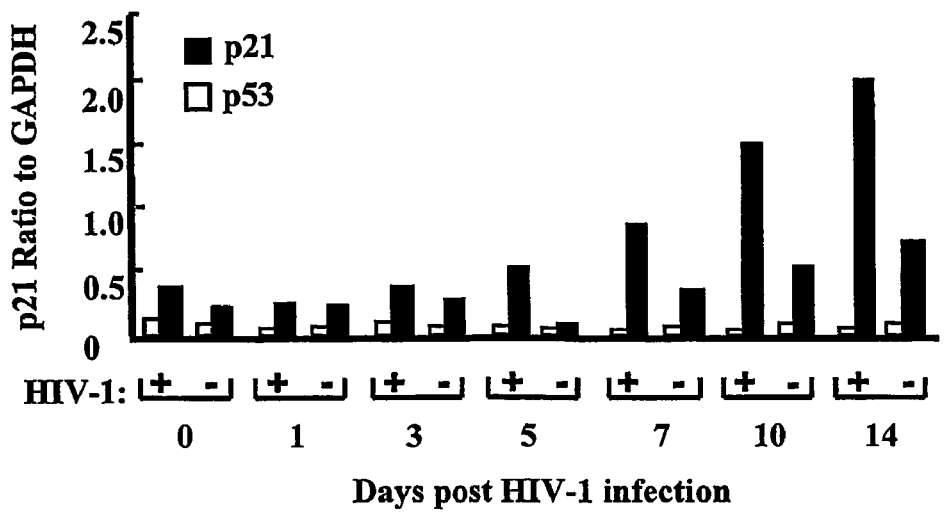
Figure 3D:
Figure 4A:
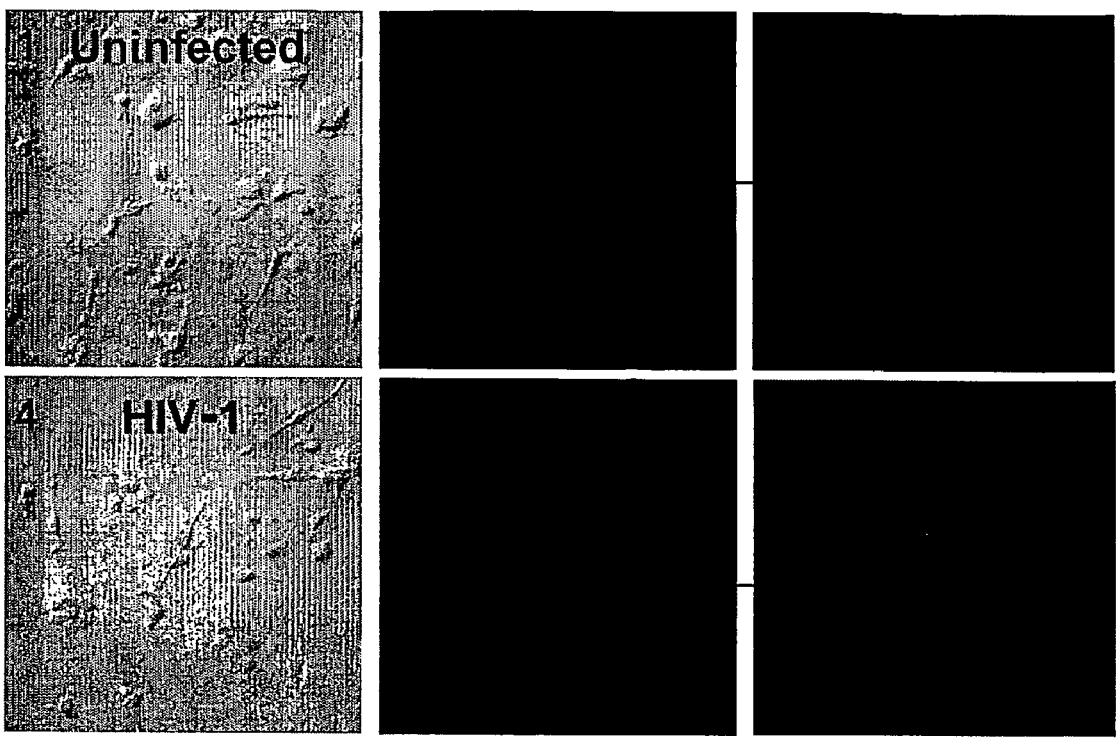
FIGS. 4A-4C illustrate that HIV-1-infected macrophages express increased p21 protein.
Figure 4B:
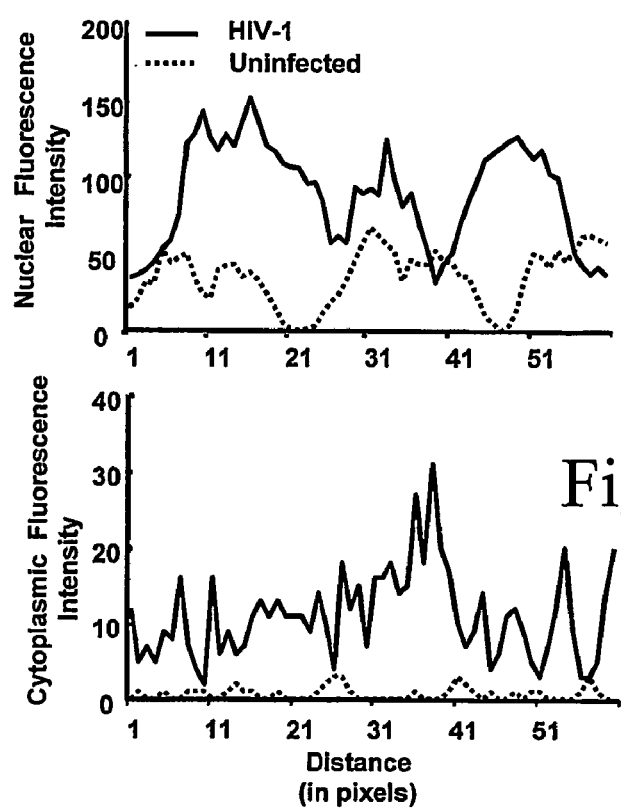
Figure 4C:
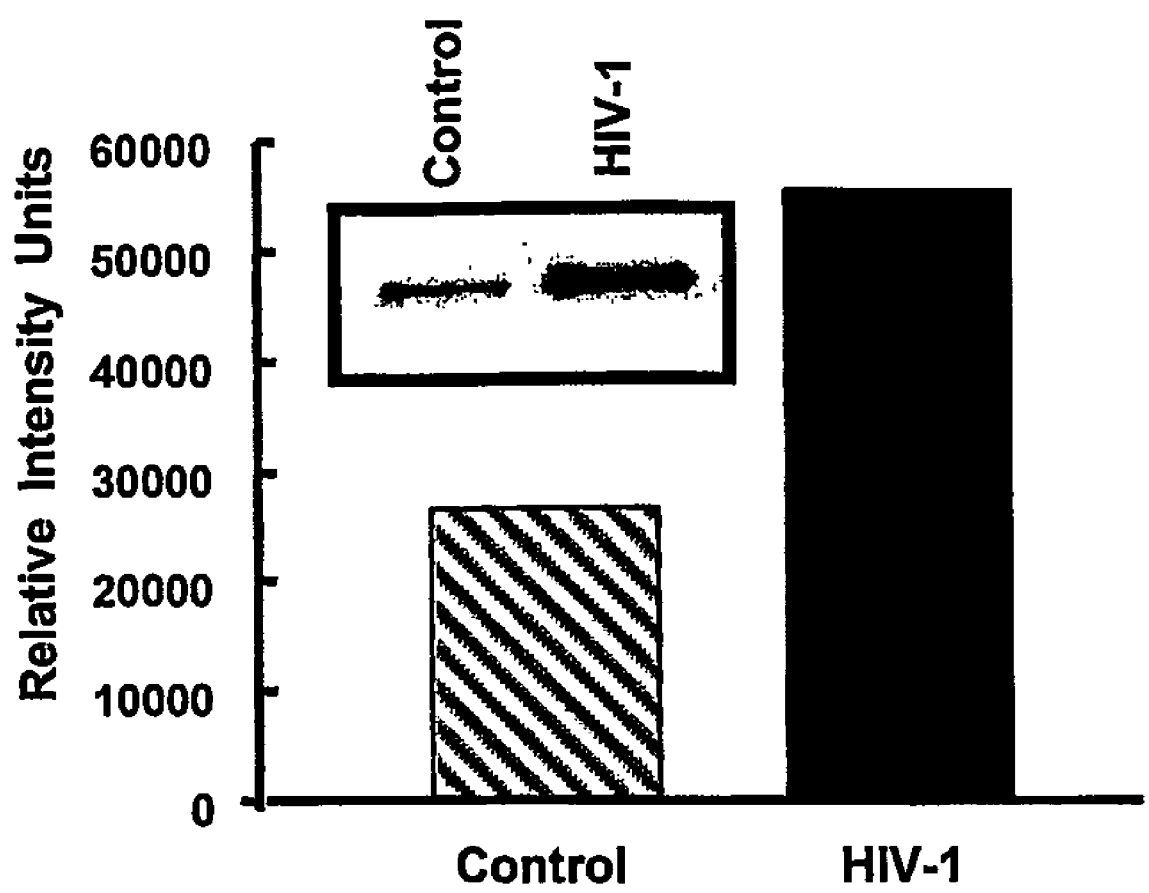

Although all of the virus-induced genes discussed above can be exploited as targets for drugs that would inhibit HIV-1 propagation, the unique biphasic expression pattern of CDKN1A makes it a preferred gene for inhibiting HIV, but does not rule out the additional genes as potential regulatory candidates. Because it is rapidly upregulated following HIV-1 binding/entry and then again during the emergence of viral replication (FIG. 3A), this gene is selected for further study. RNAse protection assay (RPA) confirmed the rapid induction of CDKN1A (FIG. 3B; FIG. 3C), followed by maximum expression concomitant with viral infection with no corresponding changes in another cell cycle related gene p53. Macrophages infected with HIV-1$_{BAL}$, a laboratory viral isolate (ADA) or a primary clinical isolate (727) that are analyzed for p21 transcription using PCR reveal expression of p21 (FIG. 3D). To further explore the relationship between viral infection and p21, p21 protein expression is examined by immunofluorescence. Not only increased nuclear, but also cytoplasmic p21 staining is observed in infected cells (FIG. 4A; FIG. 4B), consistent with enhanced protein expression in whole cell lysates detected by western blot (FIG. 4C).

Figure 6A:
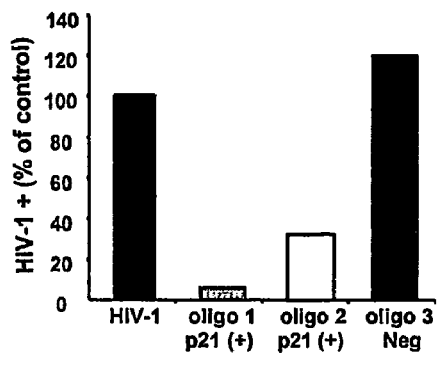
FIGS. 6A-6D show the results of siRNA for p21 and its effect on HIV infection.

To determine whether the increased p21 influenced viral life cycle, the cells are treated with two distinct p21 anti-sense oligonucleotides (SEQ ID NO. 7 and SEQ ID NO. 9). Both oligonucleotides reduce viral replication as assessed by p24 levels, most evident at day 12 when untreated cells show substantial HIV-1 production. In contrast, a missense control oligonucleotide (SEQ ID NO. 13) did not suppress HIV-1 p24 (FIG. 6A). The oligonucleotides have no negative effect on cell viability in infected or uninfected macrophage cultures as determined by cell number, morphology and ultrastuctural analysis. Moreover, the p21 oligos have no direct effect on macrophage CD4 nor CCR5.

E. Effect of CDDO on HIV-1 Replication

The ability of p21 oligonucleotides to block HIV-1 replication prompted the exploration of potential therapeutically relevant mechanisms of modulating p21 to inhibit HIV-1. It has been reported that peroxisome proliferator-activated receptor gamma (PPARγ) ligands, one of which includes the synthetic triterpenoid CDDO, modulate p21 activity (Wang, Y. et al. (2000) "A SYNTHETIC TRITERPENOID, 2-CYANO-3,12-DI-OXOOLEANA-1,9-DIEN-28-OIC ACID (CDDO), IS A LIGAND FOR THE PEROXISOME PROLIFERATOR-ACTIVATED RECEPTOR GAMMA," Mol Endocrinol 14:1550-1556); Wakino, S. et al. (2001) "PEROXISOME PROLIFERATOR-ACTIVATED RECEPTOR GAMMA LIGANDS INHIBIT MITOGENIC INDUCTION OF P21 (CIP1) BY MODULATING THE PROTEIN KINASE CDELTA PATHWAY IN VASCULAR SMOOTH MUSCLE CELLS," J Biol Chem 276, 47650-47657). To examine the effect of this synthetic triterpenoid, CDDO (0.1 μM) and its derivative di-CDDO are added prior to, or at the time of, infection of macrophages with HIV-1, resulting in a dose dependent suppression in the release of the viral protein p24 Ag (FIG. 5A). Without reducing cell viability or cell number, both CDDO and di-CDDO dramatically reduced the levels of detectable virus (FIG. 5D; FIG. 5B). Paradoxically, CDDO and di-CDDO variably decrease p21 protein levels concomitant with reducing HIV infection (FIGS. 5C and 5E). Moreover, p21 protein accumulates in uninfected cells, suggesting a post-translational effect on the p21 pathway. FIG. 5E shows the result of an investigation of macrophages infected with HIV-1$_{BaL}$ or ADA and treated or not with CDDO (0.1 μM) and analyzed by PCR for p21 and GAPDH. FIG. 5F shows the result of an investigation in which supernatants (12 days) collected from HIV-1$_{BaL}$, ADA or 727 infected cells that were treated or not with CDDO are analyzed for viral replication by p24 ELISA.

Example 3

Analysis of Gene Silencing

Gene silencing was carried out using SMARTpool™ si RNA duplexes (Dharmacon Research, Inc.; Smart Pool siRNA p21 waf1; Catalog No. M-003471-00-05), which targets CDKN1A. A non-specific si RNA pool (Dharmacon) was also utilized as a negative control.

After preparing siRNA:Lipofectamine 2000 complexes cells were transfected according to manufacture's instructions (Invitrogen-Life Technologies). Macrophages were infected after four days of transfection. The results of siRNA for p21 and its effect on HIV infection are shown in FIGS. 6B-6D.

P21 specific oligonucleotides (SEQ ID NO. 7 and SEQ ID NO. 9, 50 nM), but not control oligonucleotide (SEQ ID NO. 14) are found to inhibit HIV-1 growth in replicate cultures as determined by p24 levels (day 12 shown) (% of positive HIV control, no oligo treatment) (FIG. 6A).

Figure 6B:
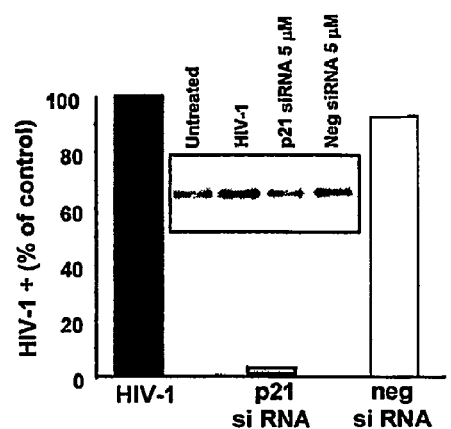
Figure 6C:
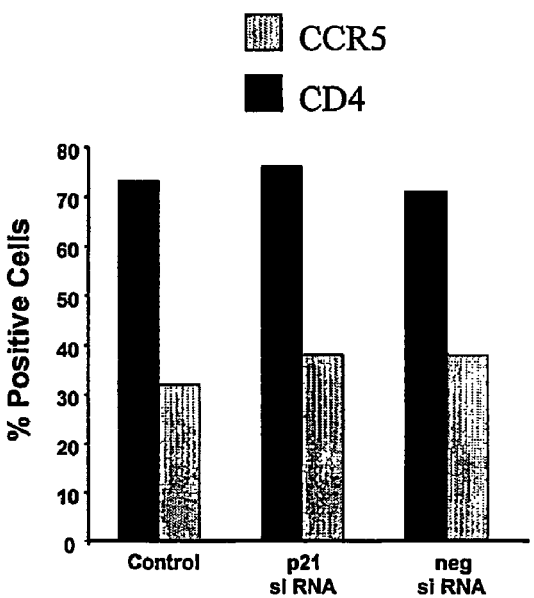
Figure 6D:
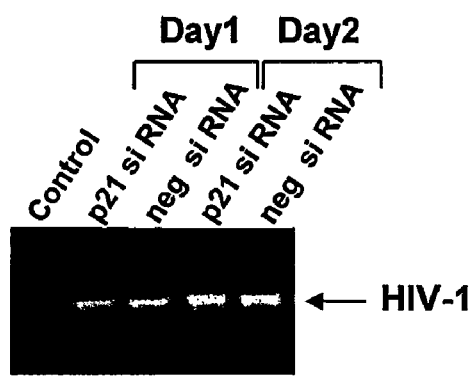

Macrophages were also treated with p21 siRNA duplexes (5 nM) five days prior to HIV infection and the effect on HIV-growth was determined (% of positive HIV control, no siRNA treatment) (representative experiment, n=3) (FIG. 6B). The percent of HIV-1 infection was determined comparing the p24 levels in untreated vs oligo or siRNA treated macrophages. Cells treated with p21 and negative control siRNA (5 days) were also analyzed by flow cytometry for CD4 and CCR5 cell surface expression (FIG. 6C). Nested PCR was employed in order to detect pro-viral DNA on days 1 and 3 after HIV-1$_{BaL}$ infection in macrophages treated with p21 or control siRNA or negative control si RNA. Control represents uninfected cells (FIG. 6D).

The results obtained with the antisense oligonucleotides were confirmed using gene silencing technology. Macrophages treated with CDKN1A si RNA duplexes, show a reduction in HIV-1 replication as determined by p24 ELISA on 14 day supernatants. This is not the case if macrophages are treated with a non-specific si RNA duplex control.

Example 4

Analysis of Effect of Vpr on p21 Expression

Figure 7A:
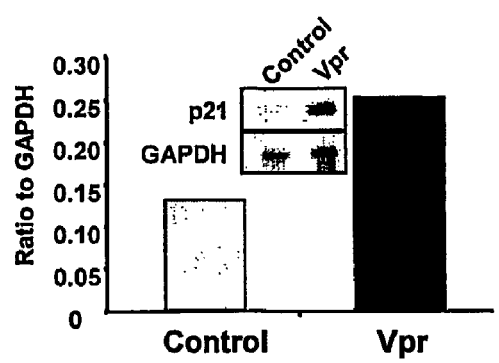
FIGS. 7A-7D show the induction of p21 gene and protein expression by Vpr.
Figure 7B:
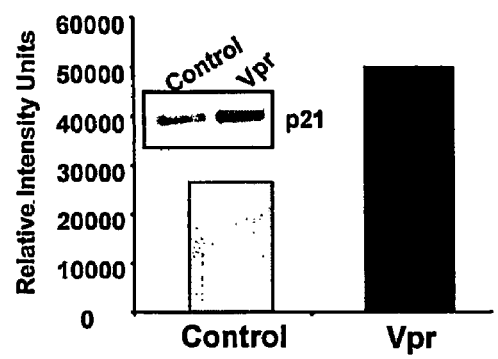

As indicated above, the HIV-1 Vpr gene product has been found to prevent cell proliferation by activating p21 expression (Chowdhury I. H. et al. (2003) "HIV-1 VPR ACTIVATES CELL CYCLE INHIBITOR P21/WAF1/CIP1: A POTENTIAL MECHANISM OF G2/M CELL CYCLE ARREST," Virol. 305:371-377). Macrophages were treated with Vpr (6 μg/ml) for 3 hr and found to show increased gene transcription and protein expression for p21 when treated with Vpr (FIG. 7A and FIG. 7B).

Figure 7C:
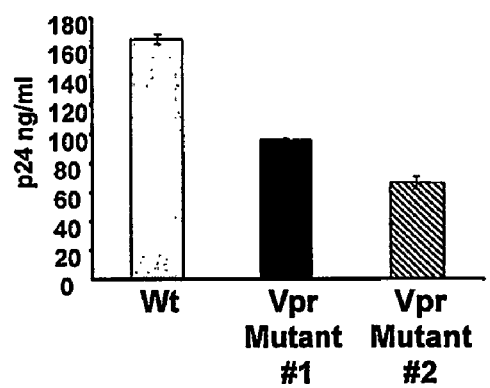
Figure 7D:
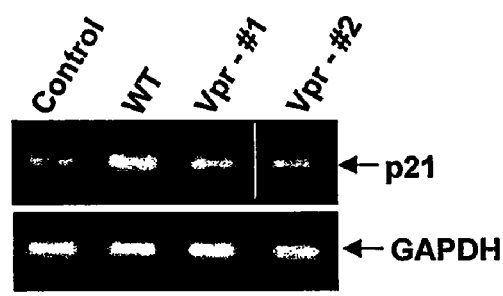

The expression of p21 and GADPH in these cells was evaluated using PCR. For such experiments, macrophages are infected with the wild virus type clone pNLAD8, or pNLAD8 Vpr minus (#1) or pNLAD8-delta R (#2) R5 macrophage tropic viruses and 12 day supernatants analyzed by p24 ELISA (FIG. 7C). The total RNA from cells infected with the indicated viruses was analyzed for p21 and GAPDH by PCR (FIG. 7D; representative experiment, n=2).

Example 5

Analysis of Temporal Events Associated with the Initial Virus-Macrophage Encounter The present invention demonstrates that HIV-1 infection promotes successful viral replication by modulating macrophage gene transcription. In comparison to previous studies, using viral envelope gp120 (Popik, W. et al. (2000) "EXPLOITATION OF CELLULAR SIGNALING BY HIV-1: UNWELCOME GUESTS WITH MASTER KEYS THAT SIGNAL THEIR ENTRY," Virology 276:1-6; Cicala, C. et al. (2002) "HIV ENVELOPE INDUCES A CASCADE OF CELL SIGNALS IN NON-PROLIFERATING TARGET CELLS THAT FAVOR VIRUS REPLICATION," Proc. Natl. Acad. Sci. USA 99:9380-9385; Liu, Q. H. et al. (2000) "HIV-1 GP120 AND CHEMOIKINES ACTIVATE ION CHANNELS IN PRIMARY MACROPHAGES THROUGH CCR5 AND CXCR4 STIMULATION," Proc. Natl. Acad. Sci. USA 97:4832-4837), one aspect of the invention relates to the finding that intact, infectious R5HIV-1 induces a cascade of events associated with reproducible alteration of gene transcription in primary macrophage hosts. Consistent with viral binding to CD4 and CCR5 seven transmembrane G protein receptors, viral initiated signal transduction induces transcriptional changes. While the functional significance attributable to each of the 134 genes upregulated within hours after viral binding is complex, the data support an initial burst of transcriptional activity followed by a quiescent phase and a resurgence of new genes associated with viral replication. In addition to phosphorylation of p38 MAPK, HIV-1 enhanced gene expression of p38 MAPK and downstream mediators, such as, MAPKAP-2, which may be critical in early post-entry and late stages of HIV-1 infection (Del Corno, M. et al. (2001) "HIV-1 GP120 AND CHEMOKINE ACTIVATION OF PYK2 AND MITOGEN-ACTIVATED PROTEIN KINASES IN PRIMARY MACROPHAGES MEDIATED BY CALCIUM-DEPENDENT, PERTUSSIS TOXIN-INSENSITIVE CHEMOKINE RECEPTOR SIGNALING," Blood 98:2909-2916; Shapiro, L. et al. (1998) "ROLE OF P38 MITOGEN-ACTIVATED PROTEIN KINASE IN HIV TYPE 1 PRODUCTION IN VITRO," Proc. Natl. Acad. Sci. USA 95:7422-7426 (1998), and p38 MAPK also plays an important role in multiple aspects of the immune response (Dong, C. et al. (2002) "MAP KINASES IN THE IMMUNE RESPONSE," Ann. Rev. Immunol 20, 55-72 (2002). MAPK also contributes to chemokine expression and recruitment of leukocytes, and inhibition of p38 MAPK reportedly also abrogates gp120-induced MMP9 in T cells (Misse, D. et al. (2001) "HIV-1 GLYCOPROTEIN 120 INDUCES THE MMP-9 CYTOPATHOGENIC FACTOR PRODUCTION THAT IS ABOLISHED BY INHIBITION OF THE P38 MITOGEN-ACTIVATED PROTEIN KINASE SIGNALING PATHWAY," Blood 98:541-547). MMP9, a member of the matrix metalloproteinase gene family is one of the genes expressed at day 3 after viral infection of macrophages that can facilitate the migration of HIV-infected monocytes across the vascular endothelium (Dhawan, S. et al. (1995) "HIV-1 INFECTION ALTERS MONOCYTE INTERACTIONS WITH HUMAN MICROVASCULAR ENDOTHELIAL CELLS," J Immunol 154:422-432 (1995) and has been detected in the cerebrospinal fluids of HIV-1 patients (Sporer, B. et al. (1998) "PRESENCE OF MATRIX METALLOPROTEINASE-9 ACTIVITY IN THE CEREBROSPINAL FLUID OF HUMAN IMMUNODEFICIENCY VIRUS-INFECTED PATIENTS," J. Infect. Dis. 178:854-857). Recruitment of viral host cells may also occur in response to increased MCP-1 expression consistent with the results obtained by other investigators (Mengozzi, M. et al. (1999) "HUMAN IMMUNODEFICIENCY VIRUS REPLICATION INDUCES MONOCYTE CHEMOTACTIC PROTEIN-1 IN HUMAN MACROPHAGES AND U937 PROMONOCYTIC CELLS," Blood 93:1851-1857). Enhanced gene transcription for other inflammatory mediators associated with increased viral replication in macrophages and pathophysiology of HIV, including TNFα, IP-10, MRP14, IL-8 and LIF (Lane, B. R. et al. (2001) "INTERLEUKIN-8 STIMULATES HUMAN IMMUNODEFICIENCY VIRUS TYPE 1 REPLICATION AND IS A POTENTIAL NEW TARGET FOR ANTIRETROVIRAL THERAPY," J Virol 75:8195-202; Strasser, F. et al. (1997) "ELEVATED SERUM MACROPHAGE INHIBITORY FACTOR-RELATED PROTEIN (MRP) 8/14 LEVELS IN ADVANCED HIV INFECTION AND DURING DISEASE EXACERBATION," J Acquir Immune Defic Syndr Hum Retrovirol 16:230-238); Kinter, A. et al. (2000) "CHEMOKINES, CYTOKINES AND HIV: A COMPLEX NETWORK OF INTERACTIONS THAT INFLUENCE HIV PATHOGENESIS," Immunol Rev 177:88-98; Agostini, C. et al. (2000) "CXC CHEMOKINES IP-10 AND MIG EXPRESSION AND DIRECT MIGRATION OF PULMONARY CD8+/CXCR3+T CELLS IN THE LUNGS OF PATIENTS WITH HIV INFECTION AND T-CELL ALVEOLITIS," Am J Respir Crit. Care Med 162:1466-1473; Broor, S. et al. (1994) "STIMULATION OF HIV REPLICATION IN MONONUCLEAR PHAGOCYTES BY LEUKEMIA INHIBITORY FACTOR," J Acquir Immune Defic Syndr 7:647-654) were also reproducibly detected. Cell homeostasis and genomic stability may be aided by glutathione synthetase, heme oxygenase-1 and MLH1 ensuring the survival of the macrophage to allow viral replication. Furthermore, reduction of lysosomal enzyme activity can potentially enhance virus entry and infectivity in the host cell (Fredericksen, B. L. et al. (2002) "INHIBITION OF ENDOSOMAL/LYSOSOMAL DEGRADATION INCREASES THE INFECTIVITY OF HUMAN IMMUNODEFICIENCY VIRUS," J Virol 76, 11440-11446).

Macrophages can co-exist with the virus for a prolonged time, during which they contribute to the pathogenesis of AIDS, acting as viral reservoirs and transmitting HIV-1 to neighboring cells. Although proapoptotic genes for caspase 3, 4 and 8 were upregulated within 3 hours after infection, the antiapoptotic genes bcl-x, DAD1 and IEX-1L (Wu, M. X. et al. (1998) "IEX-1L, AN APOPTOSIS INHIBITOR INVOLVED IN NF-KAPPAB-MEDIATED CELL SURVIVAL," Science 281:998-1001; Antonsson, B. et al. (2000) "THE BCL-2 PROTEIN FAMILY," Exp Cell Res 256:50-57; Hong, N. A. et al. (2000) "MICE LACKING DAD1, THE DEFENDER AGAINST APOPTOTIC DEATH-1, EXPRESS ABNORMAL N-LINKED GLYCOPROTEINS AND UNDERGO INCREASED EMBRYONIC APOPTOSIS," Dev Biol 220:76-84), were also increased by HIV-1. The balance between pro and anti-apoptotic genes must favor the survival of virus-infected macrophages in vitro and in vivo, as a strategy developed by the virus to prolong the life of the host for its uninterrupted cycle of replication.

As indicated above, following the initial HIV-1 induced burst of gene expression (6-24 hr), little evidence of transcriptional activity occurred until the onset of viral replication, when an increase in host molecules was again detected (day 7-14). The lack of induction of new host molecules during this interim period may allow the infected cells to escape immune surveillance while the virus initiates its life cycle to commence replication. Once ready to replicate, new transcription may be essential to facilitate the replicative process. For example the data indicate CDKN1A/p21 as a host molecule critical to viral replication in macrophages. CDKN1A is a cyclin-dependent kinase inhibitor induced during G1 cell cycle arrest by p53-dependent pathway following DNA damage, as well as p53-independent pathways involving growth factors Dotto, G. P. (2000) "p21(WAF1/CIP1): MORE THAN A BREAK TO THE CELL CYCLE?," Biochim Biophys Acta 1471:M43-56; Ogryzko, V. V. et al. (1997) "WAF1 RETARDS S-PHASE PROGRESSION PRIMARILY BY INHIBITION OF CYCLIN-DEPENDENT KINASES," Mol Cell Biol 17, 4877-4882 (1997); Zeng, Y. X. et al. (1996) "REGULATION OF p21WAF1/CIP1 EXPRESSION BY p53-INDEPENDENT PATHWAYS," Oncogene 12:1557-1564). Progressive upregulation of p21 mRNA and protein have also been associated with maturation of hematopoietic progenitor cells (Steinman, R. A. et al. (1998) "REGULATION OF P21 (WAF1) EXPRESSION DURING NORMAL MYELOID DIFFERENTIATION," Blood 91:4531-4542), but its connection with viral replication in macrophages has not been demonstrated. Increased p21 in skin lesions of human papillomavirus has been found to be further enhanced by HIV co-infection (Arany, I. et al. (1997) "p53, WAF1/CIP1 AND MDM2 EXPRESSION IN SKIN LESIONS ASSOCIATED WITH HUMAN PAPILLOMAVIRUS AND HUMAN IMMUNODEFICIENCY VIRUS," Anticancer Res 17:1281-1285). An upregulation in CDKN1A induced in macrophages infected with the opportunistic bacteria, Mycobacterium avium (Greenwell-Wild, T. et al. (2002) "MYCOBACTERIUM AVIUM INFECTION AND MODULATION OF HUMAN MACROPHAGE GENE EXPRESSION," J Immunol 169:6286-6297 (2002) may also be linked to the increased susceptibility for HIV replication reported in these cells (Wahl, S. M. et al. (1998) "MYCOBACTERIUM AVIUM COMPLEX AUGMENTS MACROPHAGE HIV-1 PRODUCTION AND INCREASES CCR5 EXPRESSION," Proc Natl Acad Sci USA 95:12574-12579). The specific role played by CDKN1A in HIV-1 macrophage infection has not been fully determined, however, it may either directly or indirectly enhance viral replication. Although originally described as a cell cycle inhibitor, CDKN1A has more recently been associated with apoptosis, cytoplasmic regulation of nuclear import, and transcriptional regulation by its capacity to act as a transcriptional co-factor/adaptor molecule (Coqueret, O. (2003) "NEW ROLES FOR P21 AND P27 CELL-CYCLE INHIBITORS: A FUNCTION FOR EACH CELL COMPARTMENT?," Trends Cell Biol 13:65-70; LaBaer, J. et al. (1997) "NEW FUNCTIONAL ACTIVITIES FOR THE P21 FAMILY OF CDK INHIBITORS," Genes Dev 11:847-862). In this regard, HIV-1 Tat is essential for efficient viral replication and interacts with cAMP response element binding protein (CREB) and the transcriptional coactivator p300 (Hottiger, M. O. et al. (1998) "INTERACTION OF HUMAN IMMUNODEFICIENCY VIRUS TYPE 1 TAT WITH THE TRANSCRIPTIONAL COACTIVATORS P300 AND CREB BINDING PROTEIN," J Virol 72:8252-8256), which can be stimulated by the coexpression of CDKN1A through a novel transcriptional repression domain on p300 (Snowden, A. W. et al. (2000) "A NOVEL TRANSCRIPTIONAL REPRESSION DOMAIN MEDIATES P21(WAF1/CIP1) INDUCTION OF P300 TRANSACTIVATION," Mol Cell Biol 20, 2676-2686). In addition, an increase in TBP-1 could be a strategy of the virus to ensure efficient regulation of viral transcription and replication. A causal relationship is thus established between HIV and induced p21 expression, which appears to support viral replication in macrophages.

While the initial enhancement of p21 gene expression likely represents a downstream consequence of CCR5/G protein signaling, the rise in gene transcription could be due to either intracellular or extracellular viral signals. Definition of such factors may provide a means of altering host involvement in viral infection and replication kinetics, possibly in conjunction with antiviral therapy. The presence of p21 in the nucleus has been related to its cell cycle functions (Dotto, G. P. (2000) "P21(WAF1/CIP1): MORE THAN A BREAK TO THE CELL CYCLE?" Biochim Biophys Acta 1471:M43-56) and the cytoplasmic localization of this protein has been implicated in controlling/preventing apoptosis of alveolar macrophages and during monocytic differentiation (Tomita, K. et al. (2002) "INCREASED P21(CIP1/WAF1) AND B CELL LYMPHOMA LEUKEMIA-X(L) EXPRESSION AND REDUCED APOPTOSIS IN ALVEOLAR MACROPHAGES FROM SMOKERS," Am J Respir Crit. Care Med 166:724-731; Asada, M. et al. (1999) "APOPTOSIS INHIBITORY ACTIVITY OF CYTOPLASMIC P21(CIP1/WAF1) IN MONOCYTIC DIFFERENTIATION," Embo J 18:1223-1234). Increased p21 protein in both nuclear and cytoplasmic compartments of HIV-1 infected macrophages may both generate a permissive environment for viral replication and prevent the death of the host cells. The ability to dramatically suppress HIV-1 replication with the p21 anti-sense oligonucleotides indicates that CDKN1A is critical in promoting viral replication. CDDO a synthetic oleanane triterpenoid with potent differentiating, anti-proliferative and anti-inflammatory activities (Suh, N. et al. (1999) "A NOVEL SYNTHETIC OLEANANE TRITERPENOID, 2-CYANO-3,12-DIOXOOLEAN-1,9-DIEN-28-OIC ACID, WITH POTENT DIFFERENTIATING, ANTIPROLIFERATIVE, AND ANTI-INFLAMMATORY ACTIVITY," Cancer Res 59:336-341) being developed as a chemotherapeutic agent for cancer (Stadheim, T. A. et al. (2002) "THE NOVEL TRITERPENOID 2-CYANO-3,12-DIOXOOLEANA-1,9-DIEN-28-OIC ACID (CDDO) POTENTLY ENHANCES APOPTOSIS INDUCED BY TUMOR NECROSIS FACTOR IN HUMAN LEUKEMIA CELLS," J Biol Chem 277:16448-16455 (2002)) may also inhibit HIV-1 via a p21-dependent pathway, possibly by a post-translational mechanism. CDDO has been recently identified as a member of a new class of nuclear PPARγ ligands (Wang, Y. et al. (2000) "A SYNTHETIC TRITERPENOID, 2-CYANO-3,12-DIOXOOLEANA-1,9-DIEN-28-OIC ACID (CDDO), IS A LIGAND FOR THE PEROXISOME PROLIFERATOR-ACTIVATED RECEPTOR GAMMA," Mol Endocrinol 14:1550-1556), which reportedly reduces p21 protein expression (Wakino, S. et al. (2001) "PEROXISOME PROLIFERATOR-ACTIVATED RECEPTOR GAMMA LIGANDS INHIBIT MITOGENIC INDUCTION OF P21(CIP1) BY MODULATING THE PROTEIN KINASE Cδ PATHWAY IN VASCULAR SMOOTH MUSCLE CELLS," J Biol Chem 276:47650-47657). PPARγ is a nuclear hormone receptor implicated in the gene regulation of lipid and glucose metabolism, cellular differentiation and control of macrophage inflammatory responses (Bar-Tana, J. (2001) "PEROXISOME PROLIFERATOR-ACTIVATED RECEPTOR GAMMA (PPAR-GAMMA) ACTIVATION AND ITS CONSEQUENCES IN HUMANS," Toxicol Lett 120:9-19; Delerive, P. (2001) "PEROXISOME PROLIFERATOR-ACTIVATED RECEPTORS IN INFLAMMATION CONTROL," J Endocrinol 169:453-459). Natural and synthetic agonists of PPARγ have been recently shown to inhibit retroviral replication (Hayes, M. M. et al. (2002) "PEROXISOME PROLIFERATOR-ACTIVATED RECEPTOR GAMMA AGONISTS INHIBIT HIV-1 REPLICATION IN MACROPHAGES BY TRANSCRIPTIONAL AND POST-TRANSCRIPTIONAL EFFECTS," J Biol Chem 277:16913-16919) and although the target was not defined, some studies have implicated TNF-α in the PPARγ-induced suppression of HIV (Skolnik, P. R. et al. (2002) "STIMULATION OF PEROXISOME PROLIFERATOR-ACTIVATED RECEPTORS ALPHA AND GAMMA BLOCKS HIV-1 REPLICATION AND TNFALPHA PRODUCTION IN ACUTELY INFECTED PRIMARY BLOOD CELLS, CHRONICALLY INFECTED U1 CELLS, AND ALVEOLAR MACROPHAGES FROM HIV-INFECTED SUBJECTS," J Acquir Immune Defic Syndr 31:1-10). Still unresolved is whether the antiviral effect of CDDO is mediated through this receptor entirely by its effect on p21 function by post-translational modification (Scott, M. T. et al. (2000) "REVERSIBLE PHOSPHORYLATION AT THE C-TERMINAL REGULATORY DOMAIN OF P21(WAF1/CIP1) MODULATES PROLIFERATING CELL NUCLEAR ANTIGEN BINDING," J Biol Chem 275:11529-11537), through inhibition of NFκB (Straus, D. S. et al. (2000) "15-DEOXY-DELTA 12,14-PROSTAGLANDIN J2 INHIBITS MULTIPLE STEPS IN THE NF-KAPPA B SIGNALING PATHWAY," Proc Natl Acad Sci USA 97:4844-4849, modulation of p38 MAPK (Kim, J. Y. et al. (2002) "INVOLVEMENT OF P38 MITOGEN-ACTIVATED PROTEIN KINASE IN THE CELL GROWTH INHIBITION BY SODIUM ARSENITE," J Cell Physiol 190:29-37 (2002) and/or the production of cytokines that regulate cellular and viral components, such as TGF-β (Li, C. Y. et al. (1995) "POTENTIAL ROLE OF WAF1/CIP1/P21 AS A MEDIATOR OF TGF-BETA CYTOINHIBITORY EFFECT," J Biol Chem 270:4971-4974; Wahl, S. M. et al. (1991) "MACROPHAGE- AND ASTROCYTE-DERIVED TRANSFORMING GROWTH FACTOR BETA AS A MEDIATOR OF CENTRAL NERVOUS SYSTEM DYSFUNCTION IN ACQUIRED IMMUNE Deficiency Syndrome," Exp Med 173:981-991). Comparison of genes upregulated by HIV in T lymphocytes (Corbeil, J. et al. (2001) "Temporal Gene Regulation During HIV-1 Infection Of Human CD4+ T Cells," Genome Res 11:1198-1204) with those identified in macrophage hosts also revealed an early increase in genes associated with cellular defense. However, increased expression of proapoptotic transcripts, and inhibition of mitochondria and DNA repair genes are also observed, which could explain the unavoidable death pathway in HIV-1 infected T cells and survival of macrophage hosts. The differential gene expression and cell specific modulation of host protein function as a result of HIV-1 infection in these cell populations may help better understand the reasons leading to HIV-induced apoptosis in T cells (Corbeil, J. et al. (2001) "Temporal Gene Regulation During HIV-1 Infection Of Human CD4+ T Cells," Genome Res 11:1198-1204; Clark, E. et al. (2000) "Loss of G(1)/S checkpoint In Human Immunodeficiency Virus Type-1-Infected Cells Is Associated With A Lack Of Cyclin-Dependent Kinase Inhibitor p21/Waf1. J Virol 74, 5040-5052), while allowing the macrophage to sustain a prolonged viral burden.

Since the macrophage represents a key target for HIV-1 infection and one of the major obstacles in eradicating the virus even during HAART (Igarashi, T. et al. (2001) "Macrophage Are The Principal Reservoir And Sustain High Virus Loads In Rhesus Macaques After The Depletion Of CD4+ T Cells By A Highly Pathogenic Simian Immunodeficiency Virus/HIV Type 1 Chimera (SHIV): Implications For HIV-1 Infections Of Humans," Proc Natl Acad Sci USA 98:658-663; Garbuglia, A. R. et al. (2001) "Dynamics Of Viral Load In Plasma And HIV DNA In Lymphocytes During Highly Active Antiretroviral Therapy (HAART): High Viral Burden In Macrophages After 1 Year Of Treatment," J Chemother 13:188-194), the above-described data analyzing the influence of HIV on the macrophage transcriptome reveals important insights into the pattern of host cell gene expression underlying viral success in this population. CDKN1A and other virus-regulated macrophage genes critical for HIV-1 replication provide mechanisms by which to target the macrophage reservoir and/or serve as prognostic markers of disease progression.

Finally, since anti-HIV therapy is limited by the side effects that have accompanied conventional anti-retroviral drugs, and the constant emergence of drug-resistant HIV strains, CDDO provides an important candidate drug to target HIV-1, particularly in conjunction with additional anti-viral therapy, to prevent or attenuate the infection of new viral hosts.

All publications and patent documents mentioned in this specification are herein incorporated by reference to the same extent as if each individual publication or patent document was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of attenuating the transmission or infection of a human immunodeficiency virus (HIV) to a cell contacted with an HIV comprising providing to said cell contacted with an HIV an inhibitor of p21, wherein said inhibitor is provided in an amount and duration sufficient to cause an attenuation of at least about 50% in said transmission or infection of said virus relative to an untreated cell, wherein said inhibitor is 2-cyano-3,12-dioxooleana-1,9-dien-28-oic acid (CDDO), di-CDDO; or a salt thereof.

2. A method of treating AIDS in an individual, comprising providing to HIV-1 infected cells of said individual, or to HIV-1 susceptible cells of such individual, an amount of a p21 inhibitor sufficient to attenuate the propagation of HIV, wherein said inhibitor is provided in an amount and duration sufficient to cause an attenuation of at least 50% in said propagation of HIV relative to untreated cells, wherein said inhibitor is 2-cyano-3,12-dioxooleana-1,9-dien-28-oic acid (CDDO), di-CDDO; or a salt thereof.

3. A method of inhibiting HIV-1 replication in an individual, comprising providing to HIV-1 infected cells of said individual an amount of a p21 inhibitor sufficient to attenuate the propagation of HIV, wherein said inhibitor is provided in an amount and duration sufficient to cause an attenuation of at least 50% in said propagation of HIV relative to untreated cells, wherein said inhibitor is 2-cyano-3,12-dioxooleana-1,9-dien-28-oic acid (CDDO), di-CDDO; or a salt thereof.

* * * * *